US011957530B2

(12) United States Patent
Katzman et al.

(10) Patent No.: US 11,957,530 B2
(45) Date of Patent: Apr. 16, 2024

(54) DISTRIBUTED SYSTEM FOR FABRICATING DENTAL ALIGNERS

(71) Applicant: SDC U.S. SmilePay SPV, Nashville, TN (US)

(72) Inventors: Jordan Katzman, Nashville, TN (US); Alex Fenkell, Nashville, TN (US)

(73) Assignee: SDC U.S. SmilePay SPV, Nashville, TN (US)

( * ) Notice: Subject to any disclaimer, the term of this patent is extended or adjusted under 35 U.S.C. 154(b) by 0 days.

(21) Appl. No.: 17/751,636

(22) Filed: May 23, 2022

(65) Prior Publication Data

US 2022/0280266 A1  Sep. 8, 2022

Related U.S. Application Data

(63) Continuation of application No. 17/148,437, filed on Jan. 13, 2021, now Pat. No. 11,337,778, which is a
(Continued)

(51) Int. Cl.
*A61C 7/00* (2006.01)
*A61C 7/08* (2006.01)
(Continued)

(52) U.S. Cl.
CPC .............. *A61C 7/002* (2013.01); *A61C 7/08* (2013.01); *G16H 10/60* (2018.01); *G16H 20/00* (2018.01); *G16H 40/20* (2018.01)

(58) Field of Classification Search
CPC .......... A61C 7/08; G16H 40/20; G16H 20/13; G16H 40/40; G16H 20/00
See application file for complete search history.

(56) References Cited

U.S. PATENT DOCUMENTS 4,002,162 A  1/1977 Weisser
4,003,132 A  1/1977 Beck
(Continued)

FOREIGN PATENT DOCUMENTS

AU  2015100268  5/2015
BE  1016074  2/2006
(Continued)

OTHER PUBLICATIONS

Lin, Alan C. "Integration of 3D CAD, reverse engineering and rapid prototyping in fabrication of invisible tooth aligner." 2005 IEEE International Conference on Systems, Man and Cybernetics. vol. 3. IEEE, 2005. (Year: 2005).*
(Continued)

*Primary Examiner* — Jason B Dunham
*Assistant Examiner* — Constantine Siozopoulos
(74) *Attorney, Agent, or Firm* — Foley & Lardner LLP

(57) ABSTRACT

A distributed system includes one or more servers configured to provide computing devices access to portals hosted by the one or more servers, where the portals include a patient intake portal accessible by a first computing device located at an office of an intake dentist or orthodontist, and an approving portal accessible by a second computing device remote from the first computing device. The distributed system includes a dental aligner fabrication system including a fabrication computing device and dental aligner fabrication equipment. The patient intake portal is configured to provide a plurality of status updates to the intake dentist or orthodontist regarding a status of the patient, where the plurality of status updates include an indication that the dental aligners have been sent to the patient.

22 Claims, 23 Drawing Sheets

Related U.S. Application Data continuation-in-part of application No. 17/247,296, filed on Dec. 7, 2020, now Pat. No. 11,094,414, which is a continuation of application No. 16/859,950, filed on Apr. 27, 2020, now Pat. No. 10,861,599, which is a continuation of application No. 16/130,762, filed on Sep. 13, 2018, now Pat. No. 10,636,522, said application No. 17/148,437 is a continuation-in-part of application No. 15/725,430, filed on Oct. 5, 2017, said application No. 16/130,762 is a continuation-in-part of application No. 15/725,430, filed on Oct. 5, 2017.

(60) Provisional application No. 62/660,141, filed on Apr. 19, 2018, provisional application No. 62/522,847, filed on Jun. 21, 2017.

(51) Int. Cl.
*G16H 10/60* (2018.01)
*G16H 20/00* (2018.01)
*G16H 40/20* (2018.01)

(56) References Cited

U.S. PATENT DOCUMENTS

| | | |
|---|---|---|
| 4,200,089 A | 4/1980 | Inoue |
| 4,763,791 A | 8/1988 | Halverson et al. |
| 5,093,901 A | 3/1992 | Cree et al. |
| 5,190,168 A | 3/1993 | French et al. |
| 5,385,155 A | 1/1995 | Kittelsen et al. |
| 5,816,255 A | 10/1998 | Fishman et al. |
| 5,882,192 A | 3/1999 | Bergersen |
| 5,975,893 A | 11/1999 | Chishti et al. |
| 6,121,565 A | 9/2000 | Allott, III |
| 6,227,851 B1 | 5/2001 | Chishti et al. |
| 6,394,801 B2 | 5/2002 | Chishti et al. |
| 6,450,807 B1 | 9/2002 | Chishti et al. |
| 6,488,499 B1 | 12/2002 | Miller |
| 6,582,225 B1 | 6/2003 | Bergersen |
| 6,632,089 B2 | 10/2003 | Rubbert et al. |
| 6,699,037 B2 | 3/2004 | Chishti et al. |
| 6,732,103 B1 | 5/2004 | Strick et al. |
| 6,761,560 B2 | 7/2004 | Miller |
| 7,037,108 B2 | 5/2006 | Chishti et al. |
| 7,077,647 B2 | 7/2006 | Choi et al. |
| 7,156,661 B2 | 1/2007 | Choi et al. |
| 7,188,073 B1 | 3/2007 | Tam et al. |
| 7,192,275 B2 | 3/2007 | Miller |
| 7,225,170 B1 | 5/2007 | Ryan, Jr. |
| 7,383,198 B1 | 6/2008 | Sepe |
| 7,467,022 B2 | 12/2008 | Bhagwat et al. |
| 7,523,044 B2 | 4/2009 | Rosenblood |
| 7,578,674 B2 | 8/2009 | Chishti et al. |
| 7,597,245 B1 | 10/2009 | Tillery |
| 7,716,062 B2 | 5/2010 | Bergersen |
| 7,738,989 B2 | 6/2010 | Taub et al. |
| 7,904,307 B2 | 3/2011 | Abolfathi et al. |
| 7,916,900 B2 | 3/2011 | Lanier |
| 7,967,145 B2 | 6/2011 | Tchouangang |
| 8,015,049 B1 | 9/2011 | Tam et al. |
| 8,075,306 B2 | 12/2011 | Kitching et al. |
| 8,087,932 B2 | 1/2012 | Liu |
| 8,092,215 B2 | 1/2012 | Stone-Collonge et al. |
| 8,145,340 B2 | 3/2012 | Taub et al. |
| 8,287,275 B2 | 10/2012 | Knutson |
| 8,303,301 B2 | 11/2012 | Bergersen |
| 8,562,338 B2 | 10/2013 | Kitching et al. |
| 8,577,493 B2 | 11/2013 | Taub et al. |
| 8,591,225 B2 | 11/2013 | Wu et al. |
| 8,636,510 B2 | 1/2014 | Kitching et al. |
| 8,651,859 B2 | 2/2014 | Chishti et al. |
| 8,731,280 B2 | 5/2014 | Kuo et al. |
| 8,740,614 B2 | 6/2014 | Wen et al. |
| 8,765,031 B2 | 7/2014 | Li et al. |
| 8,899,978 B2 | 12/2014 | Kitching et al. |
| 9,017,072 B2 | 4/2015 | Kitching et al. |
| 9,107,722 B2 | 8/2015 | Matov et al. |
| 9,168,113 B2 | 10/2015 | Wu et al. |
| 9,256,962 B2 | 2/2016 | Berry et al. |
| 9,364,297 B2 | 6/2016 | Kitching et al. |
| D764,061 S | 8/2016 | Furdui-Carr |
| 9,655,693 B2 | 5/2017 | Li et al. |
| 9,715,753 B2 | 7/2017 | Berry et al. |
| 9,757,065 B1 | 9/2017 | Suri et al. |
| 9,855,123 B2 | 1/2018 | Wolgin |
| 9,922,170 B2 | 3/2018 | Trosien et al. |
| 10,052,174 B2 | 8/2018 | Kitching et al. |
| 10,085,823 B2 | 10/2018 | Cao et al. |
| 10,134,286 B1 | 11/2018 | Elswick et al. |
| 10,136,972 B2 | 11/2018 | Sabina et al. |
| 10,231,801 B2 | 3/2019 | Korytov et al. |
| 10,342,638 B2 | 7/2019 | Kitching et al. |
| 10,383,705 B2 | 8/2019 | Shanjani et al. |
| 10,504,386 B2 | 12/2019 | Levin et al. |
| 10,595,966 B2 | 3/2020 | Carrier et al. |
| 10,636,105 B2 | 4/2020 | Pumphrey |
| 2001/0027481 A1 | 10/2001 | Whyel |
| 2002/0007290 A1 | 1/2002 | Gottlieb |
| 2002/0014357 A1 | 2/2002 | Hammonds |
| 2002/0028418 A1 | 3/2002 | Farag et al. |
| 2002/0029161 A1 | 3/2002 | Brodersen et al. |
| 2002/0116232 A1 | 8/2002 | Rapp et al. |
| 2002/0131565 A1 | 9/2002 | Scheuring et al. |
| 2002/0143574 A1 | 10/2002 | Karras et al. |
| 2002/0188478 A1 | 12/2002 | Breeland et al. |
| 2003/0138752 A1 | 7/2003 | Bergersen |
| 2003/0207227 A1 | 11/2003 | Abolfathi |
| 2003/0225594 A1 | 12/2003 | Bergersen |
| 2004/0073611 A1 | 4/2004 | Atwood |
| 2004/0091835 A1 | 5/2004 | Roetzer |
| 2004/0152036 A1 | 8/2004 | Abolfathi |
| 2004/0185415 A1 | 9/2004 | Ghim |
| 2004/0197728 A1 | 10/2004 | Abolfathi et al. |
| 2004/0250359 A1 | 12/2004 | Spivey |
| 2005/0159986 A1 | 7/2005 | Breeland et al. |
| 2005/0182654 A1 | 8/2005 | Abolfathi et al. |
| 2006/0019216 A1 | 1/2006 | Priluck et al. |
| 2006/0026051 A1 | 2/2006 | Rose |
| 2006/0040230 A1 | 2/2006 | Blanding et al. |
| 2006/0057541 A1 | 3/2006 | Kahwaty |
| 2006/0064329 A1 | 3/2006 | Abolfathi et al. |
| 2006/0093982 A1 | 5/2006 | Wen |
| 2006/0141416 A1 | 6/2006 | Knutson |
| 2006/0154198 A1 | 7/2006 | Durbin et al. |
| 2006/0167724 A1 | 7/2006 | Petersen et al. |
| 2006/0172261 A1 | 8/2006 | Garry |
| 2006/0173708 A1 | 8/2006 | Vining et al. |
| 2006/0275731 A1 | 12/2006 | Wen et al. |
| 2006/0275736 A1 | 12/2006 | Wen et al. |
| 2007/0005406 A1 | 1/2007 | Assadian et al. |
| 2007/0036320 A1 | 2/2007 | Mandalia et al. |
| 2007/0037116 A1 | 2/2007 | Knutson |
| 2007/0061166 A1 | 3/2007 | Ramasubramanian et al. |
| 2007/0102946 A1 | 5/2007 | Blackwell et al. |
| 2007/0128574 A1 | 6/2007 | Kuo et al. |
| 2007/0134613 A1 | 6/2007 | Kuo et al. |
| 2007/0238065 A1 | 10/2007 | Sherwood et al. |
| 2008/0059227 A1 | 3/2008 | Clapp |
| 2008/0159798 A1 | 7/2008 | Culp et al. |
| 2008/0182220 A1* | 7/2008 | Chishti ............... B29C 64/386 433/24 |
| 2008/0206705 A1 | 8/2008 | Kaza et al. |
| 2008/0305454 A1 | 12/2008 | Kitching et al. |
| 2008/0306724 A1 | 12/2008 | Kitching et al. |
| 2008/0308450 A1 | 12/2008 | Tchouangang |
| 2009/0061381 A1 | 3/2009 | Durbin et al. |
| 2009/0081604 A1 | 3/2009 | Fisher |
| 2009/0081611 A1 | 3/2009 | Hines et al. |
| 2009/0136893 A1 | 5/2009 | Zegarelli |
| 2009/0215003 A1 | 8/2009 | Swain et al. |
| 2010/0036682 A1 | 2/2010 | Trosien et al. |
| 2010/0068676 A1 | 3/2010 | Mason et al. |

(56) References Cited

U.S. PATENT DOCUMENTS

| | | |
|---|---|---|
| 2010/0070297 A1 | 3/2010 | Kharraz Tavakol et al. |
| 2010/0082391 A1 | 4/2010 | Soerensen et al. |
| 2010/0105011 A1 | 4/2010 | Karkar et al. |
| 2010/0145754 A1 | 6/2010 | Rahman |
| 2010/0153162 A1 | 6/2010 | Tam et al. |
| 2010/0179854 A1 | 7/2010 | Shafer et al. |
| 2010/0203466 A1 | 8/2010 | Lawrence |
| 2011/0084093 A1 | 4/2011 | Nehren et al. |
| 2011/0106557 A1 | 5/2011 | Gazula |
| 2011/0161249 A1 | 6/2011 | Whitehouse |
| 2011/0183293 A1 | 7/2011 | Tchouangang |
| 2011/0215933 A1 | 9/2011 | Darling et al. |
| 2012/0065985 A1 | 3/2012 | Royal et al. |
| 2012/0083549 A1 | 4/2012 | Kamohara et al. |
| 2012/0267811 A1 | 10/2012 | Weitzman |
| 2012/0330677 A1 | 12/2012 | Velimesis |
| 2013/0028617 A1 | 1/2013 | Fukuoka et al. |
| 2013/0035955 A1 | 2/2013 | Torres |
| 2013/0087157 A1 | 4/2013 | Hawkins et al. |
| 2013/0089828 A1 | 4/2013 | Borovinskih et al. |
| 2013/0122448 A1 | 5/2013 | Kitching |
| 2013/0215116 A1 | 8/2013 | Siddique et al. |
| 2013/0230300 A1 | 9/2013 | Saleh et al. |
| 2013/0286174 A1 | 10/2013 | Urakabe |
| 2014/0052661 A1 | 2/2014 | Shakes et al. |
| 2014/0122100 A1 | 5/2014 | Fillmore |
| 2014/0199653 A1 | 7/2014 | Kurthy |
| 2014/0249878 A1 | 9/2014 | Kaufman |
| 2014/0278679 A1 | 9/2014 | Navani et al. |
| 2014/0315153 A1 | 10/2014 | Kitching et al. |
| 2014/0330577 A1 | 11/2014 | Herman et al. |
| 2014/0356798 A1 | 12/2014 | Parker |
| 2014/0379356 A1 | 12/2014 | Sachdeva et al. |
| 2015/0010879 A1 | 1/2015 | Kurthy |
| 2015/0202025 A1 | 7/2015 | Kaza et al. |
| 2015/0205921 A1 | 7/2015 | Dick et al. |
| 2015/0220887 A1 | 8/2015 | Peres et al. |
| 2015/0238283 A1 | 8/2015 | Tanugula et al. |
| 2015/0257859 A1 | 9/2015 | Akl |
| 2015/0310387 A1 | 10/2015 | Friedman et al. |
| 2016/0012182 A1 | 1/2016 | Golay |
| 2016/0034871 A1 | 2/2016 | Vargas et al. |
| 2016/0132893 A1 | 5/2016 | Bisges et al. |
| 2016/0158627 A1 | 6/2016 | Layzell |
| 2016/0242871 A1 | 8/2016 | Morton et al. |
| 2016/0253464 A1 | 9/2016 | Balwani et al. |
| 2016/0256240 A1 | 9/2016 | Shivapuja et al. |
| 2016/0263732 A1 | 9/2016 | Lourenco et al. |
| 2016/0287198 A1 | 10/2016 | Abramovich et al. |
| 2016/0317264 A1 | 11/2016 | Derraugh et al. |
| 2017/0010252 A1 | 1/2017 | Bearup et al. |
| 2017/0020642 A1 | 1/2017 | Mah |
| 2017/0039423 A1 | 2/2017 | Cork et al. |
| 2017/0046486 A1 | 2/2017 | Cunningham |
| 2017/0156830 A1 | 6/2017 | Wallace |
| 2017/0165040 A1 | 6/2017 | Wolgin |
| 2017/0231721 A1 | 8/2017 | Akeel et al. |
| 2017/0239018 A1 | 8/2017 | Kim |
| 2017/0281313 A1 | 10/2017 | Kim |
| 2017/0300207 A1 | 10/2017 | Wen et al. |
| 2017/0340414 A1 | 11/2017 | Janzadeh et al. |
| 2017/0347953 A1 | 12/2017 | Suri et al. |
| 2017/0364637 A1 | 12/2017 | Kshepakaran et al. |
| 2017/0365025 A1 | 12/2017 | Pumphrey |
| 2018/0014914 A1 | 1/2018 | Raghavan et al. |
| 2018/0110589 A1 | 4/2018 | Gao |
| 2018/0121875 A1 | 5/2018 | Satyanarayana Rao et al. |
| 2018/0125610 A1 | 5/2018 | Carrier et al. |
| 2018/0206940 A1 | 7/2018 | Kopelman et al. |
| 2018/0228359 A1 | 8/2018 | Meyer et al. |
| 2018/0263731 A1 | 9/2018 | Pokotilov et al. |
| 2018/0263733 A1 | 9/2018 | Pokotilov et al. |
| 2018/0285801 A1 | 10/2018 | Alde et al. |
| 2018/0303580 A1 | 10/2018 | Salah et al. |
| 2018/0353073 A1 | 12/2018 | Boucher et al. |
| 2018/0368943 A1 | 12/2018 | Katzman et al. |
| 2018/0368953 A1 | 12/2018 | Katzman et al. |
| 2018/0368954 A1 | 12/2018 | Katzman et al. |
| 2019/0013098 A1 | 1/2019 | Katzman et al. |
| 2019/0019187 A1* | 1/2019 | Miller ................ G06Q 20/40 |
| 2019/0026598 A1 | 1/2019 | Salah et al. |
| 2019/0038383 A1 | 2/2019 | Webber et al. |
| 2019/0083219 A1 | 3/2019 | Sharer |
| 2019/0175303 A1 | 6/2019 | Akopov et al. |
| 2019/0223983 A1 | 7/2019 | Mah |
| 2019/0252066 A1 | 8/2019 | Katzman et al. |
| 2019/0333622 A1 | 10/2019 | Levin et al. |
| 2019/0388188 A1 | 12/2019 | Kaza et al. |
| 2020/0035353 A1 | 1/2020 | Katzman et al. |
| 2020/0066391 A1 | 2/2020 | Sachdeva et al. |
| 2020/0081413 A1 | 3/2020 | Georg et al. |
| 2020/0113650 A1 | 4/2020 | Lemchen et al. |
| 2020/0289238 A1 | 9/2020 | Levine |
| 2020/0306011 A1 | 10/2020 | Chekhonin et al. |
| 2020/0401976 A1 | 12/2020 | Nelson et al. |
| 2021/0196434 A1 | 7/2021 | Cramer et al. |
| 2022/0096206 A1* | 3/2022 | Lockhart ................ G06F 3/048 |

FOREIGN PATENT DOCUMENTS

| | | | |
|---|---|---|---|
| CN | 201370648 | 12/2009 | |
| CN | 204472650 | 7/2015 | |
| CN | 106326681 | 1/2017 | |
| EP | 0 278 626 | 8/1988 | |
| EP | 2 425 734 | 3/2012 | |
| EP | 3 595 572 | 1/2020 | |
| GB | 0 338 822 | 11/1930 | |
| JP | H556101 U | 7/1993 | |
| JP | 09-038117 | 2/1997 | |
| KR | 20100060812 | 6/2010 | |
| WO | WO-2006/118771 | 11/2006 | |
| WO | WO-2007120920 A2 * | 10/2007 | ............... A61C 7/00 |
| WO | WO-2009/085752 | 7/2009 | |
| WO | WO-2015/054746 | 4/2015 | |
| WO | WO-2019/036677 A1 | 2/2019 | |

OTHER PUBLICATIONS

Milligen et al. (Smile Direct user interface Apr. 2, 2017 youtube web capture (https://www.youtube.com/watch?v=f_Tn8PyUh9Q) (Year: 2017).

"203221-SmileCareClub" video, uploaded to YouTube on Jun. 10, 2014, https://www.youtube.com/watch?v=B43vT_1GnR0, 33 pages of screenshots.

"Affordable Clear Braces—Smile Care Club" video, uploaded to YouTube on Mar. 30, 2015, https://www.youtube.com/watch?v=Qk-VhbH1RVM, 97 pages of screenshots.

"Clear Braces . . . at Home??! Review—Before & After—Cost" video, uploaded to YouTube on Oct. 7, 2014, https://www.youtube.com/watch?v=9wrwhRTPjtk&t, 132 pages of screenshots.

"Invisalign Manufacturing Process English" video, uploaded to YouTube on Apr. 7, 2014, https://www.youtube.com/watch?v=vsR0_wTR2a8, 125 pages of screenshots.

"Smile Care Club Unboxing, Review, Tutorial" video, uploaded to YouTube on May 1, 2015, https://www.youtube.com/watch?v=p7Y5fMRnJWE, 126 pages of screenshots.

"Smile Direct Club SmileShop Visit" video, uploaded to YouTube on Nov. 2, 2016, https://www.youtube.com/watch?v=wYQdNHPJb18, 420 pages of screenshots.

"Speak Out Game—Ellen Show with Khloe Kardashian and Kevin Hart", uploaded to YouTube on Oct. 11, 2016, https://www.youtube.com/watch?v=RDILAiBFRLY, 50 pages of screenshots.

"Startup Story and Hiring Help from Smile Direct Club Founder Doug Hudson" on relode.com, published Aug. 11, 2015, available at https://www.relode.com/blog/startup-story-and-hiring-help-from-smilecareclub-founder-doug-hudson, 2 pages.

"Step 1! Working on my Smile.. Smile Care Club" video, uploaded to YouTube on Jan. 4, 2015, https://www.youtube.com/watch?v=T_F3Xt4Og7w, 87 pages of screenshots.

(56) References Cited

OTHER PUBLICATIONS

"Why I am Straightening My Teeth With SmileDirectClub", Gluesticks Blog, https://gluesticksblog.com/smiledirectclub-review/, Aug. 26, 2015, 19 pages.

Albert et al., "Smile Care Club Review—My experience straightening my teeth with smile care", https://smilecareclubreview.wordpress.com/page/1/, relevant web posts published from Jan. 9, 2015-Mar. 4, 2015, accessed online Dec. 30, 2019 (Year: 2015), 8 pages.

Align Technology, Inc., "Invisalign Outcome Simulator 4.1," 2017, https://rdentlab.com/resources/clinical-information-guides/ (50 pages).

Align Technology, Inc., "iTero Element 2 and Flex Brochure for Orthodontists," 2018, https://global.itero.com/en-gb/training/literature (6 pages).

Beers et al., "Computer-assisted treatment planning and analysis", Orthod Caniofacial Res 6(Suppl. 1), 2003; 117-125.

Bhambal et al., "Teledentistry: potentials unexplored!", J. Int Oral Health, Oct. 2010, vol. 2 (Issue 3).

Buschang et al., "Comparative Time Efficiency of Aligner Therapy and ConventionaL Edgewise Braces", Angle Orthodontist, vol. 84, No. 3, 2014, 6 pages.

Candid Care Co., https:/www.candidco.com/how-it-works/, webpage printed as existed on Sep. 2, 2018, located using the Internet Archive WayBack Machine, 10 pages.

Combined Search and Examination Report on GB 2104334.4 dated Sep. 8, 2021.

Complaint for Patent Infringement, *Smiledirectclub, LLC* v. *Candid Care Co.*, Case No. Case 1:20-cv-00583-UNA, Apr. 29, 2020, 45 pages.

Cooper et al., "Knowledge, attitudes, and confidence levels of dental hygiene students regarding teledentistry: A pilot study." The Internet Journal of Allied Health Sciences and Practice. Oct. 2007, vol. 5 No. 4.

CVS Health and Smile Direct Club Team Up to Expand Access and Affordability to Innovative Solution for Achieving A Straighter Smile (Apr. 25, 2019). PR Newswire Retrieved from https://dialog.proquest.com/professional/docview/2213815454?accountid=131444 (Year: 2019).

Decision on Appeal for U.S. Appl. No. 15/725,430, mail date Sep. 23, 2021, 11 Pages.

Defendant Candid Care Co's Opening Brief in Support of its Motion to Dismiss, *Smiledirectclub, LLC* v. *Candid Care Co.*, Case No. Case 1:20-cv-00583-CFC, Jun. 19, 2020, 147 pages.

Defendant Candid Care Co's Reply Brief in Support of its Motion to Dismiss, *Smiledirectclub, LLC* v. *Candid Care Co.*, Jul. 31, 2020, 17 pages.

Dental Review, "New Itero Element 2 and iTero Element Flex," 2018, https://www.dentalreview.news/technology/24-dental-cad-cam-technology /3 25 5-new-itero-element-2-and-itero-element-flex (4 pages).

Do It Yourself Dental Impression Kit, Apr. 30, 2016, 2 pages.

Ercoli et al., "A comparative study of two different clear aligner systems", Progress in Orthodontics, 2014.

Fabels et al., "Interexaminer and intraexaminer reliabilites of 3-dimensional orthodontic digital setups", American Journal of Orthodontics and Dentofacial Orthopedics, Dec. 2014, vol. 146, Issue 6.

Federal Circuit Affirmance on the '522 patent Case No. 2021-1446 dated Aug. 17, 2021.

Forever Aligned Club, "Straight Teeth Forever", https://www.foreveralignedclub.com/straight-teeth-forever/, May 26, 2017, 3 pages.

From Home Dental, Web page: https://web.archive.org/web/20161021220200/https://fromhomedental.com, Oct. 21, 2016, 4 Pages.

Garino et al., "The iTero Intraoral Scanner in Invisalign Treatment: A Two-year Report", JCO, Feb. 2014.

Grindguard, "How to use your dental impression kit", http://www.grindguardpm.com/support/how-to-use-your-dental-impression-kit/ Feb. 9, 2017, accessed online Jan. 3, 2020 (Year: 2017), 5 pages.

Groth et al., "Three-Dimensional Printing Technology", JCO, 2014.

Hayashi et al., "Assessment of the accuracy and reliability of new 3-dimensional scanning devices", American Journal of Orthodontics and Dentofacial Orthopedics, Oct. 2013, vol. 144, Issue 4.

Hoabie et al., "Evaluation Kit in Mail", https://smilecareclub.wordpress.com/ Mar. 27, 2015, accessed online Jan. 2, 2020 (Year: 2015), 3 pages.

International Search Report and Written Opinion for International Application No. PCT/US2018/038459, dated Oct. 22, 2018, 13 pages.

International Search Report and Written Opinion for International Application No. PCT/US2019/054958, dated Dec. 17, 2019, 8 pages.

International Search Report in International Patent Application PCT/US2018/065133 dated Apr. 22, 2019 (2 pages).

ITero Element Orthodontic Patient Video, Uploaded to YouTube Apr. 4, 2016, https://www.youtube.com/watch?v=Ca69CuWqHCw, 33 pages of screenshots.

Jain et al., "Teledentistry: Upcoming Trend in Dentistry", J Adv Med Dent Scie 2013; 1(2): 112-115.

James Hunt; SmileDirectClub impression kit, https://www.youtube.com/watch?v=3u2K19Mphey, uploaded Jan. 16, 2017, 19 pages of screenshots.

Jampani et al., "Applications of teledentistry: A literature review and update", Journal of Int Society of Preventive & Community Dentistry, Jul.-Dec. 2011; 1(2): 37-44.

Jones, Perry "The iTero optical scanner for use with Invisalign: A descriptive review", ineedce.com, Feb. 2012.

Kravitz et al. (Teledentistry, Do-It-Yourself Orthodontics, and Remote Treatment Monitoring-JCO/December 2016—vol. L No. 12) (Year: 2016).

Kravitz et al., "Intraoral Digital Scanners", JCO, 2014, vol. 48, No. 6.

Kravitz et al., "Teledentistry, Do-It-Yourself Orthodontics, and Remove Treatment Monitoring", JCO, Dec. 2016, 9 pages.

Kuncio, Daniel A. "Invisalign: Current guidelines for Effective Treatment", NY State Dental Journal, Mar. 2014.

Lau et al., "Computerised Imaging, Virtual Treatment Planning and Orthodontic Treatment of Dental Malocclusions Using the Invisalign Appliance", The Hong Kong Medical Diary, vol. 9, No. 10, Oct. 2004.

Lin et al., "3D CAD for Design of Invisible Tooth Aligner", Proceedings of the 2005 IEEE Int Conf on Mechanics, Jul. 10-12, Taipei, Taiwan.

Martin et al., "Orthodontic scanners: what's available?", Journal of Orthodontics, vol. 000, 2014, 000-000.

Martorelli et al., "A comparison between customized clear and removable orthodontic appliances manufactured using RP and CNC techniques", Elsevier, Dental Materials 29 (2013).

Memorandum Opinion, *Smiledirectclub, LLC* v. *Candid Care Co.*, Case 1:20-cv-00583-CFC, Dec. 7, 2020, 25 pages.

Monika et al., "Teledentistry: An Overview." J Adv Med Dent Scie Res 2015;3(2):88-91.

Mouthpiece Guy et al.: "*Mouthpiece Guy* vs. *The Competition*: Impression Kits", www.youtube.com/watch?v=tYOjMtYWQOQ&feature=youtu.be, Feb. 23, 2018, 20 pages of screenshots.

Nelson, Brandy et al. (Why I am Straightening My Teeth with SmileDirectClub—Gluesticks Blog—https://gluesticksblog.com/smiledirectclub-review/) (Year: 2015).

Notice of Appeal, *Smiledirectclub, LLC* v. *Candid Care Co.*, Case 1:20-cv-00583-CFC, Dec. 8, 2020, 2 pages.

Relode, "Startup Story and Hiring Help from SmileDirect Club Founder Doug Hudson"; https://www.relode.com/blog/startup-story-and-hiring-help-from-smiledirectclub-founder-doug-hudson, Aug. 11, 2015, 3 pages.

Shailee et al., "Teledentistry the future of dental practice", Indian J Dent Adv 2013; 5(2): 1195-1199.

Smile Care Club Review, URL: https://www.youtube.com/watch?v=jpAjhJqi6vc, Mar. 26, 2016, 260 pages of screenshots.

Smile Care Club, "Impression Kit", Jul. 21, 2014, available for retrieval at URL https://vimeo.com/wmvproductions/review/115725718/28854a7f49, 43 pages of screenshots.

(56) References Cited

OTHER PUBLICATIONS

Smile Care Club, "Impressions—New Box", 2015, available for retrieval at URL https://vimeo.com/wmvproductions/review/137176701/d45be82d56, 24 pages of screenshots.
Smile Care Club, "Impressions—Old Box", 2015, available for retrieval at URL https://vimeo.com/wmvproductions/review/137176599/0b8020929d, 21 pages of screenshots.
Smile Care Club, "Impressions ReEdit", 2016, available for retrieval at URL https://vimeo.com/wmvproductions/review/168249998/0b75310374, 32 pages of screenshots.
Smile Care Club, "Impressions", 2015, available for retrieval at URL https://vimeo.com/wmvproductions/review/136533463/1a8515abf5, 10 pages of screenshots.
Smile Care Club, "Making Dental Impressions" video, Mar. 2016, 74 pages of screenshots.
Smile Care Club, "Promo", 2014, available for retrieval at URL https://vimeo.com/wmvproductions/review/115725719/9c8235cdf2, 25 pages of screenshots.
Smile Direct Club "smile evaluation kit instruction guide" https://s3.amazonaws.com/static.smiledirectclub.com/evaluation_kit_instructions_5_2_16_email .pdf.
Smile Direct Club Impression Guide (available online Nov. 14, 2016, https://www.sharperimage.com/si/pdf/manuals/203221.pdf accessed Sep. 3, 2019 (Year: 2016), 24 pages.
Smile Direct Club Vimeo online video uploaded publicly on Mar. 2, 2016 (https://vimeo.com/157450883, pdf attachment of screen captures published online (Year: 2016) accessed and recorded on Dec. 13, 2018.
SmileCareClub promo video uploaded on Jun. 6, 2014 https://www.youtube.com/watch?v=h7x8BwWXUsk, 33 pages of screenshots.
Smiledirectclub, "What's a Smile Shop?", https://blog.smiledirectclub.com/what-is-smiledirectclub-smileshop/ Apr. 6, 2017, 7 pages.
Smiledirectclub, LLC's Opposition to Candid Care Co.'s Motion to Dismiss, *Smiledirectclub, LLC* v. *Candid Care Co.*, Case No. Case 1:20-cv-00583-CFC, Jul. 17, 2020, 29 pages.
Smiledirectclub; Frequent Questions https://web.archive.org/web/20170409175711/https://smiledirectclub.com/faq/ Apr. 9, 2017, 7 pages.
Snapcorrect, "What Does My Impression Evaluation Kit Include", https://support.snapcorrect.com/support/solutions/articles/32000019500-what-does-my-impression-evaluation-kit-include, Sep. 18, 2017 1 page.
Snapcorrect, "What Does the 'Return by' Sticker Date Mean", https://support.snapcorrect.com/support/solutions/articles/32000022084-what-does-the-return-by-sticker-date-mean, Feb. 5, 2018 1 page.
Snapcorrect, Snap Correct Impressions, https://www.youtube.com/watch?v=yywqIDSabew, uploaded Oct. 6, 2017, 6 pages of screenshots.
Snapcorrect, SnapCorrect Truly Invisible Aligners, https://youtube.com/watch?v=yywqIDSabew, uploaded Jul. 27, 2017, 8 pages of screenshots.
Summerfelt, Fred F. "Teledentistry-Assisted, Affiliated Practice for Dental Hygienists: An Innovative Oral Health Workforce Model", Journal of Dental Education, 2011.
Summerfelt, Fred F., "Teledentistry-Assisted, Affiliated Practice for Dental Hygienists: An Innovative Oral Health Workforce Model", Journal of Dental Education, vol. 75, No. 6, Jun. 2011, pp. 733-742.
SwankySmiles advertisement from Feb. 8, 2019, located at www.swankysmiles.com, 5 pages of screenshots.
Szuhanek et al., "Application of Thermoplastic Materials in the Fabrication of Orthodontic Aligners", Materiale Plastice, 52, No. 3, 2015.
Szuhanek et al., "The Role of Digital Setup in the Orthodontic Treatment with Plastic Aligners", Materiale Plastice, 52, No. 4, 2015.
Taneva et al., "3D Scanning, Imaging, and Printing in Orthodontics", IntechOpen, 2015.
Thukral et al., "Invisalign: Invisible Orthodontic Treatment—A Review." J Adv Med Dent Scie Res 2015;3(5):S42-S44.
Evaluation Kit Instruction Guide; https://s3.amazonaws.com/static.smiledirectclub.com/evaluation_kit_instructions_5_2_16 _email.pdf.
Smile Direct Club-Don't Make These 7 Mistakes on your photo assessment (httos://smiledirectclub.com/blog/dont-make-these-7- mistakes-on-your-photo-assessment/) accessed 2020, published originally 2016 (Year: 2016).

\* cited by examiner

CASES

| CASE # — 204 | NAME — 206 | CREATION DATE — 208 | STATUS — 230 |
|---|---|---|---|
| C7ac1h0f5d4a | PATIENT 1 | DEC 28, 2020 | ○ WAITING ON ALIGNER PURCHASE |
| Cc966e65ce434a | PATIENT 2 | DEC 22, 2020 | ○ WAITING ON ALIGNER PURCHASE |
| C7cca00de87928 | PATIENT 3 | DEC 21, 2020 | ○ IMPRESSIONS SENT TO SDC LAB |
| C9cdc501b2c0a | PATIENT 4 | DEC 21, 2020 | ○ WAITING ON ALIGNER PURCHASE |
| C10669f721c831 | PATIENT 5 | DEC 19, 2020 | ○ WAITING ON ALIGNER PURCHASE |
| C42ef7caba06e | PATIENT 6 | DEC 19, 2020 | ○ NEEDS CLEARANCE |
| C984443a3c4df9 | PATIENT 7 | DEC 19, 2020 | ○ WAITING ON ALIGNER PURCHASE |
| C54c7545240992 | PATIENT 8 | DEC 18, 2020 | ○ NEEDS CLEARANCE |
| Ca216155bh8cb8 | PATIENT 9 | DEC 18, 2020 | ○ NEEDS CLEARANCE |
| Ca1848a2085ab9d | PATIENT 10 | DEC 17, 2020 | ○ WAITING ON ALIGNER PURCHASE |

SHOWING 1-10 of 52

NEW CASE

FIG. 2

DOES PATIENT HAVE ANY OF THE FOLLOWING?
SELECT ALL THAT APPLY
- ☐ BONDED RETAINER
- ☐ BRIDGEWORK
- ☐ CROWNS
- ☐ IMPACTED TOOTH
- ☐ IMPLANT
- ☐ PRIMARY TEETH
- ☐ VENEERS

SELECT ALL THAT APPLY TO PATIENT.
- ☐ RECENT RADIOGRAPH TAKEN OF TEETH
- ☐ CURRENTLY HAVE PAIN IN ANY TEETH
- ☐ SORES OR LUMPS IN OR NEAR MOUTH
- ☐ INDICATION OF A SERIOUS DENTAL ISSUE IDENTIFIED BY A DENTIST WITHIN THE LAST 6 MONTHS?
- ☐ EXISTING HEAD, NECK, OR JAW INJURIES.
- ☐ JAW CLICKING, PAIN, OR DIFFICULTY OPENING, CLOSING, OR CHEWING.
- ☐ FEEL LOOSENING OF TEETH OR HAVE UNTREATED PERIODONTAL DISEASE
- ☐ KNOWN ALLERGIES TO ANY DENTAL MATERIALS
- ☐ HISTORY OF IV BISPHOSPHENATE TREATMENT
- ☐ CURRENTLY ON ACUTE CARTICOSTEROIDS OR IN AMMUNSUPPRESSION, CHEMOTHERAPY, OR RADIATION OF HEAD/NECK
- ☐ HAD BONE MARROW TRANSPLANT OR TREATMENT OF HARMATOLOGICAL MALIGNANCIES (BLOOD CANCERS) WITHIN THE POST 2 YEARS

PATIENT CONSENT
- ☑ I AGREE TO SMILEDIRECTCLUB'S INFORMED CONSENT, TERMS AND SMILEPAY CONDITIONS

BACK  CONTINUE

FIG. 4

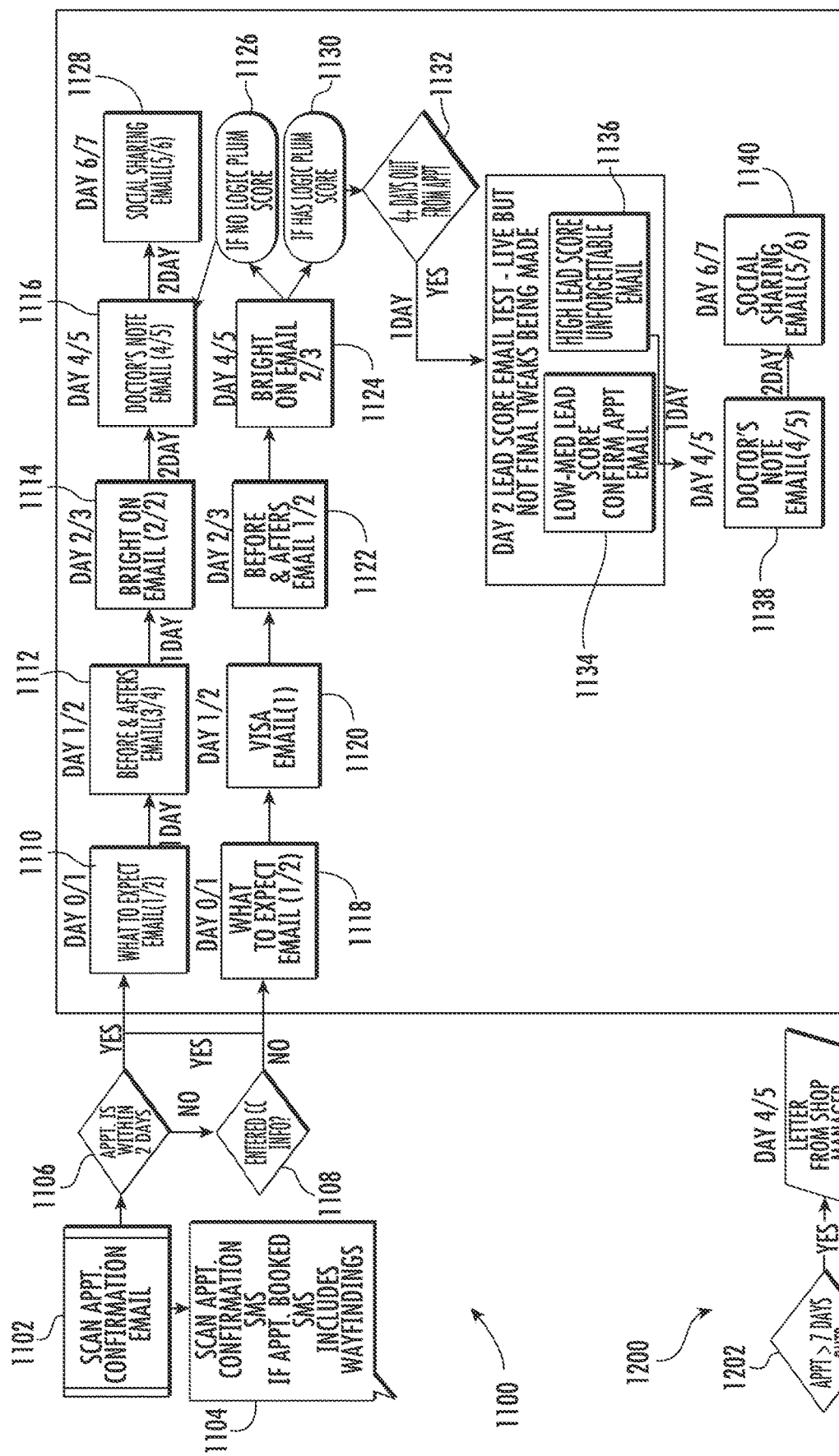

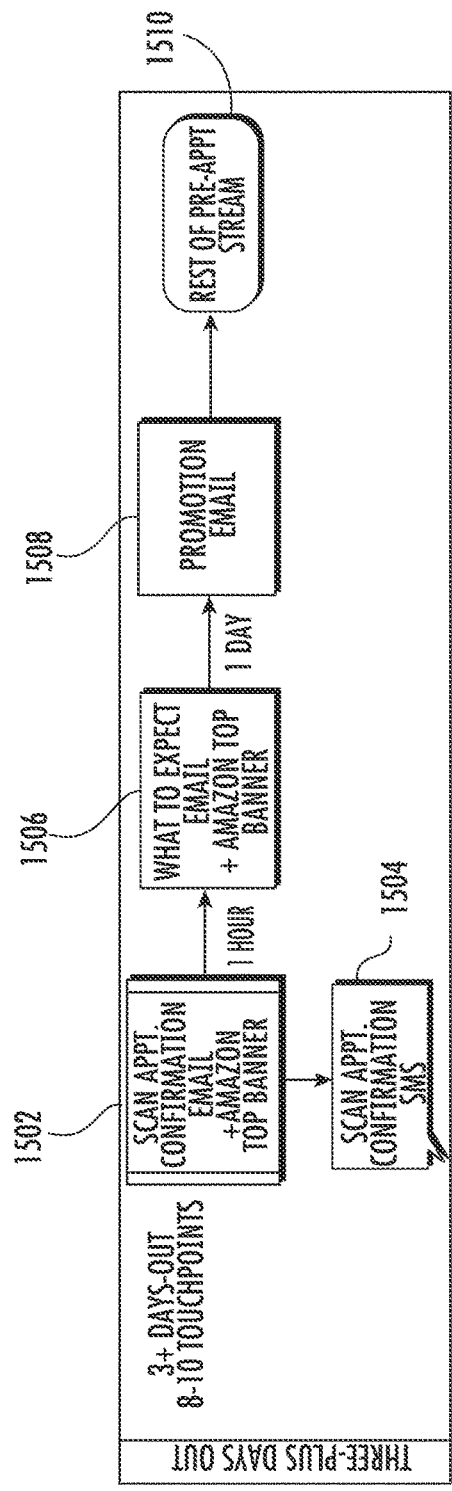
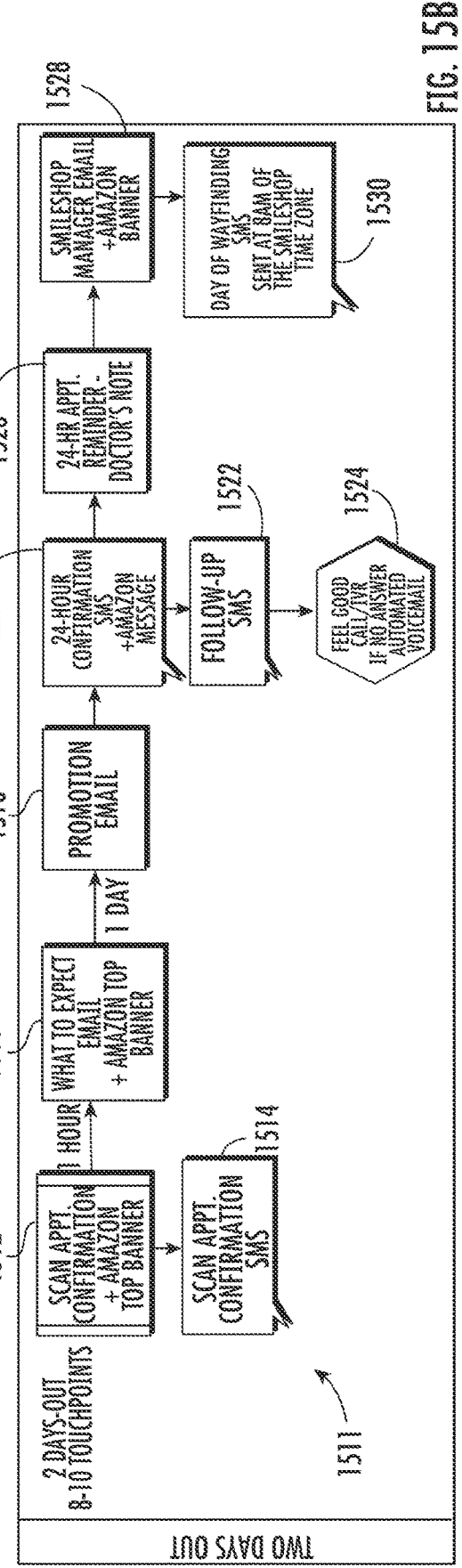
FIG. 15A
FIG. 15B

DISTRIBUTED SYSTEM FOR FABRICATING DENTAL ALIGNERS

CROSS-REFERENCE TO RELATED APPLICATIONS

This application is a continuation of U.S. patent application Ser. No. 17/148,437, filed Jan. 13, 2021, which is a continuation-in-part of U.S. patent application Ser. No. 17/247,296, filed Dec. 7, 2020, now U.S. Pat. No. 11,094,414, which is a continuation of U.S. patent application Ser. No. 16/859,950, filed Apr. 27, 2020, now U.S. Pat. No. 10,861,599, which is a continuation of U.S. patent application Ser. No. 16/130,762, filed Sep. 13, 2018, now U.S. Pat. No. 10,636,522, which claims the benefit of and priority to U.S. Provisional Application No. 62/660,141, filed Apr. 19, 2018. U.S. patent application Ser. No. 16/130,762 is also a continuation-in-part of U.S. patent application Ser. No. 15/725,430, filed Oct. 5, 2017, which claims the benefit of and priority to U.S. Provisional Application No. 62/522,847, filed Jun. 21, 2017. U.S. patent application Ser. No. 17/148,437 is also a continuation-in-part of U.S. patent application Ser. No. 15/725,430, filed Oct. 5, 2017, which claims the benefit of and priority to U.S. Provisional Application No. 62/522,847, filed Jun. 21, 2017. The contents of each of these applications are incorporated herein by reference in their entirety.

TECHNICAL FIELD

The present disclosure relates generally to the field of dental imaging and treatment, and more specifically, to a central processing system and related methods for conducting a scan to obtain three-dimensional images of a patient's teeth and fabricating dental aligners for repositioning the patient's teeth.

BACKGROUND

Dental impressions and associated physical or digital reproductions of a patient's teeth can be used by dentists or orthodontists to diagnose or treat an oral condition, such as the misalignment of the patient's teeth. Typically, to receive treatment for a misalignment, a patient visits a dentist that specializes in such treatment. The patient may visit the dentist for an initial consultation, a first appointment where the patient actually begins treatment, and numerous follow-up appointments, each with the same dentist. This form of treatment can be costly, both from a time and financial perspective. For example, it may be burdensome for a patient to attend each of the appointments, particularly where the dentist's office is located far away from the patient. Additionally, the financial cost of such orthodontic treatment can vary geographically, as dentists in certain geographic areas (e.g., larger cities) may charge more per office visit and more for orthodontic treatment, due to cost of living being greater.

SUMMARY

According to one aspect of the disclosure, a method of fabricating aligners for repositioning one or more teeth of a patient is disclosed. The method includes conducting, using an intraoral scanner, an intraoral scan at an intraoral scanning site, the intraoral scan generating three-dimensional data of the mouth of the patient. The intraoral scanning site is located in an office of an intake dentist or orthodontist. The patient physically sees the intake dentist or orthodontist at the office. The method includes causing generation of, by a treatment plan computing system located at a treatment plan site separate from the intraoral scanning site without the patient being present at the treatment plan site, the treatment plan for the patient based on the three-dimensional data. The method includes receiving an indication of an approval of the treatment plan by an approving dentist or orthodontist. The approving dentist or orthodontist is different from the intake dentist or orthodontist. The approval is received without the approving dentist or orthodontist having physically seen the patient. The method includes receiving, by a fabrication computing device located at a fabrication site separate from the intraoral scanning site and the treatment plan site without the patient or the dentists or orthodontists being present at the fabrication site, the treatment plan from the treatment plan computing system. The method includes fabricating, at the fabrication site, a plurality of aligners based on the treatment plan. The plurality of aligners are specific to the patient and are configured to reposition one or more teeth of the patient in accordance with the treatment plan. The method includes sending the plurality of aligners to the patient without first providing the plurality of aligners to the intake dentist or orthodontist. The patient receives orthodontic treatment without ever having physically seen the approving dentist or orthodontist. The method includes providing, by a patient intake portal, a plurality of status updates to the intake dentist or orthodontist regarding a status of the patient. The plurality of status updates includes a treatment underway status indicating at least one of the patient is scheduled to receive the dental aligners, the patient has received the dental aligners, or that dental aligners have been sent to the patient.

According to another aspect, a distributed system is disclosed. The distributed system includes a central processing system and a dental aligner fabrication system. The central processing system includes one or more servers. The central processing system is communicably coupled to a plurality of computing devices that are located separate and remote from one another. The one or more servers include one or more processors configured by machine-readable instructions to provide the plurality of computing devices access to a plurality of portals of the central processing system. The plurality of portals include a patient intake portal configured to be accessed by a first computing device located at an office of a first dentist or orthodontist. The patient intake portal is configured to receive patient intake data and data regarding a three-dimensional (3D) representation of a mouth of a patient obtained during a scheduled appointment at the office. The plurality of portals include a treatment plan portal configured to be accessed by a second computing device separate and remote from the first computing device. The treatment plan portal is configured to provide the second computing device access to a 3D model of the mouth of the patient. The 3D model is generated based on the 3D representation. The treatment plan portal is configured to receive treatment plan data generated by the second computing device based on the 3D model. The plurality of portals include an approving dental portal configured to be accessed by a third computing device separate and remote from the first computing device and the second computing device and corresponding to a second dentist or orthodontist. The approving dental portal is configured to provide the third computing device access to the treatment plan data. The approving dental portal is configured to receive a command from the third computing device that indicates an approval status of the treatment plan. The dental aligner fabrication system includes a fabrication computing device configured to receive the treatment plan data responsive to the approving dental portal receiving the command indicating the approval status of the treatment plan. The dental aligner fabrication system includes dental aligner fabrication equipment configured to fabricate one or more dental aligners based on the treatment plan data. The one or more dental aligners are specific to the patient and are configured to reposition one or more teeth of the patient in accordance with the treatment plan generated for the patient.

According to another aspect, a system is disclosed. The system includes a management engine configured to maintain patient files corresponding to a plurality of patients. Each patient file includes a status maintained by the management engine that is updated based on a progression of the patient from patient intake to undergoing treatment via dental aligners. The system includes a patient intake portal configured to be accessed by a first computing device located at an office of an intake dentist or orthodontist that is to obtain a three-dimensional (3D) representation of a mouth of a patient during a scheduled appointment at the office. The patient intake portal is configured to: generate and provide a user interface to the first computing device. The user interface indicates the status of patient files for each case of a plurality of cases generated via the patient intake portal at the office. The plurality of cases correspond with a plurality of patients. The plurality of patients include the patient. The patient intake portal is configured to generate a new case corresponding to the patient. Generating the new case includes receiving an indication from the first computing device. The indication indicates that data from the three-dimensional (3D) representation of the mouth will be provided for the patient for generating one or more dental aligners for the patient. Generating the new case includes receiving intake data from the first computing device corresponding to the patient, including dental history information and one or more photographs of the patient's teeth. The patient intake portal is configured to generate and provide an updated user interface to the first computing device, the updated user interface including the new case. The management engine is further configured to generate a patient file for the patient using the intake data received from the first computing device via the patient intake portal, where the patient file has a status, and the updated user interface indicates the status of the new case.

According to another aspect, a system is disclosed. The system includes one or more servers communicably coupled to a plurality of computing devices associated with a plurality of offices. The one or more servers comprise one or more processors configured by machine-readable instructions to provide a management engine. The management engine is configured to determine, based on data received from the plurality of computing devices, one or more factors for each of the plurality of offices. The management engine is configured to compute a rating for each office based on the one or more factors. The management engine is configured to receive, from a patient computing device, a request for an appointment for obtaining a three-dimensional (3D) representation of a mouth of a patient within a geographic area. The management engine is configured to identify, based on the request, a subset of the plurality of offices that are within the geographic area. The management engine is configured to generate a user interface for the patient that identifies the subset of the plurality of offices in an order based on a relative rating of the offices from the subset.

Various other embodiments and aspects of the disclosure will become apparent based on the drawings and detailed description of the following disclosure.

BRIEF DESCRIPTION OF THE DRAWINGS

FIG. 2 shows a user interface relating to a case review page of a patient intake portal of the system of FIG. 1, according to an illustrative embodiment.

FIG. 4 shows a user interface of the patient intake portal of FIG. 1 for inputting dental history information and consent information, according to an illustrative embodiment.

FIG. 11 is a flowchart showing a first messaging process for messaging a patient prior to a scheduled appointment, according to an illustrative embodiment.

FIG. 12 is a flowchart showing a method of providing a personalized notification to a patient before a scheduled appointment, according to an illustrative embodiment.

FIGS. 15A-D are flowcharts showing methods of providing multiple notifications to patients based on when the patient schedules their appointment, according to illustrative embodiments.

DETAILED DESCRIPTION

Figure 1:
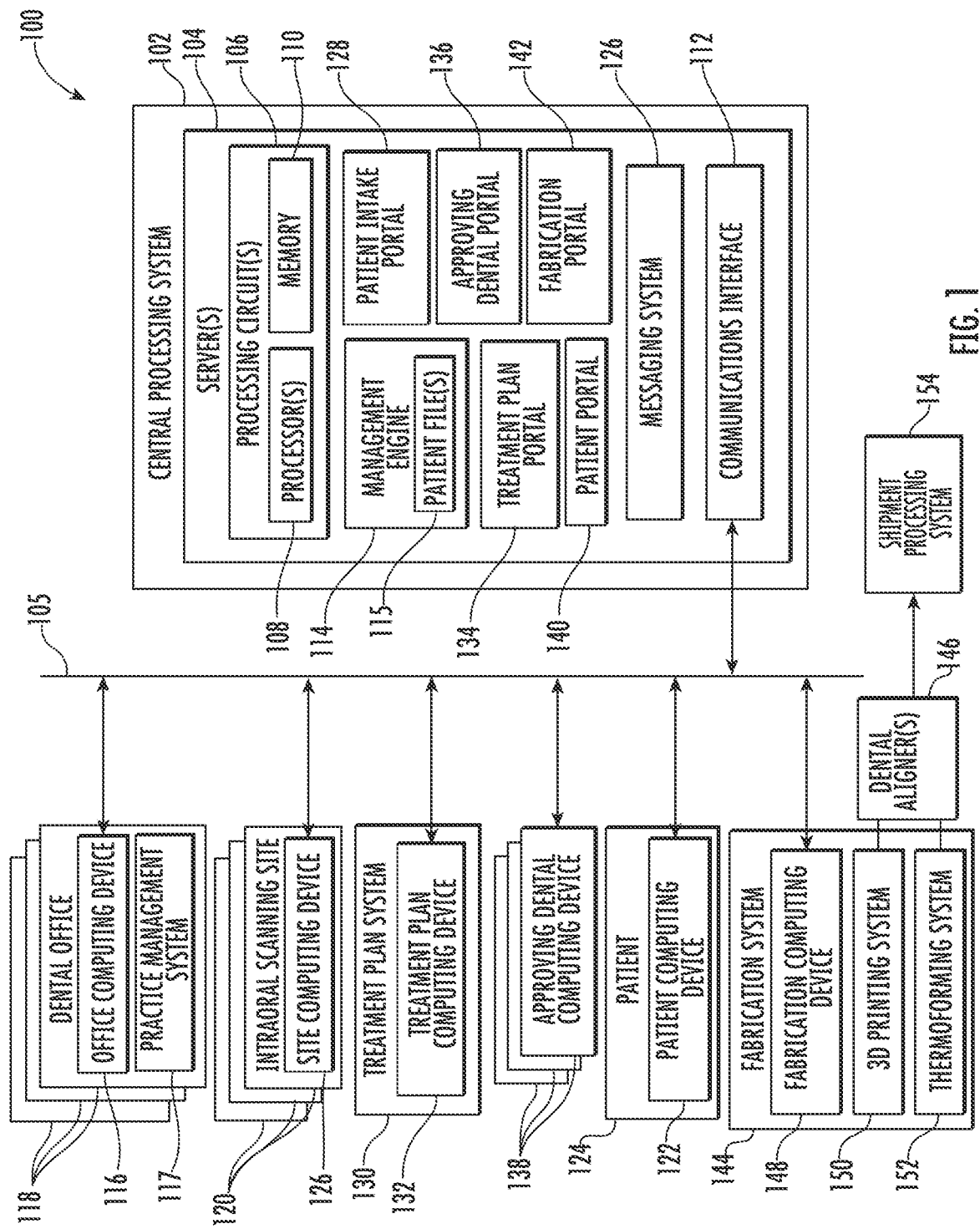
FIG. 1 shows a system for fabricating dental aligners, according to an illustrative embodiment.

The present disclosure is directed to a distributed system and methods for fabricating dental aligners. A patient can request an appointment at a dental office, which may have a dedicated intraoral scanning area, a pop-up scanning site, or an area for administering impressions. For example, the patient can request an appointment in advance of the requested appointment time (e.g., online, via a mobile application, via a telephone call) with the dental office directly, or via an application or other web-based portal associated with a dental aligner manufacturer. At the scheduled appointment, the dental office may capture data corresponding to the patient's dentition (e.g., either through an intraoral scan at the dental office or via impressions administered at the dental office). A dental professional at the dental office may operate an office computing device to establish a connection with a patient intake portal of a central processing system. As used herein, a dental professional refers to a dentist or an orthodontist, where a dentist is a professional who is skilled and licensed to practice in the prevention, diagnosis, and treatment of diseases, injuries, and malformations of the teeth, gums, and jaws, and an orthodontist is a dentist which specializes in dealing with irregularities of the teeth (such as malocclusions), and their correction. The dental professional may control the office computing device to generate a new patient file for the patient (e.g., which is generated and maintained by a management engine of the central processing system). The office computing device may upload, transmit, or otherwise provide the data corresponding to the patient's dentition (along with other patient intake data) to the management engine using the patient intake portal. The management engine may populate the patient file using the data received from the office computing device. The management engine may provision or otherwise provide data corresponding to the patient file to other computing devices which are separate from the dental office, such as an approving dental computing device for an approving dentist or orthodontist (which is different from the dental professional at the dental office) to approve the patient as being fit for treatment, a treatment plan computing device for generating a treatment plan, and a fabrication computing device for fabricating dental aligners.

The systems and methods described herein may have many benefits over existing computing systems. For example, by providing a central processing system which interfaces with separate computing devices, each computing device may use less processing resources. Additionally, such implementations distribute tasks across a plurality of computing devices, which may increase speeds for patient intake, treatment plan generation, and dental aligner fabrication. Furthermore, by offloading patient file management to the management engine, patient file data may be selectively provided to particular computing devices via the respective portals described herein. Such embodiments may increase security of the patient file by ensuring sensitive patient file information is not provided to a party which should not have access to such information. Additionally, such embodiments declutter each of the computing devices, both in terms of memory by limiting data which is to be downloaded in retrieving patient file data, and in terms of user interfaces at the computing devices by ensuring the user interfaces only display information pertinent to a particular task to be performed by or via the respective computing device. Various other technical benefits and advantages are described in greater detail below.

Referring to FIG. 1, a distributed system 100 for fabricating dental aligners is shown, according to an illustrative embodiment. The distributed system 100 is shown to include a central processing system 102. The central processing system 102 may be or include one or more servers 104 which are communicably coupled to a plurality of computing devices. In some embodiments, the central processing system 102 may include a plurality of servers 104, which may be located at a common location (e.g., a server bank) or may be distributed across a plurality of locations. The central processing system 102 may be communicably coupled to the computing devices via a communications link or network 105 (which may be or include various network connections upon which communicate, transmit, receive, or otherwise exchange data between addresses corresponding to the computing devices and/or central processing system 102). The network 105 may be a Local Area Network (LAN), a Wide Area Network (WAN), a Wireless Local Area Network (WLAN), an Internet Area Network (IAN) or cloud-based network, etc. The network 105 may facilitate communication between the respective components of the system 100, as described in greater detail below.

The central processing system 102 includes one or more processing circuits 106, which may include a processor 108 and memory 110. Processor 108 may be a general purpose or specific purpose processor, an application specific integrated circuit (ASIC), one or more field programmable gate arrays (FPGAs), a group of processing components, or other suitable processing components. Processor 108 may be configured to execute computer code or instructions stored in memory 110 or received from other computer readable media (e.g., CDROM, network storage, a remote server, etc.) to perform one or more of the processes described herein. Memory 110 may include one or more data storage devices (e.g., memory units, memory devices, computer-readable storage media, etc.) configured to store data, computer code, executable instructions, or other forms of computer-readable information. Memory 110 may include random access memory (RAM), read-only memory (ROM), hard drive storage, temporary storage, non-volatile memory, flash memory, optical memory, or any other suitable memory for storing software objects and/or computer instructions. Memory 110 may include database components, object code components, script components, or any other type of information structure for supporting the various activities and information structures described in the present disclosure. Memory 110 may be communicably connected to processor 108 via processing circuit 106 and may include computer code for executing (e.g., by processor 108, etc.) one or more of the processes described herein.

The central processing system 102 is shown to include a communications interface 112. The communications interface 112 can be or include components configured to transmit and/or receive data from one or more remote sources (such as the computing devices described herein). In some embodiments, each of the servers 104 and computing devices may include a respective communications interface 112 which permit exchange of data between the respective components of the system 100. As such, each of the respective communications interfaces 112 may permit or otherwise enable data to be exchanged between the computing devices and/or the computing system 102. In some implementations, the communications device(s) 114 may access the network 105 to exchange data with various other communications device(s) 114 via cellular access, a modem, broadband, Wi-Fi, satellite access, etc.

The server(s) 104 are shown to include a management engine 114. The management engine 114 may be any device(s), component(s), circuit(s), or other combination of hardware and/or software designed or implemented to manage enrollment of dental offices with the central processing system 102. As described in greater detail below, an office computing device 116 of a dental office 118 may be enrolled with the central processing system 102 via the management engine 114. Responsive to enrollment, the office computing device 116 may be configured to access one or more portals of the central processing system 102 such that the dental office 118 is incorporated into a network of providers including other enrolled dental offices 118 and intraoral scanning sites 120. The intraoral scanning sites 120 may be similar to the intraoral scanning sites described in U.S. patent application Ser. No. 16/130,762, titled "Arrangements for Intraoral Scanning," and filed Sep. 13, 2018, the contents of such application are incorporated herein by reference in its entirety.

The server(s) 104 are shown to include a plurality of portals. Each of the portals described herein may be or include a webpage, website, or other resource on the server 104 which is accessible by a respective computing device. In some embodiments, each computing device may be configured to access a particular portal (for instance, a dedicated portal for the particular computing device). For example, a first computing device may be configured to access a first portal, a second computing device may be configured to access a second portal, and so forth. The portals may be used by the respective computing devices for accessing particular information of the central processing system 102, for uploading or downloading data to and/or from the respective portal, and so forth. While shown as being implemented, established, or otherwise embodied on a single server 104, it is noted that some portals may be embodied on separate portals. For instance, a first portal may be embodied on a first server, a second portal may be embodied on a second server, etc. The portals may provide distributed access to computing devices for particular information corresponding to a particular patient to be treated with dental aligners.

Enrollment of Dental Offices

In some instances, a dentist, orthodontist, or other dental office manager may seek to enroll a particular dental office 118 within a network of dental providers corresponding to the dental aligner manufacturer. For example, the dental office manager may contact the dental aligner manufacturer to seek enrollment. The dental office manager may be prompted to establish log-in credentials corresponding to a patient intake portal 128, as described in greater detail below.

As shown in FIG. 1, the system 100 includes a plurality of office computing devices 116. Each of the office computing devices 116 may be located at a respective dental office 118. The office computing devices 116 may be or include a tablet which is provided by the dental aligner manufacturer responsive to enrollment of the dental office 118 within a network of providers. In other embodiments, the office computing devices 116 may be or include a desktop, a laptop, a mobile device, and so forth. The office computing devices 116 may be operated by a dental professional or office administrator enrolled with the central processing system 102. The office computing devices 116 may be operated by a dental professional to access a patient intake portal 128 for patient intake.

In some embodiments, responsive to enrollment, the office computing device 116 and/or the management engine 114 may be configured to interface with a practice management system 117 for the dental office 118. For example, the management engine 114 may be configured to interface with the practice management system 117 for the dental office 118 via an application programming interface ("API") for the practice management system 117. The management engine 114 may be configured to access a schedule for the dental office 118 by writing or otherwise transmitting one or more commands to the API for the practice management system 117. The management engine 114 may be configured to add appointments to the schedule for the dental office using the API. As such, a new patient may schedule an appointment at the dental office 118 by accessing a website or other page (or the patient portal 140) via a patient computing device 122 corresponding to the management engine 114 (rather than scheduling directly with the dental office 118).

In some embodiments, the management engine 114 may be configured to compute or otherwise determine one or more rankings or classifications for the dental offices 118 which are enrolled with the central processing system 102. The management engine 114 may be configured to compute rankings or classifications based on a number of factors including, for example, a number of daily patient visits, a practice size (e.g., total number of patients), a number of patients which receive intraoral scans, a number of patients which purchase dental aligners, and so forth. The management engine 114 may be configured to maintain data corresponding to each dental office 118 using data received via the practice management system 117 (or data received directly from the dental office 118 at enrollment or at various intervals following enrollment). The management engine 114 may include or otherwise access one or more formulas for computing a ranking for a dental office 118. The management engine 114 may be configured to apply the one or more formulas to the data for each dental office 118 to compute a ranking for each dental office 118. In some embodiments, the rankings or classifications may be relative to other dental offices 118 (e.g., globally, state-wide, by region, etc.). The management engine 114 may be configured to update rankings or classifications for the dental offices 118 as additional data is received or otherwise ingested by the management engine 114. The management engine 114 may be configured to route or otherwise direct patients which are located within a predetermined proximity from an enrolled dental office 118, as described in greater detail below.

In some embodiments, such as where a patient is located within a predetermined proximity of a plurality of enrolled dental offices 118, the management engine 114 may be configured to refer the patient to a dental office 118 based on the computed ranking for the dental office 118. For example, the management engine 114 may be configured to compute a dynamic ranking for the plurality of dental offices 118 based on the factors described above along with one or more patient-specific factors. For example, the management engine 114 may be configured to determine a distance between the patient (e.g., based on a GPS signal or IP address from a patient computing device 122, based on a received address from the patient, etc.) and the dental offices 118. The management engine 114 may be configured to apply the determined distances as a weighted factor to the computed rankings or classifications for the dental offices 118. The management engine 114 may be configured to refer the patient to a particular dental office 118 based on the dynamic ranking of the dental office 118. As such, in some instances, where two dental offices 118 have a common or similar ranking, the management engine 114 may be configured to refer the patient to the dental office 118 which is in a closer proximity to the patient. However, where two dental offices 118 have a different ranking, the management engine 114 may be configured to refer the patient to a dental office 118 which has a higher ranking, depending on how much farther away the dental office 118 is located from the patient. For instance, where a first dental office located 10 miles away from the patient has a first ranking and a second dental office located 15 miles away from the patient has a second ranking which is higher than the ranking of the first dental office, the management engine 114 may refer the patient to the second dental office. However, if the second dental office were located 25 miles away, the management engine 114 may refer the patient to the first dental office. As such, the rankings or classifications may be dynamically computed by the management engine 114 to factor both a likelihood of the patient purchasing dental aligners and convenience to the patient.

Appointment Management

Referring still to FIG. 1, the management engine 114 may be configured to receive, identify, or otherwise register one or more leads for patients who may be candidates for orthodontic treatment via dental aligners. In some embodiments, leads may be identified based on a predetermined radius (or "geofence") between the patient and one or more dental offices which are in network for receiving an intraoral scan. In some embodiments, leads may be identified based on a predetermined geofence between the patient and one or more intraoral scanning sites. In some embodiments, leads may be identified based on a combination of a predetermined geofence and a patient having self-administered dental impressions rejected or a retake dental impression kit sent to the patient, or a treatment plan which was generated for the patient having expired (e.g., following a predetermined duration, such as a number of months or years, from generation of a treatment plan without the patient initiating treatment via the dental aligners).

In some embodiments, and as described in greater detail below with respect to the messaging system 126, advertising may be used to indicate the availability appointments for an intraoral scan in a given area to various potential patients. For example, in some arrangements, advertising may be used on a social media platform according to geofencing to identify potential patients within a certain distance of the scheduled location of the a dental office 118 and/or intraoral scanning site 120 (e.g., based on information input by the patient into the social media platform, based on the patient's location determined by the social media platform from the patient's IP address, based on the patient's location determined by an application associated with the social media platform running on a mobile device associated with the patient from a global positioning system ("GPS") on the mobile device). The social media platform may then provide advertisements to potential patients on the social media platform who are within the geofence (e.g., a forty mile radius from the dental office 118 or a smaller radius if there is a nearby intraoral scanning site 120). Various examples of notifications and advertisements are described in greater detail below. The advertisements may also be tailored to certain demographics (e.g., individuals 18-65). Further, in certain arrangements, additional factors may be used to advertise to potential patients on the social media platform who are more likely to schedule an appointment with the dental office 118, such as potential patients within the geofence that the social media platform has determined are above a certain income level or that the social media platform has determined have similar demographics to others that have clicked on the advertisement in the past. In some embodiments, the management engine 114 may interface with the social media platform (e.g., using an API of the social media platform) to automatically initiate targeted advertising to potential patients on the social media platform.

As described in greater detail below, the patient 124 may receive a message or other notification directing them to the website to book an appointment at a dental office 118 for receiving an intraoral scan of the patient's teeth. The messaging system 126 may be configured to control the communications interface 112 to send notifications to the patient computing device 122 (e.g., to an email address, a phone number, to an application, to the patient portal 140, etc.) in response to various conditions. For instance, the messaging system 126 may be configured to determine that the patient previously signed up to receive an in-home dental impression kit and never returned the completed kit. The messaging system 126 may be configured to identify a time between an order date (or shipment date) of the dental impression kit and the current date. The messaging system 126 may be configured to compare the identified time to a threshold time indicative of the patient 124 likely not returning impressions from the dental impression kit. Where the identified time exceeds the threshold time, the messaging system 126 may automatically generate and send the notification to the patient 124. As another example, the messaging system 126 may determine that the impressions received from the patient 124 were, for instance, incomplete. A technician may review the impressions (or a scan thereof) to determine their suitability for fabricating dental aligners. When the impressions are determined to be incomplete, the technician may flag the impressions as incomplete. When the impressions are flagged, the messaging system 126 may automatically generate and send the message to the patient 124 prompting the patient to schedule an intraoral scan. In some embodiments, the messaging system 126 may identify a difference between a time when a treatment plan was generated and transmitted to the patient and a current time (e.g., when the patient has not purchased aligners), and automatically generate and send the message to the patient 124 when the difference exceeds a threshold.

The patient may control the patient computing device 122 to generate an appointment at the dental office for receiving an intraoral scan. The patient may generate an appointment request via the patient computing device 122 to send via the network 105 to the management engine 114. As such, the management engine 114 may be configured to receive an appointment request via a patient computing device 122 corresponding to a patient 124 requesting orthodontic treatment via dental aligners. In some embodiments, the patient may contact the dental office directly (e.g., via a phone call, via an online booking website corresponding to the dental office, etc.) for scheduling an intraoral scan. In such embodiments, the office computing device 116 may be configured to register the appointment with the management engine 114. In some implementations, the dental office 118 may offer one or more promotions in conjunction with the intraoral scan (such as a free dental hygiene cleaning with an intraoral scan, a free intraoral scan with a dental hygiene cleaning, reduced rates, etc.). Such embodiments may increase the likelihood of the patient converting an intraoral scan to treatment via dental aligners, along with retention of the patient at the dental office 118.

As described in greater detail below, the messaging system 126 may be configured to generate one or more notifications corresponding to the intraoral scan responsive to scheduling the appointment at the dental office 118. Such notifications may include, for instance, appointment reminders, day-of-appointment wayfinding messages, etc.

The management engine 114 is configured to generate a patient file 115 corresponding to the patient 124. In some embodiments, the management engine 114 may be configured to generate the patient file 115 responsive determining that the patient is a candidate for treatment (e.g., responsive to identifying the patient as a lead). In some embodiments, the management engine 114 may be configured to generate the patient file 115 responsive to the patient scheduling an appointment at a dental office. In some embodiments, the management engine 114 may be configured to generate the patient file 115 responsive to the patient requesting an at-home dental impression kit. Each patient file 115 may include data corresponding to the particular patient. The patient file 115 is updated with data as the patient progresses from a lead, to receiving an intraoral scan (or administering and returning dental impressions), to generating a treatment plan, to receiving dental aligners and ultimately receiving treatment via dental aligners. The patient file 115 may be updated by respective computing devices. As such, rather than a single computing device updating a respective patient file 115 (which can be cumbersome and lead to bogged down computing systems), the systems and methods described herein provide a central processing system 102 whereby a patient file 115 is updated by multiple computing devices associated with different tasks. Similarly, each of the portals described herein may be or include a page or other resource which is unique to a particular patient file 115. As such, upon accessing a particular patient file 115 via a respective portal, the computing devices can perform certain tasks according to the respective user of the computing device (e.g., an intraoral scan for the patient may be uploaded via the patient intake portal 128 for the patient, a treatment plan may be generated for the patient file 115 via the treatment plan portal 130, etc.). Such embodiments provide a central processing system 102 whereby each of the computing devices distributivity perform tasks associated with the patient file 115.

Patient Intake

Upon arrival at the dental office 118, the patient 124 may be directed to a location in which the patient is to receive the intraoral scan or receive impressions from a dental professional, such as a dentist, orthodontist, or a dental technician employed at the dental office. The dental professional may use the office computing device 116 to access a patient intake portal 128 during the appointment as part of the patient intake process. Referring now to FIG. 1 and FIG. 2—FIG. 8, the central processing system 102 is shown to include a patient intake portal 128. Specifically, FIG. 2—FIG. 8 show a plurality of user interfaces corresponding to the patient intake portal 128. The patient intake portal 128 may be a portal which is configured to receive and collect data corresponding to a patient intake (e.g., at the dental office 118 and/or at the intraoral scanning site 120) for populating in the patient file 115 managed by the management engine 114. In some embodiments, the patient intake portal 128 may be a program, software, website, or other resource which is provisioned, provided to, or otherwise accessible by the office computing device 116 and/or site computing device 126. The site computing device 126 may be similar in some aspects to the office computing device 116 described above.

The patient intake portal 128 may be configured to receive data corresponding to the patient intake process. As such, the patient intake portal 128 is configured to be accessed by the office computing device 116 (and site computing device 126). The office computing device 116 may be configured to access the patient intake portal 128 via the network 105 and the communications interface 112 of the central processing system 102. The user interfaces shown in FIG. 2—FIG. 8 may be rendered on the office computing device 116. In some embodiments, similar user interfaces may be rendered on the site computing device 126.

FIG. 2 shows a user interface 200 corresponding to a case review page of the patient intake portal 128. The user interface 200 may be rendered on the office computing device 116 upon log-in credentials corresponding to the dental office 118 being provided via the office computing device 116 to the patient intake portal 128. The user interface 200 is shown to include an overview of a plurality of cases 202, including case numbers 204, patient name 206, creation (or intake) date 208, and a status 210 of each of the cases 202. Statuses 210 may be assigned, received, or otherwise provided by the management engine 114, as described in greater detail below. Example statuses 210 may include, for instance, "waiting on aligner purchase," "impressions sent to manufacturer lab," "needs clearance," "treatment in progress," etc. Statuses 210 for a particular case 202 may be updated within the patient intake portal 128 as the patient file 115 for the patient is updated by the management engine 114. As shown in FIG. 2, the user interface 200 includes various user interface elements 212 for searching, viewing, or otherwise navigating between cases 202.

The user interface 200 includes a new case button 214, which may be selected by a dental professional when a new patient arrives at the dental office during a scheduled appointment. Upon selecting the new case button 214 on the user interface 200, the dental professional may be prompted to provide additional details regarding the patient for patient intake purposes.

Figure 3:
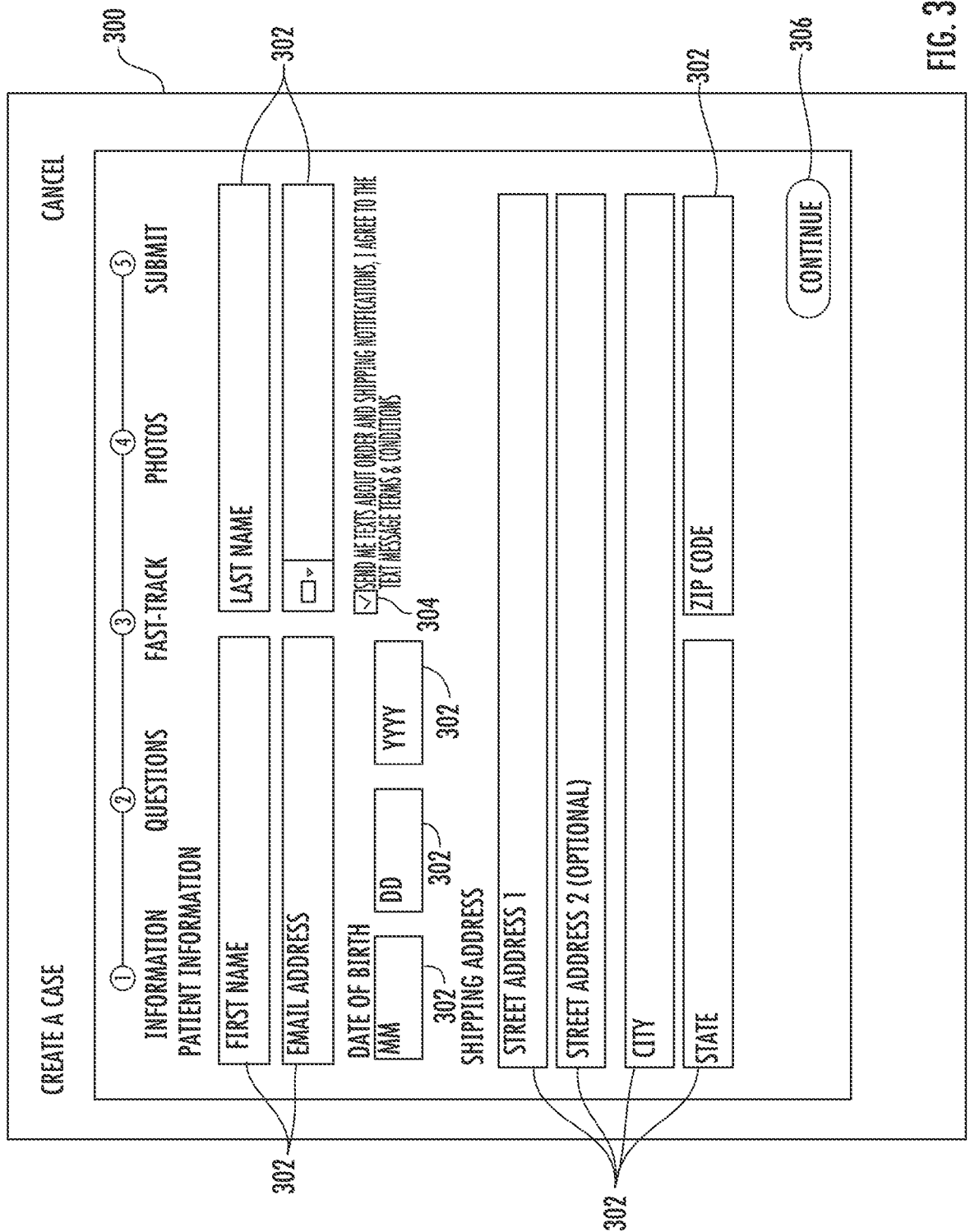
FIG. 3 shows a user interface of the patient intake portal of FIG. 1 for generating a new case, according to an illustrative embodiment.

FIG. 3 shows a user interface 300 corresponding to generation of a new case at the dental office 118. The user interface 300 may be rendered on the office computing device 116 responsive to selection of the new case button 214 in the user interface 200 shown in FIG. 2. The user interface 300 is shown to include various text fields (or text boxes) 302 which correspond to the patient. Each of the text fields 302 may be populated by the patient and/or by the dental professional during the patient intake process. For example, the text fields 302 may include fields 302 for receiving patient information (such as first and last name, email address, phone number, date of birth, etc.). The text fields 302 may include fields 302 corresponding to a patient home or billing address (e.g., street address, city, state, zip code), a shipping address (e.g., which may be the same as the patient or billing address if the patient requests shipment of dental aligners to the patient's home, or may be different if the patient requests shipment of dental aligners to a different location). The user interface 300 may include a button 304 which authorizes the dental aligner manufacturer to send notifications (such as text messages, emails, or other notifications) regarding the patient's order or shipping notifications, which may also include a link to terms and conditions for selecting the button 304. Once the text fields 302 have been populated by the dental professional and/or patient during the patient intake process, the operator of the office computing device 116 may select continue button 306.

FIG. 4 shows a user interface 400 corresponding to dental history information and consent. The user interface 400 may be rendered on the office computing device 116 responsive to selection of the continue button 306 in the user interface 300 shown in FIG. 3. As shown in FIG. 4, the user interface 400 includes various selectors 402 in which the dental professional may select during an examination of the patient. The dental professional may request or solicit information from the patient regarding, for example, dental history, consent to treatment, etc., or otherwise perform an examination of the patient to obtain information corresponding to the dental history for the patient. As shown in FIG. 4, the dental history information may include, for example, options for selecting whether the patient 124 has a bonded retainer, bridgework, crowns, an impacted tooth, an implant, primary teeth, or veneers. Each of these options may include a corresponding selector 402. Similarly, the dental history information may include options for selecting whether the patient 124 had a recent radiograph taken of their teeth, has pain in any teeth, has any sores or lumps in or near the patient's mouth, has any indication of a serious dental issue identified by a dentist within the last six months, any existing head, neck, or jaw injuries, any jaw clicking, pain, or difficulty opening, closing, or chewing, whether the dental professional has identifies any loosening of teeth or periodontal disease, whether the patient has any known allergies to any dental materials, whether the patient has any history of IV bisphosphonate treatment, whether the patient is currently on any acute corticosteroids or in immunosuppression, chemotherapy, or radiation of the head or neck, and whether the patient has had any bone marrow transplant or treatment of hematological malignancies (blood cancers) within the past two years. Each of these options may include a selector 402 for selecting all of the options which apply to the patient 124. The user interface 400 is shown to include a selector 404 corresponding to patient consent, which indicates the patient's consent to the aligner manufacturer's informed consent policies, terms, and financing conditions. Each of the policies, terms, and financing conditions shown on the user interface 400 may include hyperlinks for which the patient may select and review the policies, terms, and financing conditions prior to selecting the selector 404 indicating the patient's consent. Once the dental history information and consent is received via the user interface 400, the dental professional may select a continue button 406 on the user interface 400.

Figure 5:
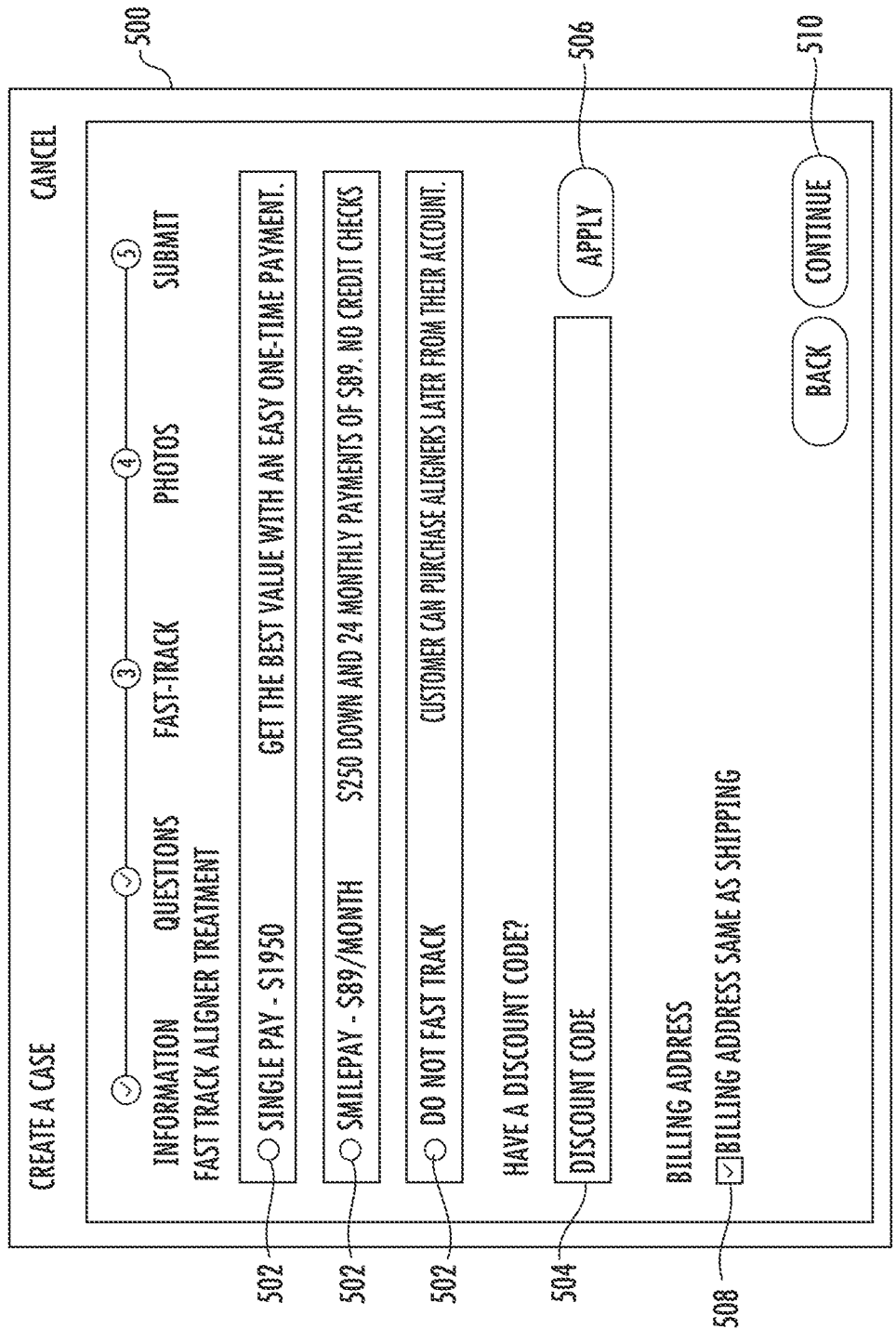
FIG. 5 shows a user interface of the patient intake portal of FIG. 1 for selecting payment information, according to an illustrative embodiment.

FIG. 5 shows a user interface 500 corresponding to payment information. The user interface 500 may be rendered on the office computing device 116 responsive to selection of the continue button 406 in the user interface 400 shown in FIG. 4. As shown in FIG. 5, the user interface 500 includes an overview and corresponding buttons 502 of various fast track options for payment for dental aligners. The options may include a single pay fast track option where the patient 124 makes a one-time payment for the dental aligners. The options may include a fast track financing option where the patient makes a down payment and monthly payments. Where the patient 124 selects one of the fast track options, the user interface 500 may be updated to include various fields for receiving payment information (e.g., if the single pay option button 502 is selected) or financing application information (if the financing option button 502 is selected). Where the patient 124 selects a fast track option, the patient 124 may automatically approve a treatment plan (e.g., without reviewing the treatment plan and positively approving the treatment plan). The user interface 500 may also include a button 502 corresponding to deferring payment for dental aligners. Where the patient 124 selects the button 502 corresponding to the deferring payment option, the patient 124 may approve of the treatment plan at a later date and purchase the dental aligners subsequent to approval of the treatment plan. The user interface 500 is shown to include a field 504 for providing any discount codes in which the patient may provide to the dental professional, and a corresponding button 506 for applying the discount code. The user interface 500 includes a selector 508 for selecting whether the billing address for payment is the same as the shipping address (e.g., provided to the user interface 300 shown in FIG. 3). If the selector 508 is de-selected, a series of fields similar to those shown in FIG. 3 may be included in the user interface 500 for the patient to provide a billing address. Once the patient selects a button 502 corresponding to payment for dental aligners, applies any discount codes, and selects whether the billing address is the same as the shipping address, the dental professional may select a continue button 510 on the user interface 500.

Figure 6:
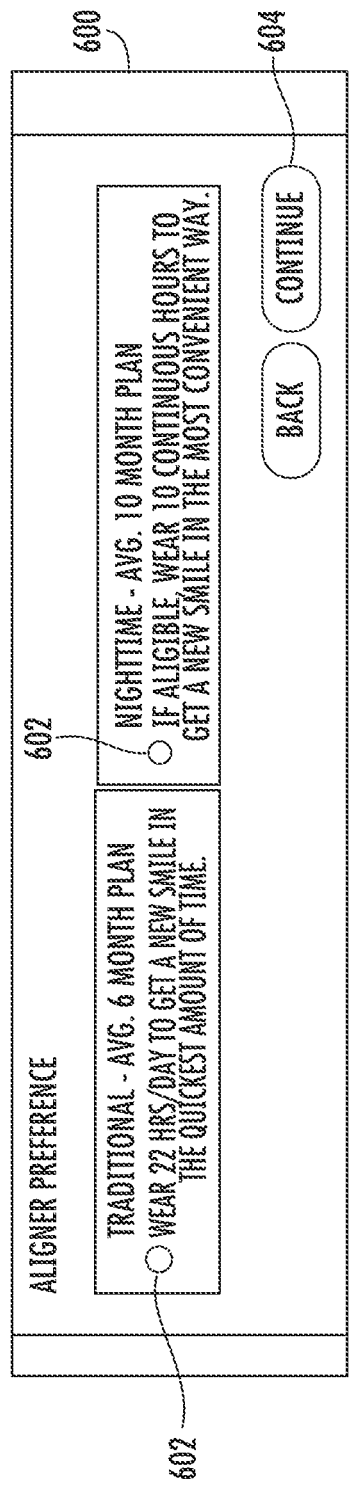
FIG. 6 shows a user interface of the patient intake portal of FIG. 1 for selecting a dental aligner preference for the patient, according to an illustrative embodiment.

FIG. 6 shows a user interface 600 corresponding to selecting a dental aligner preference by the patient. The user interface 600 may be rendered on the office computing device 116 responsive to selection of the continue button 510 in the user interface 500 shown in FIG. 5. As shown in FIG. 6, the user interface 600 includes buttons 602 and corresponding information on two different types of dental aligner programs. One program may be a traditional dental aligner program and another program may be a nighttime dental aligner program. The traditional dental aligner program may take an average of six months to complete, and may entail the patient wearing dental aligners for approximately 22 hours a day. The nighttime dental aligner program may take an average of 10 months to complete, and may entail the patient wearing dental aligners for approximately 10 continuous hours a day (e.g., at night). The nighttime dental aligner program may only be offered to some eligible patients. However, the patient 124 may indicate their preference on a particular program by selecting a button 602 on the user interface 600 (or instructing the dental professional to select a particular program). Once a button 602 corresponding to a preferred program for the patient 124 is selected on the user interface 600, the dental professional may select a continue button 604 on the user interface 600.

Figure 7:
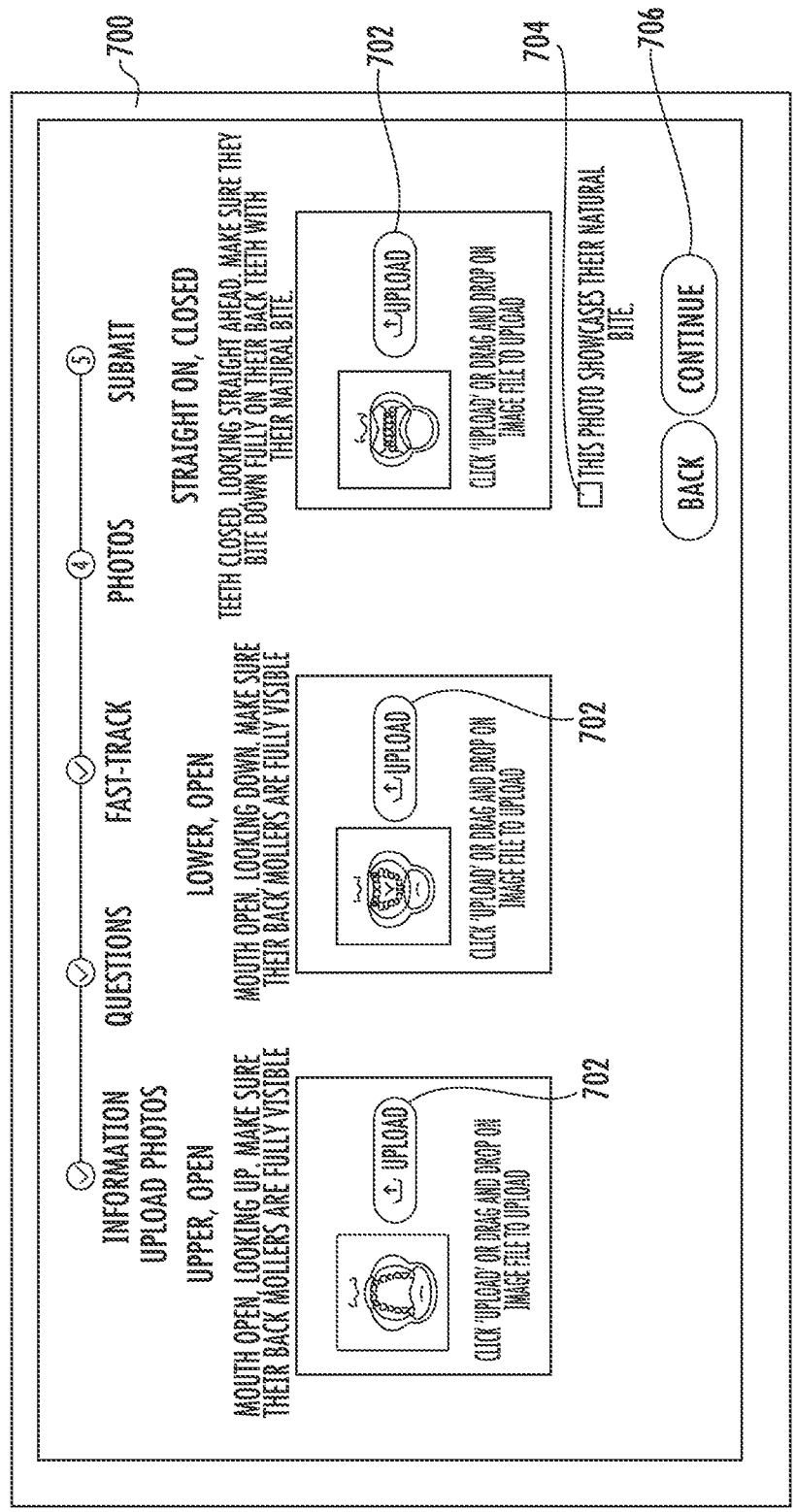
FIG. 7 shows a user interface of the patient intake portal of FIG. 1 for uploading one or more photographs of the patient, according to an illustrative embodiment.

FIG. 7 shows a user interface 700 corresponding to uploading one or more photographs of the patient. The user interface 700 may be rendered on the office computing device 116 responsive to selection of the continue button 604 in the user interface 600 shown in FIG. 6. As shown in FIG. 7, the user interface 700 includes a series of example photographs and explanations which describe photographs which are to be captured by the dental professional of the patient. As shown in FIG. 7, the dental professional may be instructed to take the photographs of the patient's upper and lower open jaw with the patient's mouth open (e.g., with the patient looking up or down, respectively, to expose the patient's molars). The dental professional may be instructed to take a photograph of a straight-on, closed view of the patient's teeth with the patient biting down fully on their back teeth with their natural bite. Once the dental professional captures the patient photographs, the dental professional may select an upload button 702 for uploading each photograph. Upon selecting the upload button 702, the user interface 700 may be updated to include a file explorer where the dental professional can locate and select the corresponding photograph file for uploading. In some implementations, the dental professional may drag and drop a file corresponding the photograph onto or adjacent to the upload button 702 to upload the file. The user interface 700 is shown to include a selector 704 for verifying that the straight-on, closed photograph of the patient showcases the patient's natural bite. Once the dental professional uploads each of the requested photographs and selects the selector 704, the dental professional may select a continue button 706 on the user interface 600.

Figure 8:
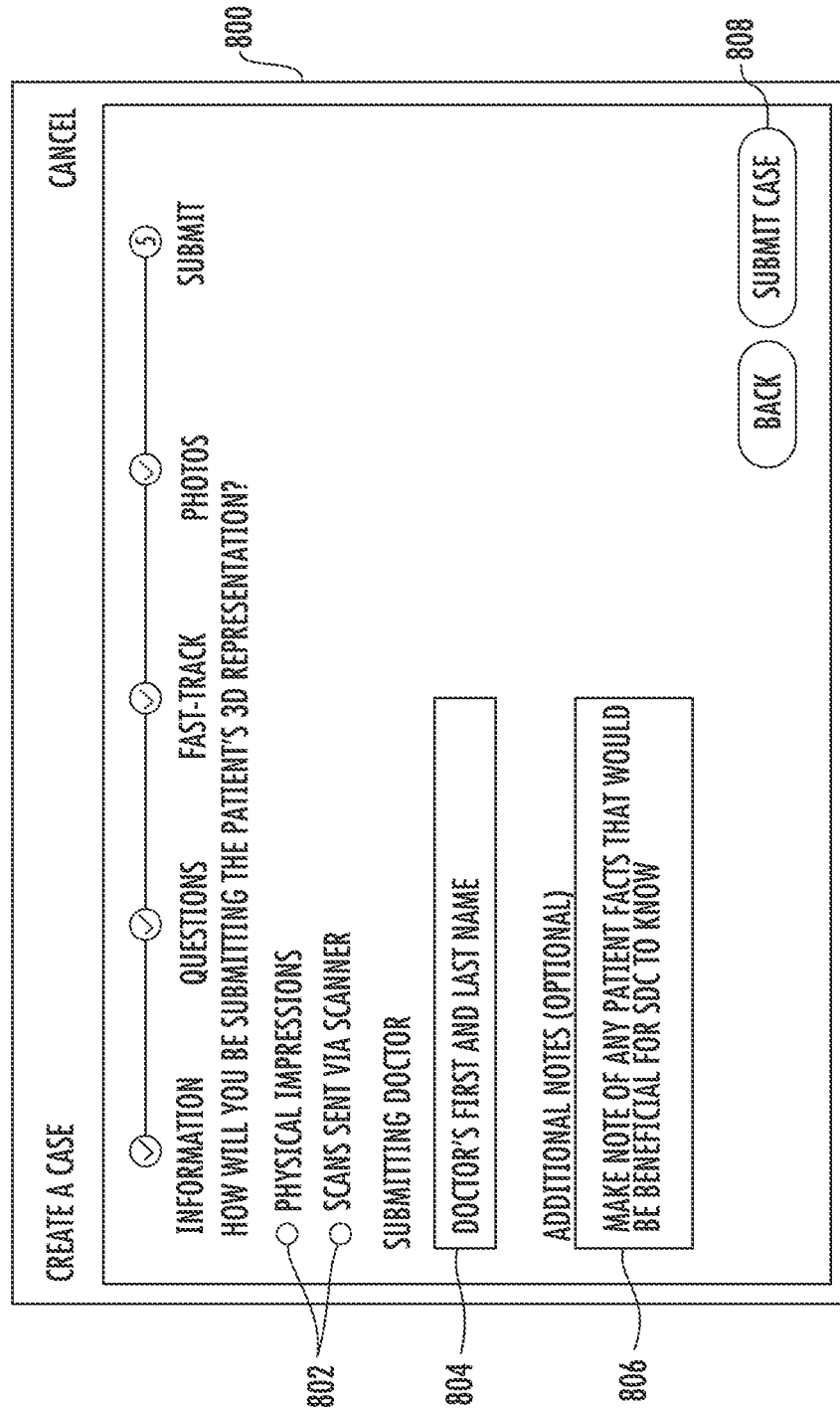
FIG. 8 shows a user interface of the patient intake portal of FIG. 1 for submitting the new case, including selecting an impression submission option, according to an illustrative embodiment.

FIG. 8 shows a user interface 800 corresponding to selecting an impression submission option. The user interface 800 may be rendered on the office computing device 116 responsive to selection of the continue button 706 in the user interface 700 shown in FIG. 7. As shown in FIG. 8, the user interface 800 includes buttons 802 for selecting an option in which the dental professional is providing the dental aligner manufacturer with a three-dimensional (3D) representation corresponding to the patient's dentition. The options may include an intraoral scan in which a 3D model is provided by an intraoral scanner as described below. In some instances, such as where the dental office 118 does not have an intraoral scanner, the dental professional may opt to provide 3D representations via physical dental impressions (e.g., of the patient's upper and/or lower dental arches) which are sent from the dental office 118 to a technician (e.g., corresponding to the dental aligner manufacturer) to scan for generating a 3D model. For example, the dental professional may administer dental impressions for the patient using their own impression material, impression material provided by the dental aligner manufacturer during enrollment (or subsequently purchased or otherwise obtained from the manufacturer), and so forth. Where the dental professional selects the option to provide 3D representations via physical impressions, the management engine 114 may automatically transmit, send, or otherwise provide a shipping label to the office 118 for the dental professional to send the impressions to the technician (which may be located at the treatment plan system 130, at the fabrication system 144, or other location which is separate from the dental office 118). The dental impressions may be received by the technician, and scanned in a manner similar to the intraoral scans described herein. As such, the dental impressions may be scanned to generate a 3D model of the patient's dental arches.

The user interface 800 also includes a field 804 for the dental professional to provide their first and last name, and a field 806 for providing any additional notes of patient facts which would be beneficial for the dental aligner manufacturer to know. Following the dental professional completing all fields in the user interface 800, the dental professional may select a submit case button 808 to upload the case to the patient intake portal 128 for populating the patient file 115 by the management engine 114, as described in greater detail below.

Referring back to FIG. 1, following obtaining information corresponding to the patient described above, the patient 124 may be directed to a room or space within the dental office 118 where the patient 124 will receive their intraoral scan. The dental professional at the dental office 118 may administer the intraoral scan. The dental professional may administer the intraoral scan using, for instance, an iTero® scanner (or other intraoral scanner). As the dental professional administers the intraoral scan, the intraoral scanner may produce data which is visually represented on a display. The data may include a three-dimensional (3D) representation or model of the patient's 124 mouth. In some embodiments, the intraoral scanner may be configured to transmit, send, or otherwise provide raw data to an external computing device or system for generating a 3D model (or other form of data which represents the 3D structure) corresponding to the mouth of the patient. The external computing device may transmit the 3D model back to the office computing device 116 for linking with the patient file 115. In some embodiments, the intraoral scanner may be configured to transmit, send, or otherwise provide raw data with an identifier to the external computing device. The office computing device 116 may use the identifier for linking the three-dimensional data generated by the external computing device with the patient file 115, as described in greater detail below.

The office computing device 116 may be configured to upload, transmit, or otherwise cause the 3D model to be shared or otherwise accessible to the patient intake portal 128. In some embodiments, the office computing device 116 may be configured to upload the 3D model corresponding to the intraoral scan received from the intraoral scanner to the patient intake portal 128 on a user interface similar to the user interface 700 shown in FIG. 7. In some embodiments, the office computing device 116 may be configured to upload the 3D model from the external computing device to the patient intake portal 128. In some embodiments, the office computing device 116 may be configured to transmit the identifier corresponding to the raw data for the intraoral scan to a field on the user interface 800 of the patient intake portal 128, and the management engine 114 may be configured to retrieve or otherwise access the 3D model from the external computing device using the identifier.

In these and other embodiments, the management engine 114 may be configured to populate the patient file 115 with the 3D model corresponding to the intraoral scan based on data received from the office computing device 116. Similarly, the office computing device 116 may be configured to upload, transmit, send, or otherwise provide responses to the dental history and consent information and the patient photograph(s) the patient intake portal 128 as described above with reference to FIG. 2—FIG. 8. As such, the management engine 114 may be configured to populate the patient file 115 with the 3D model, the patient photograph(s), and dental history data.

In some embodiments, the dental office 118 may be provided with a pamphlet or handout which may be provided to the dental office 118 responsive to enrollment with the dental aligner manufacturer. The handout may include a step-by-step process in which the dental professionals (or other staff) at the dental office 118 are to walk patients through the steps described above, along with details on financing options and information on what to expect following the scan and through treatment. In some embodiments, the dental office 118 may be provided with additional materials responsive to enrollment with the dental aligner manufacturer. For example, the dental office 118 may be provided with patient brochures which explain how treatment works, frequently asked questions, etc. The dental office 118 may be provided with table top cards, frequently asked question (FAQ) sheets, before and after books showing pictures of patients which were treated, decals, an example ship-at-once aligner box with sample aligners included therein, aligner cases, and so forth. The dental office 118 may also be provided with whitening samples and tooth brushes to provide to patients. The dental office 118 may also be provided with various supplies, such as dental appliances for positioning in the patient's mouth while capturing photographs as described above, impression materials (such as putty and impression trays), and so forth. The dental office 118 may contact the dental aligner manufacturer (or access the patient intake portal 128) to order additional supplies, pamphlets, samples, etc.

Approval for Treatment

Following receiving the intraoral scan, the patient may approve generating a treatment plan. In some instances, the patient may approve generating the treatment plan at the dental office (e.g., prior to, during, or following the intraoral scan) by selecting one of the fast track options shown in FIG. 5 and described above. In such embodiments, the office computing device 116 may be configured to upload a command to the patient intake portal 128 which indicates that the patient has approved generating the treatment plan. In some embodiments, the patient may approve generating the treatment plan subsequent to the appointment at the dental office. For example, the patient may approve generating the treatment plan via the patient computing device 122 in response to a notification from the messaging system 126. As another example, the patient may access a patient portal 140 (described in greater detail below) for approving generating a treatment plan.

In some embodiments, the patient may be approved as being fit for treatment via dental aligners. In some implementations, a different dental professional may approve the patient as being fit for treatment. For example, the different dental professional may be a member of a network of approving dental professionals who review patient files 115 for fitness for treatment via dental aligners. The approving dental professionals are separate from the dental professional who administers the intraoral scan. For example, the network of approving dental professionals may be located in each state, and may be separate from dental professionals who have enrolled with the central processing system 102 for administering intraoral scans. The approving dental professionals may approve or deny patients for treatment via respective approving dental computing devices 138, as described in greater detail below. For example, the approving dental professionals may access data corresponding to a patient file 115 using an approving dental portal 136, for approving a patient as being fit for treatment via dental aligners.

The management engine 114 may be configured to receive one or more commands corresponding to the patient being approved as fit for treatment via dental aligners and the patient approving generating the treatment plan. The commands may be received from approving dental computing device 138 and, optionally, the patient computing device 122. The management engine 114 may be configured to update the patient file 115 to indicate receipt of the command(s). For example, the management engine 114 may be configured to update the patient file 115 to include a first status which indicates that the patient has been approved as being fit for treatment via dental aligners, and a second status which indicates that the patient has approved generating the treatment plan. The management engine 114 may be configured to cause generation of a treatment plan responsive to the patient being approved as being fit for treatment and the patient approving generating the treatment plan.

Treatment Plan Generation

The system 100 is shown to include a treatment plan computing system 130 including one or more treatment plan computing devices 132. The treatment plan computing system 130 may be located at a treatment plan site which is separate from the dental offices 118 and intraoral scanning sites 120, such as at a different location within the same city, within a different city, within a different state, etc. In some embodiments, the treatment plan computing system 130 may be located at a plurality of locations (e.g., the treatment plan computing system 130 may be distributed across a plurality of locations), with each location having a respective treatment plan computing device 132. The treatment plan computing system 130 (and computing devices 132) may be communicably coupled to the central processing system 102 via the network 105 using the communications interface 112.

The central processing system 102 is shown to include a treatment plan portal 134. The treatment plan portal 134 may be a portal which is configured to provision, send, transmit, or otherwise provide a treatment plan computing device 132 of a treatment plan computing system 130 access to one or more portions of the patient file 115. In some embodiments, the treatment plan portal 134 may be a program, software, website, or other resource which is provisioned or otherwise provided to the treatment plan computing devices 132. The treatment plan computing devices 132 may be configured to access the 3D model, dental history information, and the patient photograph(s). The treatment plan computing devices 132 may be configured to use the 3D model to generate a treatment plan for the patient, as described in greater detail below.

The treatment plan computing device 132 may be configured to generate the treatment plan by manipulating individual 3D teeth models of teeth within the 3D model corresponding to the intraoral scan. In some implementations, the treatment plan computing device 132 may be configured to receive inputs from an operator or technician to manipulate individual 3D teeth models within the 3D model of the patient's dental arches. In some implementations, the treatment plan computing device 132 may be configured to automatically "snap" (or move) the individual 3D teeth models to a default dental arch. The treatment plan computing device 132 may be configured to receive inputs corresponding to one or more modifications of the automatic movement of the 3D teeth models. In various embodiments, the manipulation of the 3D model may show a final (or target) position of the teeth of the patient following treatment via dental aligners. The treatment plan computing device 132 may be configured to automatically generate a treatment plan based on the initial position (e.g., as reflected in the 3D model corresponding to the intraoral scan) and the final position (e.g., following manipulation of the 3D model and any optional adjustments). In some embodiments, the treatment plan computing device 132 may be configured to apply one or more movement thresholds (e.g., a maximum lateral and/or rotational movement for a particular stage of treatment) to each of the individual 3D teeth models for generating the treatment plan. As such, the treatment plan may be generated in accordance with the movement thresholds.

The treatment plan may be embodied as any data indicative of a series of steps used to correct or otherwise modify the positions of the patient's teeth from the initial position to the final position. In particular, the treatment plan may represent the patient's teeth and how they move through the duration of the treatment plan. The treatment plan may be directed to the patient's upper teeth, lower teeth, or both upper and lower teeth. The treatment plan may include a series of 3D models which represent the patient's teeth as they move through the duration of the treatment plan. The 3D models of the treatment plan may be embodied as STL files, OBJ files, or any other data file that is indicative of a three-dimensional object and/or scene.

The treatment plan computing device 132 may be configured to upload, transmit, send, or otherwise provide the treatment plan data (e.g., the data corresponding to the 3D models of the treatment plan) to the treatment plan portal 134 via the network 105 using the communications interface 112. The management engine 114 may be configured to update, include, embed, or otherwise populate the patient file 115 with the treatment plan data. In some embodiments, the management engine 114 may be configured to generate one or more visual representations of the treatment plan data. For example, the management engine 114 may be configured to generate an animation showing a progression of the 3D models from the initial position to the final position. As another example, the management engine 114 may be configured to generate a slideshow or other presentation which shows the progression of the 3D models.

Treatment Plan Approval

The treatment plans may be approved by a dental professional, such as a dentist or orthodontist, and by the patient. As noted above, in some instances, the patient may select a fast track option whereby the patient approves generation of a treatment plan and fabricating aligners based on the treatment plan. In such instances, the treatment plan may only be approved by the dental professional.

The treatment plan may be approved by a dental professional via the approving dental computing device 138. As described above, the approving dental computing device 138 may be configured to access the approving dental portal 136. The approving dental computing device 138 may be configured to access the approving dental portal 136 for approving or denying the treatment plan for the patient. The approving dental computing device 138 is configured to retrieve, download, view, or otherwise access the treatment plan data via the approving dental portal 136. In some embodiments, the approving dental computing device 138 may be configured to access the treatment plan data with the dental history information and photographs to determine that the treatment plan is acceptable for the patient (e.g., that the treatment plan satisfies the movement threshold(s), that the final position of the patient's teeth are properly located, etc.). In some embodiments, the treatment plan data may include the visual representations of the treatment plan generated by the treatment plan computing device 132 and/or the management engine 114. In some embodiments, the visual representations may be modified or optimized for viewing at the approving dental computing device 138. For example, the visual representation of a particular stage of the treatment plan may include overlays or a chart which depicts measured movements of individual teeth from their position the preceding stage to their position at the particular stage (e.g., delta movement between two stages). Such embodiments may provide the approving dental professional with additional data points for approving or denying a treatment plan for a particular patient.

The approving dental professional may review the treatment plan data (including the dental history information and the patient photographs) at the approving dental computing device 138 to approve or deny the treatment plan for the patient. As noted above, the approving dental professional is separate from the dental professional at the dental office where the patient received an intraoral scan or impressions. In other words, a first dentist or orthodontist, or a dental technician employed at the dental office of the first dentist or orthodontist, may administer an intraoral scan or impressions at the dental office 118, and a second dentist or orthodontist may approve of the treatment plan. As such, the approving dental professional may approve the treatment plan for the patient without ever seeing the patient in-person (e.g., at any appointment with the approving dental professional). The approving dental professional may select an approve (or deny) button on a user interface of the approving dental computing device 138 corresponding to the approving dental portal 136. The approving dental computing device 138 may be configured to transmit a command to the central processing system 102 (e.g., via the network 105 using the communications interface). The approving dental portal 136 may be configured to receive the command from the approving dental computing device 138. The management engine 114 may be configured to populate, update, or otherwise indicate receipt of the command from the approving dental computing device 138 in the patient file 115 (e.g., as a status or other indicator in the patient file 115 which indicates the treatment plan has been approved by the approving dental professional).

In instances in which the patient 124 does not select a fast track option, the patient may also approve the treatment plan. For example, the patient 124 may control the patient computing device 122 to access the patient portal 140. The patient portal 140 may be a portal which is configured to provision, send, transmit, or otherwise provide the patient computing device 122 access to the treatment plan data. In some embodiments, the patient portal 140 may be a program, software, website, or other resource which is provisioned or otherwise provided to the patient computing device 122. In some embodiments, the treatment plan data included in the patient portal 140 may be a modified version of the treatment plan data included in the approving dental portal 136. In some implementations, the treatment plan data included in the patient portal 140 may include a visual representation of the treatment plan without the measured movements of the patient's teeth. For example, the treatment plan data may be simplified version of the treatment plan data included in the approving dental portal 136. The treatment plan data may show a visual representation of the progression of the patient's teeth from their initial position (prior to treatment) to a final position (post treatment). The visual representation may include an animation of the steps or stages of the treatment plan, a slideshow or other framed representation of steps or stages of the treatment plan, etc.

Similar to the approving dental professional, the patient 124 may select an option on the patient portal 140 to approve or deny the treatment plan. Where the patient 124 selects an approval option, the patient 124 may be prompted to provide payment information (such as a credit card of the patient, selecting and applying for a financing option through the dental aligner manufacturer or other entity, etc.) for fabricating dental aligners according to the treatment plan. The patient 124 may operate or otherwise provide inputs to the patient computing device 122 to provide the approval option and payment information to the patient portal 140. The patient computing device 122 may be configured to transmit a patient command indicating approval of the treatment plan to the patient portal 140, which may accompany (or be sent in conjunction with) the payment information. The patient portal 140 may be configured to receive the patient command and the payment information from the patient computing device 122 (e.g., from the communications interface 112 via the network 105). The management engine 114 may be configured to update, populate, or otherwise indicate receipt of the patient command and payment information from the patient computing device 122 in the patient file 115 (e.g., as a status or other indicator in the patient file 115 which indicates the treatment plan has been approved by the patient and payment information has been received).

As described in greater detail below, dental aligners may be fabricated responsive to receipt of commands from the approving dental professional (e.g., via the approving dental portal 136 from the approving dental computing device 138) and the patient (e.g., via the patient portal 140 from the patient computing device 122), and receipt of payment information from the patient.

In some embodiments, the dental aligner manufacturer may initiate payment (e.g., a flat fee for services rendered) to the dental office 118 which is conditioned on receipt of payment information from the patient. In some embodiments, the dental aligner manufacturer may initiate payment to the dental office 118 responsive to fabrication of the dental aligners for the patient according to the treatment plan. In other embodiments, the dental aligner manufacturer may initiate payment to the dental office 118 responsive to shipment of the dental aligners to the patient. In these and other embodiments, payment may be initiated from an account corresponding to the central processing system 102 for the dental aligner manufacturer to an account of the dental office. In some embodiments, the management engine 114 may be configured to cause payment from an account corresponding to the central processing system 102 to an account corresponding to the dental office 118. Payment may be automatically initiated at a time of receipt of payment information from the patient 124, at a time of fabricating the dental aligners, at a time of shipment of the dental aligners, etc. In some instances, payment may be automatically initiated within a time frame of receipt of payment information, at a time of fabricating the dental aligners, at a time of shipment of the dental aligners, etc. For example, payment may be automatically initiated at an end of the month (or within 30 days) from receipt of the payment information, from fabrication or shipment of the dental aligners to the patient, etc.

As such, rather than other implementations where a patient pays a dental office for orthodontic treatment to compensate both the dentist or orthodontist and to cover the expenses the dental office paid to a dental aligner manufacturer (which may result in increased overall costs to the patient), in the embodiments described herein, the patient provides a payment directly to the dental aligner manufacturer (such as through one of the financing options offered by the dental aligner manufacturer or a one-time payment to the dental aligner manufacturer). Once the dental aligners are shipped to the patient, the dental aligner manufacturer then initiates payment to the dental office to compensate the dentist or orthodontist for performing the intake of the patient, including conducting the intraoral scan or the taking of impressions. Such embodiments reduce the overall transaction costs as well as the costs to the patient for receiving orthodontic treatment.

Dental Aligner Fabrication

Once the treatment plan is approved by the approving dental professional and the patient 124, the treatment plan data may be used to fabricate one or more dental aligners. As shown in FIG. 1, the system 100 includes a fabrication portal 142 and a fabrication system 144. The fabrication system 144 may be located at a fabrication site which is separate from the location of the dental offices 116 and treatment plan site. The fabrication system 144 may be configured to receive treatment plan data via the fabrication portal 142 which is used to fabricate one or more dental aligners 146. The fabrication system 144 is shown to include a fabrication computing device 148 and fabrication equipment 150, 152 configured to produce, manufacture, or otherwise fabricate dental aligners 146. The fabrication computing device 148 is configured to access the fabrication portal 142 for retrieving or otherwise receiving the treatment plan data from the patient file 115 corresponding to the patient.

The fabrication portal 142 may be a portal which is configured to provision, send, transmit, or otherwise provide the fabrication computing device 148 access to the treatment plan data. In some embodiments, the management engine 114 may be configured to automatically transmit the treatment plan data via the fabrication portal 142 to the fabrication computing device 148 responsive to receiving the commands from the approving dental computing device 138 and the patient computing device 122. The fabrication computing device 148 may be configured to receive a plurality of 3D models corresponding to the treatment plan for the patient. Each 3D model may be representative of a particular stage of the treatment plan (e.g., a first 3D model corresponding to an initial stage of the treatment plan, one or more intermediate 3D models corresponding to intermediate stages of the treatment plan, and a final 3D model corresponding to a final stage of the treatment plan). The fabrication system 144 may be configured to use the 3D models for manufacturing, generating, producing, or otherwise fabricating dental aligners 146.

The fabrication system 144 is shown to include fabrication equipment. In some embodiments, the fabrication equipment may include a 3D printing system 150. The 3D printing system 150 may be used to 3D print physical models corresponding the 3D models of the treatment plan. As such, the 3D printing system 150 may be configured to fabricate physical models which represent each stage of the treatment plan. In some implementations, the fabrication system 144 may include casting equipment configured to cast, etch, or otherwise generate physical models based on the 3D models of the treatment plan. Where the 3D printing system 150 (or casting equipment) generates physical models, the fabrication system 144 may also include a thermoforming system 152. The thermoforming system 152 may be configured to thermoform a polymeric material to the physical models, and cut, trim, or otherwise remove excess polymeric material from the physical models to fabricate a dental aligner. In some embodiments, the 3D printing system 150 may be configured to directly fabricate dental aligners (e.g., by 3D printing the dental aligners directly based on the 3D models of the treatment plan). Additional details corresponding to fabricating dental aligners are described in U.S. Provisional Patent Appl. No. 62/522,847, titled "Dental Impression Kit and Methods Therefor," filed Jun. 21, 2017, and U.S. patent application Ser. No. 16/047,694, titled "Dental Impression Kit and Methods Therefor," filed Jul. 27, 2018, the contents of each of each of such applications are incorporated herein by reference in their entirety.

The fabrication system 144 may be configured to generate or otherwise fabricate dental aligners for each stage of the treatment plan. In some instances, each stage may include a plurality of dental aligners 146 (e.g., a plurality of dental aligners 146 for the first stage of the treatment plan, a plurality of dental aligners 146 for the intermediate stage(s) of the treatment plan, a plurality of dental aligners 146 for the final stage of the treatment plan, etc.). Each of the dental aligners 146 may be worn by the patient in a particular sequence for a predetermined duration (e.g., two weeks for a first dental aligner of the first stage, two weeks for a second dental aligner of the first stage, etc.).

The system 100 is shown to include a shipment processing system 154. The shipment processing system 154 may be configured to package and ship the dental aligners 146 to the patient. In some embodiments, the dental aligners 146 may be packaged in sequence. For example, the dental aligners 146 may be packaged according to the sequence in which the patient is to wear the dental aligners 146. In some instances, the dental aligners 146 may be packaged and shipped all at once. In other words, the shipment processing system 154 may be configured to package each of the dental aligners 146 for the treatment plan in a single package and in the sequence in which the patient is to wear each of the dental aligners 146 throughout the duration of treatment. In some instances, the dental aligners 146 may be shipped in stages (e.g., a plurality of dental aligners 146 for the first stage of the treatment plan may be packaged and shipped to the patient at a first point in time, a plurality of dental aligners 146 for the intermediate stage(s) of the treatment plan may be packaged and shipped to the patient at a second point in time, a plurality of dental aligners 146 for the final stage of the treatment plan may be packaged shipped to the patient at a third point in time, etc.).

The shipment processing system 154 may be configured to ship the packaged dental aligners 146 to the patient. In some embodiments, the shipment processing system 154 may be configured to ship the packaged dental aligners 146 to an address specified by the patient using an input provided by the patient computing device 122 to the patient portal 140. For example, the patient may provide an input to the patient computing device 122 which indicates a home or work address corresponding to the patient. The patient portal 140 may be configured to receive the address specified by the patient for shipment of the dental aligners 146. The management engine 114 may be configured to update the patient file 115 to indicate a location in which the shipment processing system 154 is to send the dental aligners 146. The shipment processing system 154 may be configured to ship the dental aligners 146 to the address specified to the patient. The shipment processing system 154 may be configured to ship the dental aligners 146 by providing the packaged dental aligners 146 to one or more carriers which transport the packaged dental aligners 146 to the address specified by the patient. In these embodiments, the dental aligners 146 may be sent to the patient without first providing the dental aligners 146 to the approving dental professional, to the dental office 118 or intraoral scanning site 120, or other entities associated with the generation/approval of the treatment plan.

Report Generation

Figure 9:
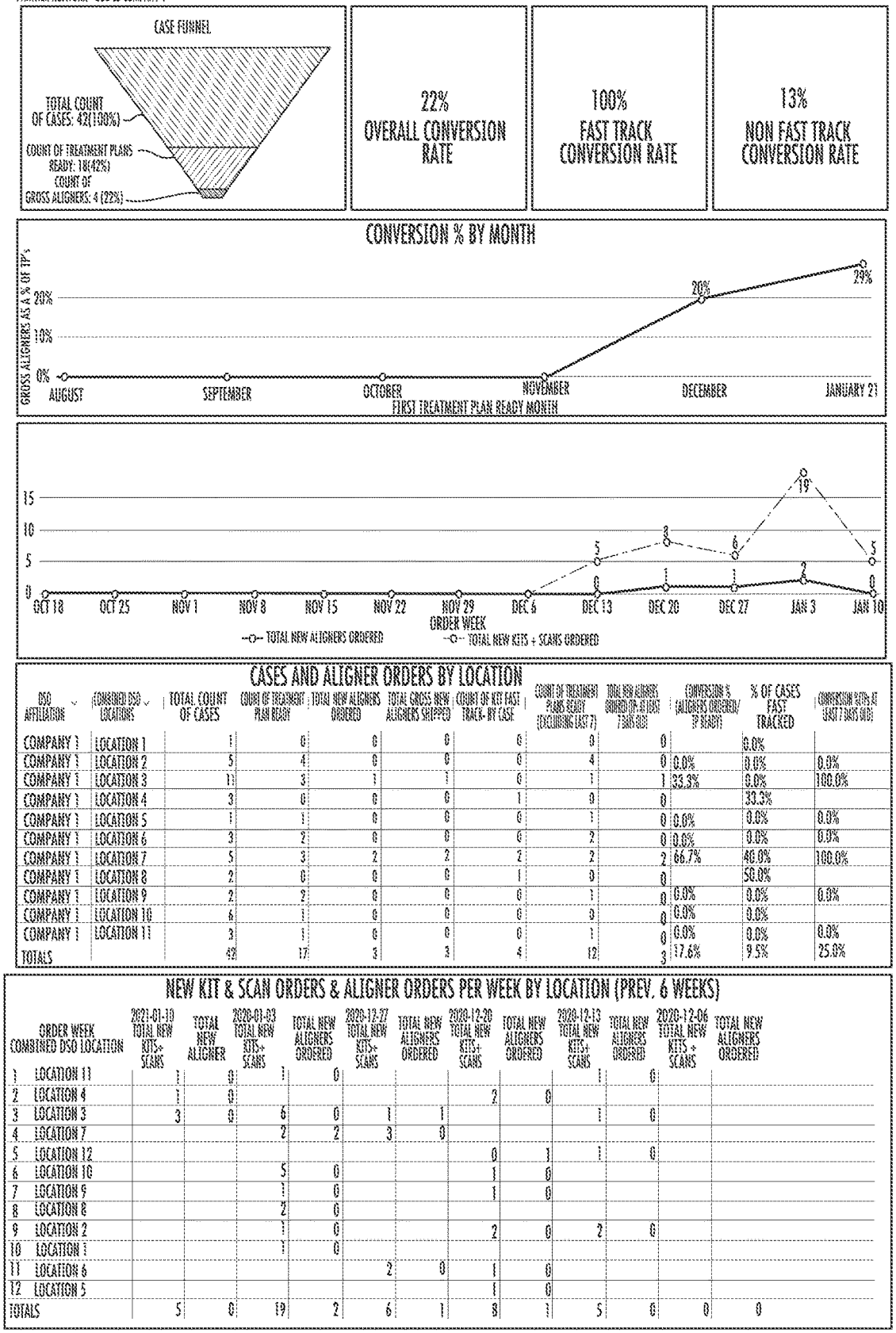
FIG. 9 is an example report which is generated by a management engine of the system of FIG. 1, according to an illustrative embodiment.

Referring now to FIG. 1 and FIG. 9, the management engine 114 may be configured to generate various reports for sending to the dental office 118. Specifically, FIG. 9 shows an example report which is generated by a management engine 114 for sending to the dental office 118. As noted above with respect to FIG. 2, a dental office 118 may include any number of outstanding cases 204 (of FIG. 2). The management engine 114 may be configured to generate reports for each dental office 118 (or group of dental offices 118 affiliated with one another) enrolled with the dental aligner manufacturer to indicate various metrics corresponding to the outstanding cases 204. In some embodiments, each patient file 115 may include an identifier which is linked or otherwise associated with the dental office 118 at which the patient received an intraoral scan (or dental impression). The management engine 114 may be configured to access each of the patient files 115 for generating reports for the dental offices 118. For example, the management engine 114 may be configured to sort, categorize, or otherwise group patient files 115 by identifiers corresponding to a respective dental office 118. The management engine 114 may be configured to populate the report with various information from the patient files 115, such as a status of each patient file 115 for the dental office 118.

As shown in FIG. 9, the report may include various statistics. The management engine 114 may be configured to compute, determine, populate, or otherwise provide the statistics in the report for the dental offices 118. For example, the management engine 114 may be configured to generate one or more graphics showing a case funnel including a total number of cases, a number of treatment plans which are ready, and a number of patients which purchased dental aligners. The management engine 114 may be configured to generate statistics corresponding to conversion rates (e.g., a rate or ratio of patients which purchased dental aligners versus a total number of patients scanned), such as an overall conversion rate, a fast track conversion rate, and a non-fast track conversion rate. The management engine 114 may be configured to generate statistics corresponding to a trend of the overall conversion rate (e.g., a month-to-month conversion rate). The management engine 114 may be configured to generate statistics corresponding to new kit and scan orders, and new aligner orders over a duration (such as over the past 12 weeks). The management engine 114 may be configured to generate, incorporate, or otherwise provide graphics corresponding to the statistics into the report (such as the graphics shown in FIG. 9).

In some embodiments, the management engine 114 may be configured to generate various tables including statistics. The tables may include, for example, a first table on case and aligner orders by location (e.g., by office location). The first table may include various columns of data including a dental office group or affiliation, dental office name or location, total count of cases, count of treatment plans ready, total new aligners ordered, total gross new aligners shipped, count of kit fast-track, count of treatment plans ready (excluding last 7 days), total new aligners ordered (with treatment plans at least 7 days old), conversion percentages (aligners ordered and treatment plans ready), percentage of cases fast tracked, and conversion percentages (with treatment plans at least 7 days old). In some embodiments, the tables may include a second table on new kit and scan orders and aligner orders by week by location over the previous six weeks, etc. For example, the second table may include columns for dental office name or location, and for each of the prior six weeks, a column for total new kits and scans and a column of total new aligners. The management engine 114 may be configured to generate, incorporate, or otherwise provide the tables into the report (such as the graphics shown in FIG. 9).

In some embodiments, the management engine 114 may be configured to generate reports at various recurring intervals (such as daily reports, monthly reports, year-end reports, etc.). Each of the reports may include different information. For example, the daily report may include metrics for the dental office 118, such as those outlined above with respect to FIG. 9. As such, the report shown in FIG. 9 may be a daily report. The monthly report may include metrics for the dental office 118 for the month. In some embodiments, the monthly reports may include metrics for all outstanding cases 204 at the dental office 118. As such, the daily report may include metrics for a single day, whereas the monthly reports may include metrics for all outstanding cases. In some embodiments, the monthly reports may include additional information. In some embodiments, the management engine 114 may be configured to populate the report with additional information, such as an order date, order number, product code (e.g., corresponding to the dental aligners), order status (e.g., complete or in-progress), case status (e.g., treatment underway status), product type (e.g., 22 hour aligners or nighttime aligners), case ID, case number, item number, patient name, shipping region, shipping city, office location, dentist or orthodontist, shipment date, and dental office payment amount. As such, the monthly report may include different information and data from the daily report.

The management engine 114 may be configured to send the reports at the corresponding intervals (e.g., daily reports sent on the same day or the following day, monthly reports sent at the end of the month or the following day, etc.). At each instance in which the management engine 114 generates a new report, the management engine 114 may be configured to retrieve any updated status information for the patient files 115 for including in the report. For example, when the office computing device 116 generates a new case as described above, the management engine 114 may generate a patient file 115 having a first status (such as a patient intake status). On the following day, the management engine 114 may be configured to generate a first report which includes or otherwise identifies metrics corresponding to the new patient file 115 (such as an indication of the patient intake status). When the patient purchases aligners or otherwise begins treatment at a subsequent date, the management engine 114 may be configured to indicate the treatment underway status on any subsequent reports sent to the dental office 118. The treatment underway status may thus indicate that the patient is scheduled to receive dental aligners, the patient received the dental aligners, the dental aligners have been sent to the patient, etc.

In some embodiments, the management engine 114 may generate and send reports to a computing device associated with a dental office 118 (which may be the office computing device 116 or a different computing device). The management engine 114 may be configured to transmit, send, or otherwise provide the report to the dental office 118. For example, the management engine 114 may be configured to send the report to the office computing device 116 for the dental office 118 (such as via the patient intake portal 128 or a dedicated office report portal). In some embodiments, the management engine 114 may be configured to send the report to another computing device associated with the dental office 118 (such as to an email address corresponding to the dental office 118).

Patient Messaging

Figure 10:
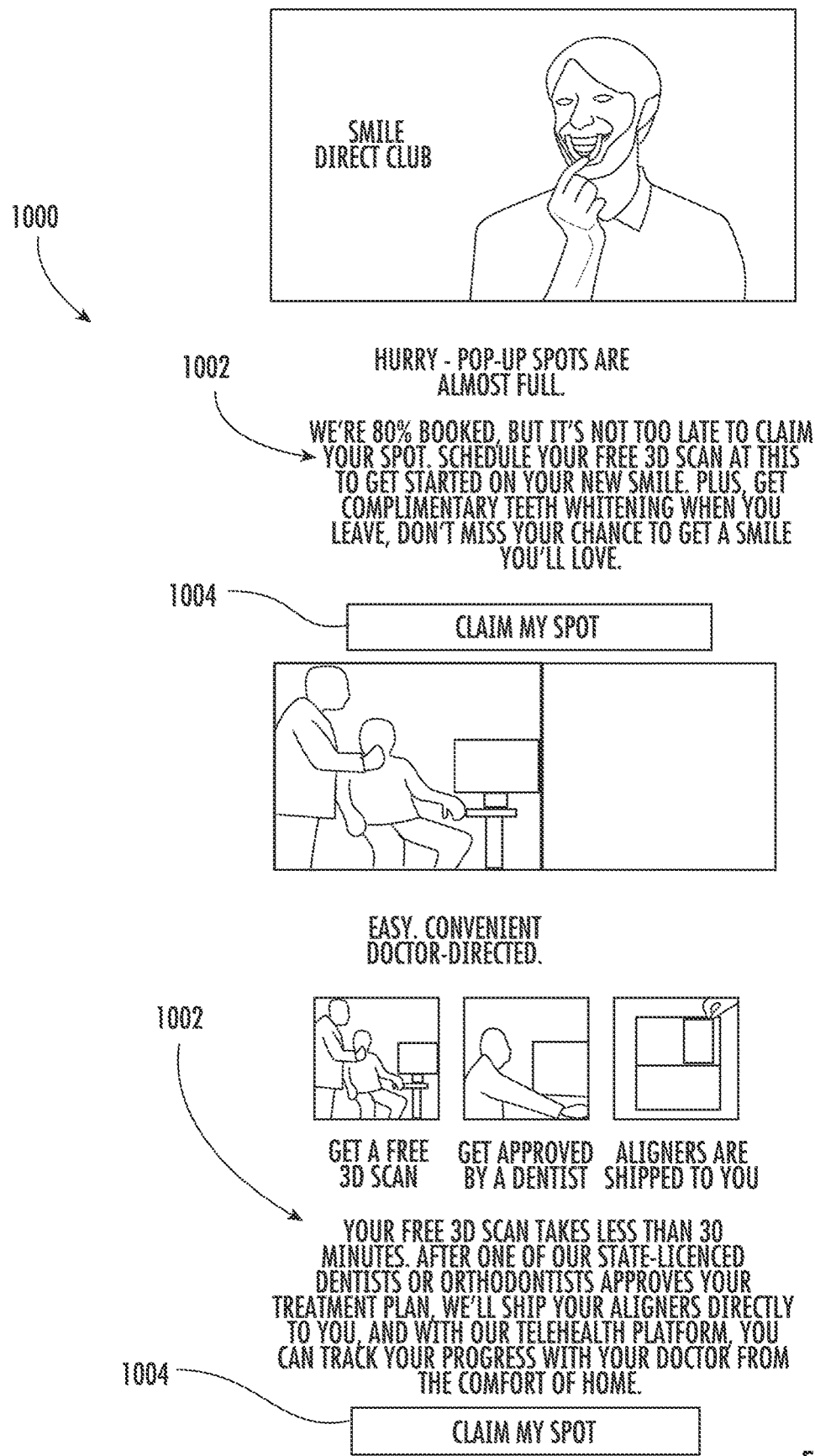
FIG. 10 shows an example notification which may be sent via a messaging system of the system of FIG. 1, according to an illustrative embodiment.

Referring now generally to FIGS. 10-23, one or more computerized methods and processes through which the messaging system 126 provides various notifications (which will be described further herein) about the treatment to the patient 124 are shown according to some embodiments. As a result, the one or more methods and processes of FIGS. 11-23 may be implemented by the messaging system 126 through the communications interface 112. In some embodiments, the notifications may be generated or otherwise maintained by the management engine 114 and stored within the memory 110. The management engine 114 may then populate one or more regions of each notification using information from the patient file maintained by the management engine 114, as well as any other information available to the management engine 114. Once each notification is populated, the communications interface 112 may provide the notification to the patient 124 through the patient computing device 122 in response to a trigger (e.g., a specific date, a specific time, or a specific action (e.g., the patient 124 indicates they received their aligners via the patient computing device 122)). FIG. 10 is an example embodiment of one such notification 1000. The notification 1000 is not meant to be a limiting example of the various notifications, and other notifications may include different regions, fields, headers, and information.

Referring now directly to FIG. 10, the notification 1000 is shown in detail. As shown, the notification 1000 includes one or more regions 1002 and a link 1004. The regions 1002 may be portions of the notification 1000 that are populated via the management engine 114. The management engine 114 may utilize various sets of information at the disposal of the management engine 114 and provide it to the regions 1002. In the example shown, the management engine 114 has populated the regions 1002 with "We're 80% scheduled . . . " In other embodiments, the management engine 114 may utilize information from the patient file and provide it to be displayed to the patient 124 through the notification 1000. The link 1004 may include a URL that is specific to the patient 124 and be selectable such that when the patient 124 selects the link 1004 they are transferred to a specific webpage. In this regard, the notification 1000 and other notifications described herein are configured to be transmitted or sent from the communications interface 112 to the patient computing device 122 to be viewed by the patient 124 on the patient computing device 122. To do so, the communications interface 112 may utilize one or more addresses of the patient computing device 122 (e.g., an email of the patient 124, a phone number of the patient 124, a IP address of the patient 124, etc.).

Referring now to FIG. 11, a method 1100 of confirming an appointment is shown according to an example embodiment. Through the steps of method 1100, the messaging system 126, and more specifically, the communications interface 112 may send one or more notifications (e.g., the notification 1000) to the patient computing device 122 of the patient 124 prior to the appointment of the patient 124.

Method 1100 commences at step 1102 at which the messaging system 126 (e.g., the management engine 114) determines that the patient 124 has scheduled an appointment (e.g., for obtaining an intraoral scan or impressions) and that the patient 124 has provided an email. Based on the appointment and the email of the patient 124, the communications interface 112 generates and provides an appointment confirmation notification to the patient computing device 122 via the email address of the patient 124. In some embodiments, if the patient 124 did not provide an email, but provided a phone number, the method 1100 proceeds to step 1104 at which the communications interface 112 generates and provides the appointment confirmation notification to the patient computing device 122 via the phone number (e.g., via text message, etc.) of the patient 124. The notification generated at step 1104 may include wayfinding information (e.g., such as directions to the dental office, when to leave for the appointment, traffic information corresponding to the route between a location of the patient and the dental office, etc.).

Once the appointment confirmation email has been provided to the patient computing device 122, the method 1100 proceeds to step 1106 at which the messaging system 126 determines if the appointment of the patient 124 is within 2 days. If the appointment is not within 2 days, the method 1100 proceeds to step 1108 at which the messaging system 126 determines if the patient 124 has provided payment information (e.g., a credit card number, a mobile wallet address, etc.). If the patient 124 has provided payment information at step 1108, or if the appointment is within 2 days at step 1106, the method 1100 proceeds to step 1110.

At step 1110, the messaging system 126 generates and provides a "What to Expect" notification to the patient computing device 122 (e.g., via email, SMS, etc.). The "What to Expect" notification may include information and regions regarding the appointment such as the date and time of the appointment and how the process by which a 3D representation of the patient's teeth is obtained (e.g., how an intraoral scan is administered, how impressions are administered, etc.).

Once the "What to Expect" notification has been provided to the patient computing device 122 and a day has passed, the method 1100 proceeds to step 1112 at which a "Before and After" notification is generated and provided to the patient computing device 122 by the messaging system 126. The "Before and After" notification may include information and regions that pertain to what the patient 124 should before the appointment to prepare as well as after the appointment.

Once the "What to Expect" notification has been provided to the patient computing device 122 and a day (i.e., approximately 24 hours) has passed, the method 1100 proceeds to step 1112 at which a "Before and After" notification is generated and provided to the patient computing device 122 by the messaging system 126. The "Before and After" notification may include information and regions that pertain to other patients which have received treatment (such as before and after photographs, text including patient's experiences with treatment, patient reviews, etc.).

Once the "Before and After" notification has been provided to the patient computing device 122 and a day has passed, the method 1100 proceeds to step 1114 at which a "Bright On" notification is generated and provided to the patient computing device 122 by the messaging system 126. The "Bright On" notification may include information such as an advertisement that relates to teeth whitening as well as any other information the patient 124 may need to prepare for their appointment.

Once the "Bright On" notification has been provided to the patient computing device 122 and two days have passed, the method 1100 proceeds to step 1114 at which a "Doctor's Note" notification is generated and provided to the patient computing device 122 by the messaging system 126. The "Doctor's Note" notification may include information from a doctor that provides additional information on the patient intake process, such as what the patient should expect.

Going back to step 1108, if it is determined that the patient 124 has not entered their payment information, the method 1100 proceeds to step 1118 at which the "What to Expect" notification is generated and provided to the patient computing device 122 by the messaging system 126. Step 1118 may be substantially the same as step 1110. Once the "What to Expect notification" has been provided to the patient computing device 122 and a day has passed, the method 1100 proceeds to step 1120 at which a payment information request notification is generated and provided to the patient computing device 122 by the messaging system 126. The payment information request notification may include one or more links through which the patient 124 can select and then enter their payment information and request that the patient 124 do so before their appointment.

Once the payment information request has been provided to the patient computing device 122 and a day has passed, the method 1100 proceeds to step 1122 at which a "Before and After" notification is generated and provided to the patient computing device 122 by the messaging system 126. Once the "Before and After" notification is generated and provided to the patient computing device 122 by the messaging system 126 and two days have passed, the method 1100 proceeds to step 1124 at which a "Bright On" notification is generated and provided to the patient computing device 122 by the messaging system 126.

Next, the method proceeds to step 1126 or step 1130, depending on a logic plum score of the patient 124. The logic plum score may be a score developed using an artificial intelligence or machine learning model that indicates the likelihood a patient 124 will show up to their appointment. In other embodiments, the logic plum score may indicate the likelihood a patient 124 will start the treatment process after their appointment or will eventually complete the treatment process. Furthermore, the logic plum score may be kept within the memory 110 and accessed by the management engine 114 when required. If, at step 1124, it is determined that the patient 124 does not have a logic plum score, the method 1100 proceeds to step 1126 and then step 1116 at which the "Doctor's Note" notification is provided to the patient computing device 122.

Once the "Doctor's Note" notification has been provided to the patient computing device 122 and two days have passed, the method 1100 proceeds to step 1128 at which a "Social Sharing" notification is generated and provided to the patient computing device 122 by the messaging system 126. The "Social Sharing" notification may include one more links and regions that request the patient 124 share their appointment experience with others via social media. In some embodiments, the "Social Sharing" notification may offer the patient 124 a financial incentive if they share their appointment experience with others via social media.

In comparison, at step 1124, if is determined that the patient 124 has a logic plum score the method 1100 proceeds to step 1130 and then step 1132. At step 1132, the messaging system 126 determines if the patient 124 is four or more days away from their appointment. If the patient 124 was four or more days away from their appointment and a day has passed, the method 1100 proceeds to at least one of step 1134 or step 1136, depending on the logic plum score of the patient 124.

If at step 1132 it is determined the patient has a low to medium logic plum score (e.g., 0-60 on a 100 scale), the method proceeds to step 1134 at which another appointment confirmation notification is generated and provided to the patient computing device 122 by the messaging system 126. If at step 1132 it is determined the patient has a medium to high logic plum score (e.g., 61-100 on a 100 scale), the method proceeds to step 1136 at which an "Unforgettable" notification is generated and provided to the patient computing device 122 by the messaging system 126. The "Unforgettable" notification may provide the patient 124 with additional incentives or offers (e.g., gift card, coupon for aligners, free teeth whitening kit, etc.) for attending their appointment.

After either of steps 1134 and 1136 have occurred and a day has passed, the method 1100 proceeds to step 1138 at which a "Doctor's Note" notification is generated and provided to the patient computing device 122 by the messaging system 126. Additionally, after step 1138 has occurred and two days have passed, the method 1100 proceeds to step 1140 at which a "Social Sharing" notification is generated and provided to the patient computing device 122 by the messaging system 126.

Referring now to FIG. 12 a method 1200 for providing a personalized notification to the patient 124 before their appointment is shown according to an example embodiment. As described herein, the steps of the method 1200 may be performed by the many components of the messaging system 126 (e.g., the communication interface 112, the management engine 114, etc.). The method 1200 commences at step 1202 at which it is determined if the appointment of the patient 124 is over seven days away. If the appointment of the patient is over seven days away, the method 1200 proceeds to step 1204 at which a personalized notification from an office administrator (e.g., a staff member associated with the appointment) is generated and sent to the patient 124. In some embodiments, the personalized notification may be generated by the messaging system 126 and provided to the patient computing device 122. In other embodiments, the personalized notification may be generated by the office administrator, in response to a reminder from the messaging system 126, printed, and mailed to the patient 124.

Figure 13:
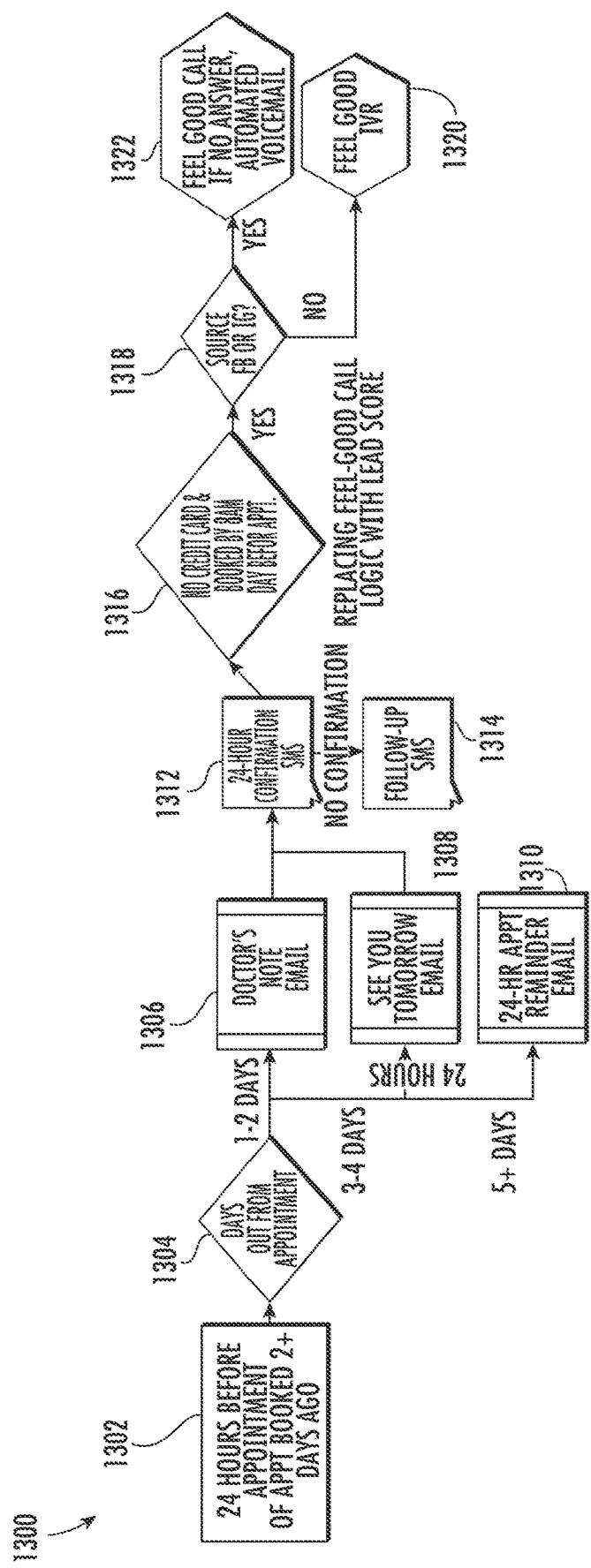
FIG. 13 is a flowchart showing a second messaging process for messaging a patient prior to a scheduled appointment and providing notifications to the patient, according to an illustrative embodiment.

Referring to FIG. 13, a method 1300 of confirming an appointment of the patient 124 and providing notifications to the patient 124 on the days before the appointment is shown according to an example embodiment. Through the method 1300, the components of the messaging system 126 provide one or more notifications to the patient 124 about their upcoming appointment. As compared to the methods 1100 and 1200, the method 1300 focuses on reminding the patient 124 of their appointment to generally increase appointment attendance. The method 1300 commences at step 1302 at which the messaging system 126 determines if the appointment of the patient 124 is over a day away and was scheduled two or more days ago. If the appointment of the patient 124 is over a day away and was scheduled two or more days ago, the method 1300 proceeds to step 1304 at which the numbers of days until the appointment of the patient 124 are determined by the messaging system 126. At step 1304, the messaging system 126 may determine the numbers of days until the appointment of the patient 124 by subtracting the current date from the date of the appointment and then rounding the solution up (e.g., 2.4 days=3 days).

Once the number of days until the appointment of the patient has been determined, the method 1300 proceeds to at least one of step 1306, step 1308, and step 1310, depending on the number of days until the appointment of the patient 124. For example, if the messaging system 126 determined the number of days until the appointment is 1-2 and a day has passed, the method 1300 may proceed to step 1306 at which a "Doctor's Note" notification (which may be substantially the same as the "Doctor's Note" notification described with regard to the method 1200) is generated and provided to the patient computing device 122 by the messaging system 126. Similarly, if the messaging system 126 determined the number of days until the appointment is 3-4 and a day has passed, the method 1300 may proceed to step 1308 at which a "See You Tomorrow" notification is generated and provided to the patient computing device 122 by the messaging system 126. The "See You Tomorrow" notification may be a reminder notification that is provided to the patient 124 to remind the patient 124 to show up to their appointment. Additionally, at step 1304, if the messaging system 126 determined the number of days until the appointment is 5 or more and a day has passed, the method 1300 may proceed to step 1310 at which a "24 Hour Reminder" notification is generated and provided to the patient computing device 122 by the messaging system 126. The "24 Hour Reminder" notification may include details regarding the appointment of the patient 124 such as the location, time, and date of the appointment and be configured to serve as a continual reminder of the appointment.

Once the messaging system 126 has completed steps 1306 and 1308, the method 1300 may proceed to step 1312 at which a "24 Hour Confirmation" notification is provided to the patient computing device 122 by the messaging system 126. The "24 Hour Confirmation" notification may include information relating to the appointment of the patient 124 as well as request that the patient 124 select one or more links or other selectable indicators that they are able and will make their appointment (i.e., provide confirmation). If no confirmation is received from the patient 124 via the patient computing device 122 once the "24 Hour Confirmation" notification has been provided (e.g., within four or more hours from the "24 Hour Confirmation" notification being provided), the method 1300 proceeds to step 1314 at which a follow-up notification is generated and provided to the patient computing device 122 by the messaging system 126. The follow up notification may serve as a reminder to the patient 124 of the appointment or may also request confirmation that the patient 124 is able and will make their appointment.

In comparison, at step 1312, if confirmation is received the method 1300 may proceed to step 1316. At step 1316, the messaging system 126 determines if the patient 124 has provided payment information and if the patient 124 scheduled before 8 AM of the day before the appointment. If the patient 124 has not provided payment information and scheduled by 8 AM of the day before their appointment, the method 1300 proceeds to step 1318. At step 1318, the messaging system 126 determines the source (e.g., the website, the application, the place) through which the patient 124 scheduled their appointment, and specifically if the appointment of the patient 124 was scheduled through Facebook® or Instagram®. If the appointment of the patient 124 was not scheduled through Facebook® or Instagram®, the method 1300 proceeds to step 1320. At step 1320, the messaging system 126 generates and provides a "Feel Good" interactive voice response (IVR) to the patient computing device 122 of the patient. The "Feel Good" IVR may be configured to provide the patient 124 with information pertaining to their appointment while allowing the patient 124 to ask questions about the appointment. In comparison, at step 1318, if the appointment of the patient 124 was scheduled through Facebook® or Instagram®, the method 1300 proceeds to step 1322. At step 1322 a "Feel Good" call is provided to the patient computing device 122 by a live person. The person may provide the patient 124 with any answers to questions they may have about their appointment.

Figure 14:
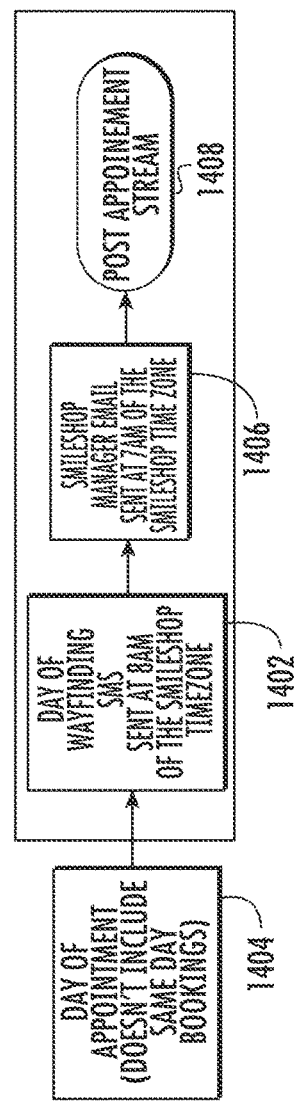
FIG. 14 is a flowchart showing a method of providing notifications to the patient on the day of their scheduled appointment, according to an illustrative embodiment.

Referring now to FIG. 14, a method 1400 of providing notifications to the patient 124 on the day of their appointment is shown according to an example embodiment. Through the steps of the method 1400, the messaging system 126 may communicate with and provide notifications to the patient computing device 122 and the patient 124 on the day of the appointment of the patient 124. The method 1400 commences at step 1402 at which the messaging system 126 determines if it is the day of the appointment of the patient 124. Furthermore, at step 1402, the messaging system 126 determines if the patient 124 scheduled the appointment on the day of the appointment (i.e., a same day booking). If it is determined to the day of the appointment and the patient 124 did not schedule a same day booking, the method 1400 proceeds to step 1404.

At step 1404, the messaging system 126 generates and provides a "Day-of Wayfinding" notification to the patient computing device 122 at 8 AM, local time of the appointment. The "Day-of Wayfinding" notification may include general or specific directions to the appointment, parking information, and any other information the patient 124 may require to reach their appointment. Once the "Day-of Wayfinding" notification has been provided to the patient computing device 122, the method 1400 may proceed to step 1406 at which a personalized notification is provided to the patient computing device 122. In some embodiments, the personalized notification may be generated and provided by an appointment manager. In other embodiments, the personalized notification may be generated and provided by the messaging system 126. Furthermore, in some embodiments, step 1406 takes place prior to step 1404 and is transmitted or sent to the patient computing device 122 at 7 AM, local time of the appointment. Finally, after the personalized notification is provided to the patient computing device 122 and the messaging system 126 determines the appointment of the patient 124 has occurred, the method 1400 proceeds to step 1408 at which a method similar to method 1600 corresponding to post-appointment messaging occurs.

Referring now to FIG. 15A, a method 1500 of providing multiple notifications to patients who schedule their appointment three or more days before the appointment is to take place is shown according to an example embodiment. The method 1500 commences at step 1502 at which the messaging system 126 determines that the appointment of the patient was scheduled with three or more days from the date of scheduling the appointment to the date of the appointment itself. Furthermore, at step 1502, an appointment confirmation notification (which may be substantially the same as the appointment confirmation notification of the method 1100) is generated and provided to the patient computing device 122 by the messaging system 126. In further embodiments, one or more advertisements (e.g., an AMAZON banner) may be provided to the patient computing device 122 by the messaging system 126 at step 1502.

In some embodiments, if the patient 124 does not provide confirmation in response to the appointment confirmation notification, the method 1500 proceeds to step 1504 at which a follow up appointment confirmation is generated and provided to the patient computing device 122 by the messaging system 126. In some embodiments, the follow up appointment confirmation notification and the appointment confirmation notification are provided to two different addresses of the patient computing device 122 (e.g., an email and a phone number, an email and a IP address, etc.). In even other embodiments, the follow up appointment confirmation may be provided to the patient computing device 122 regardless if the patient 124 provides confirmation or not.

Once the messaging system 126 has provided the appointment confirmation notification at step 1502 and/or approximately one hour has passed, the method 1500 proceeds to step 1506 at which a "What to Expect" notification (which may be substantially the same as the "What to Expect" notification of the method 1100) is generated and provided to the patient computing device 122 by the messaging system 126. Furthermore, at step 1506 an advertisement may be generated and provided to the patient computing device 122 by the messaging system 126. In some embodiments, additional advertisements are not generated at step 1506 but rather the same advertisement from step 1502 is continually provided to the patient computing device 122.

Once the "What to Expect" notification has been generated and provided at step 1506 and a day has passed, the method 1500 proceeds to step 1508 at which a promotion notification is generated and provided to the patient computing device 122 by the messaging system 126. The promotion notification may include one or more promotions (e.g., gift card offers, reduced price on aligners, promotional values on other devices, etc.) that are included within the notification. In some embodiments, the promotions may require the patient 124 to provide certain information (e.g., payment information) or purchase certain items (e.g., purchase a full aligner treatment package, etc.).

Once the promotion notification has been generated and provided to the patient computing device 122, the method 1500 proceeds to step 1510 at which any other pre-appointment notifications or information requests are provided to the patient computing device 122 by the messaging system 126. For example, step 1510 may immediately proceed the method 1400, the method 1300, or any other pre-appointment methods through which one or more pre-appointment notifications are provided to the patient computing device 122.

Referring now to FIG. 15B, a method 1511 of providing multiple notifications to patients who schedule their appointment two days before the appointment is to take place is shown according to an example embodiment. The method 1511 commences at step 1512 at which the messaging system 126 determines that the appointment of the patient was scheduled with two days from the date of scheduling the appointment to the date of the appointment itself. Furthermore, at step 1512, an appointment confirmation notification (which may be substantially the same as the appointment confirmation notification of the method 1100) is generated and provided to the patient computing device 122 by the messaging system 126. In further embodiments, one or more advertisements (e.g., an AMAZON banner, a directed advertisement, etc.) may be provided to the patient computing device 122 by the messaging system 126 at step 1512.

In some embodiments, if the patient 124 does not provide confirmation in response to the appointment confirmation notification, the method 1511 proceeds to step 1514 at which a follow up appointment confirmation is generated and provided to the patient computing device 122 by the messaging system 126. In some embodiments, the follow up appointment confirmation notification and the appointment confirmation notification are provided to two different addresses of the patient computing device 122 (e.g., an email and a phone number, an email and an IP address, etc.). In even other embodiments, the follow up appointment confirmation may be provided to the patient computing device 122 regardless if the patient 124 provides confirmation or not.

Once the messaging system 126 has provided the appointment confirmation notification at step 1512 and/or approximately one hour has passed, the method 1511 proceeds to step 1516 at which a "What to Expect" notification (which may be substantially the same as the "What to Expect" notification of the method 1100) is generated and provided to the patient computing device 122 by the messaging system 126. Furthermore, at step 1516 an advertisement may be generated and provided to the patient computing device 122 by the messaging system 126. In some embodiments, additional advertisements are not generated at step 1516 but rather the same advertisement from step 1512 is continually provided to the patient computing device 122.

Once the "What to Expect" notification has been generated and provided at step 1516 and a day has passed, the method 1511 proceeds to step 1518 at which a promotion notification is generated and provided to the patient computing device 122 by the messaging system 126. The promotion notification may include one or more promotions (e.g., gift card offers, reduced price on aligners, promotional values on other devices, etc.) that are included within the notification. In some embodiments, the promotions may require the patient 124 to provide certain information (e.g., payment information) or purchase certain items (e.g., purchase a full aligner treatment package, etc.).

Once the promotion notification has been generated and provided at step 1518, the method 1511 proceeds to step 1520 at which a "24 Hour Confirmation" notification (which may be substantially the same as the "24 Hour Confirmation" notification of the method 1300) is generated and provided to the patient computing device 122 by the messaging system 126. Similar to step 1512 and 1516, the messaging system 126 may also generate and provide one or more advertisements to the patient computing device 122 at step 1520.

In some embodiments, if the patient 124 does not provide confirmation in response to the "24 Hour Confirmation" notification, the method 1511 proceeds to step 1522 at which a follow up "24 Hour Confirmation" notification is generated and provided to the patient computing device 122 by the messaging system 126. In some embodiments, the follow up "24 Hour Confirmation" notification and the "24 Hour Confirmation" notification are provided to two different addresses of the patient computing device 122 (e.g., an email and a phone number, an email and an IP address, etc.). In even other embodiments, the follow up "24 Hour Confirmation" may be provided to the patient computing device 122 regardless if the patient 124 provides confirmation or not.

In some embodiments, if the patient 124 does not provide confirmation in response to the follow up "24 Hour Confirmation" notification, the method 1511 proceeds to step 1524 at which a "Feel Good" call or a "Feel Good" IVR (which may be substantially the same as the "Feel Good" call and "Feel Good" IVR discussed with respect to the method 1300) is generated and provided to the patient computing device 122 by the messaging system 126 or by a staff member associated with the appointment.

Once the messaging system 126 has provided the "24 Hour Confirmation" notification at step 1520, the method 1511 proceeds to step 1526 at which a "24 Hour Reminder" notification (which may be substantially the same as the "24 hour Reminder" Notification of the method 1300) is generated and provided to the patient computing device 122 by the messaging system 126. Furthermore, at step 1526 a "Doctor's Note" notification (which may be substantially the same as the "Doctor's Note notification of the method 1100) may be generated and provided in tandem with, combined and provided with, or generated and provided separately to the "24 Hour Reminder" notification.

Once the messaging system 126 has provided the "24 Hour Reminder" notification and the "Doctor's Note" notification at step 1526, the method 1511 may proceed to step 1528 at which a personalized notification (which may be substantially the same as the personalized notification from the method 1400) from an office administrator (e.g., a staff member associated with the appointment) is generated and sent to the patient 124. In some embodiments, the personalized notification may be generated by the messaging system 126 and provided to the patient computing device 122. In other embodiments, the personalized notification may be generated by the office administrator, in response to a reminder from the messaging system 126, printed, and provided to the patient 124 by the office administrator. Furthermore, at step 1526 one or more advertisements may be generated and provided to the patient computing device 122 by the messaging system 126.

Once the personalized notification has been provided to the patient 124 at step 1528, the method 1511 may proceed to step 1530 at which the messaging system 126 generates and provides a "Day-of Wayfinding" notification to the patient computing device 122 at 8 AM, local time of the appointment. The "Day-of Wayfinding" notification may be similar to the "Day-of Wayfinding" notification of the method 1400.

Figure 15C:
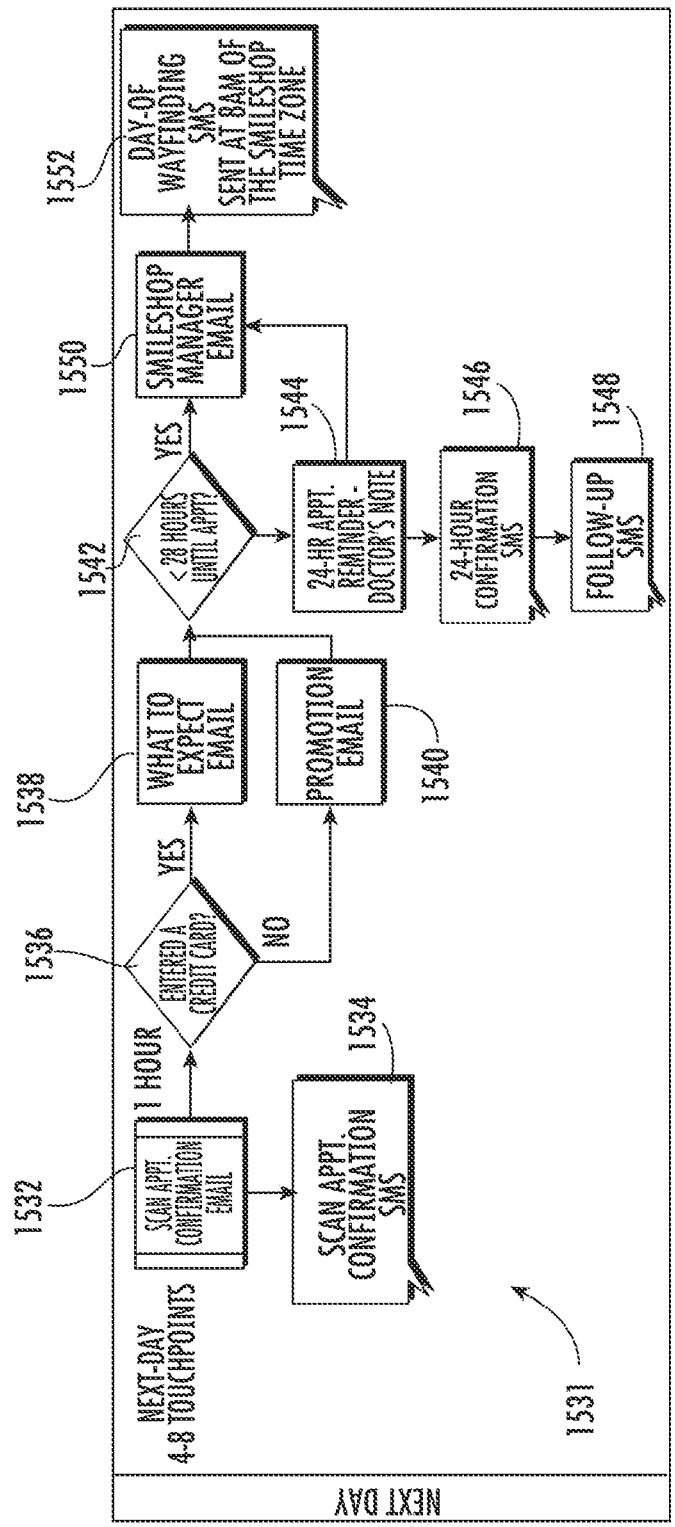

Referring now to FIG. 15C, a method 1531 of providing multiple notifications to patients who schedule their appointment one day before the appointment is to take place is shown according to an example embodiment. The method 1531 commences at step 1532 at which the messaging system 126 determines that the appointment of the patient was scheduled with one day from the date of scheduling the appointment to the date of the appointment itself. At step 1532, an appointment confirmation notification (which may be substantially the same as the appointment confirmation notification of the method 1100) is generated and provided to the patient computing device 122 by the messaging system 126.

In some embodiments, if the patient 124 does not provide confirmation in response to the appointment confirmation notification, the method 1531 proceeds to step 1534 at which a follow up appointment confirmation is generated and provided to the patient computing device 122 by the messaging system 126. In some embodiments, the follow up appointment confirmation notification and the appointment confirmation notification are provided to two different addresses of the patient computing device 122 (e.g., an email and a phone number, an email and a IP address, etc.). In even other embodiments, the follow up appointment confirmation may be provided to the patient computing device 122 regardless if the patient 124 provides confirmation or not.

Once the messaging system 126 has provided the appointment confirmation notification at step 1532 and/or approximately one hour has passed, the method 1531 proceeds to step 1536 at which the messaging system 126 determines if payment information has been received from the patient 124. If payment information has been received from the patient 124, the method 1531 proceeds to step 1538 at which a "What to Expect" notification (which may be substantially the same as the "What to Expect" notification of the method 1100) is generated and provided to the patient computing device 122 by the messaging system 126. If payment information has not been received from the patient 124 at step 1536, the method 1531 proceeds to step 1540 at which a promotion notification is generated and provided to the patient computing device 122. The promotion notification may be similar or the same as the promotion notification of step 1508.

Once either one of steps 1538 and 1540 have been completed, the method 1531 proceeds to step 1542 at which the messaging system 126 determines if there is less than 28 hours until the appointment of the patient. If the messaging system 126 determines there is more than or is 28 hours until the appointment of the patient, the method 1531 proceeds to step 1544 at which a "24 Hour Reminder" notification (which may be substantially the same as the "24 hour Reminder" Notification of the method 1300) is generated and provided to the patient computing device 122 by the messaging system 126. Furthermore, at step 1544 a "Doctor's Note" notification (which may be substantially the same as the "Doctor's Note notification of the method 1100) may be generated and provided in tandem with, combined and provided with, or generated and provided separately to the "24 Hour Reminder" notification.

Once the "24 Hour Reminder" notification and/or the "Doctor's Note" notification have been generated and provided to the patient computing device 122 by the messaging system 126, the method 1531 proceeds to step 1546 at which a "24 Hour Confirmation" notification (which may be substantially the same as the "24 Hour Confirmation" notification of the method 1300) is generated and provided to the patient computing device 122 by the messaging system 126.

In some embodiments, if the patient 124 does not provide confirmation in response to the "24 Hour Confirmation" notification, the method 1531 proceeds to step 1548 at which a follow up "24 Hour Confirmation" notification is generated and provided to the patient computing device 122 by the messaging system 126. In some embodiments, the follow up "24 Hour Confirmation" notification and the "24 Hour Confirmation" notification are provided to two different addresses of the patient computing device 122 (e.g., an email and a phone number, an email and a IP address, etc.). In even other embodiments, the follow up "24 Hour Confirmation" may be provided to the patient computing device 122 regardless if the patient 124 provides confirmation or not.

In comparison, if, at step 1542, it is determined that there is less than 28 hours until the appointment of the patient 124 or after step 1544, the method 1531 proceeds to step 1550 at which a personalized notification (which may be substantially the same as the personalized notification from the method 1400) from an office administrator (e.g., a staff member associated with the appointment) is generated and sent to the patient 124. In some embodiments, the personalized notification may be generated by the messaging system 126 and provided to the patient computing device 122. In other embodiments, the personalized notification may be generated by the office administrator, in response to a reminder from the messaging system 126, and provided to the patient computing device 122 by the office administrator.

Once the personalized notification has been provided to the patient 124 at step 1528, the method 1531 may proceed to step 1552 at which the messaging system 126 generates and provides a "Day-of Wayfinding" notification to the patient computing device 122 at 8 AM, local time of the appointment. The "Day-of Wayfinding" notification may be similar to the "Day-of Wayfinding" notification of the method 1400.

Figure 15D:
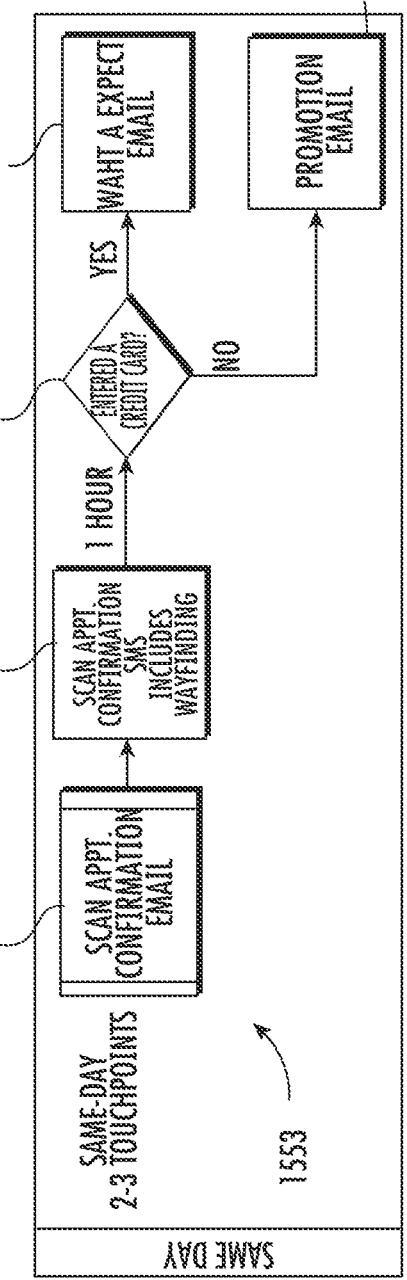

Referring now to FIG. 15D, a method 1553 of providing multiple notifications to patients who schedule their appointment on the same day as the appointment is to take place is shown according to an example embodiment. The method 1553 commences at step 1554 at which the messaging system 126 determines that the appointment of the patient was scheduled on the day of the appointment itself. At step 1553, an appointment confirmation notification (which may be substantially the same as the appointment confirmation notification of the method 1100) is generated and provided to the patient computing device 122 by the messaging system 126.

Once the messaging system 126 provides the appointment confirmation notification at step 1554, the method 1553 proceeds to step 1556 at which a follow up appointment confirmation is generated and provided to the patient computing device 122 by the messaging system 126. In some embodiments, the follow up appointment confirmation notification and the appointment confirmation notification are provided to two different addresses of the patient computing device 122 (e.g., an email and a phone number, an email and a IP address, etc.). The follow-up appointment confirmation notification may include day-of wayfinding information, which may be similar to the day-of wayfinding information described above.

Once the messaging system 126 has provided the follow up appointment confirmation notification at step 1556 and one hour has passed, the method 1553 proceeds to step 1558 at which the messaging system 126 determines if payment information has been received from the patient 124. If payment information has been received from the patient 124, the method 1553 proceeds to step 1560 at which a "What to Expect" notification (which may be substantially the same as the "What to Expect" notification of the method 1100) is generated and provided to the patient computing device 122 by the messaging system 126. If payment information has not been received from the patient 124 at step 1558, the method 1553 proceeds to step 1560 at which a promotion notification is generated and provided to the patient computing device 122. The promotion notification may be similar or the same as the promotion notification of step 1508.

Figure 16:
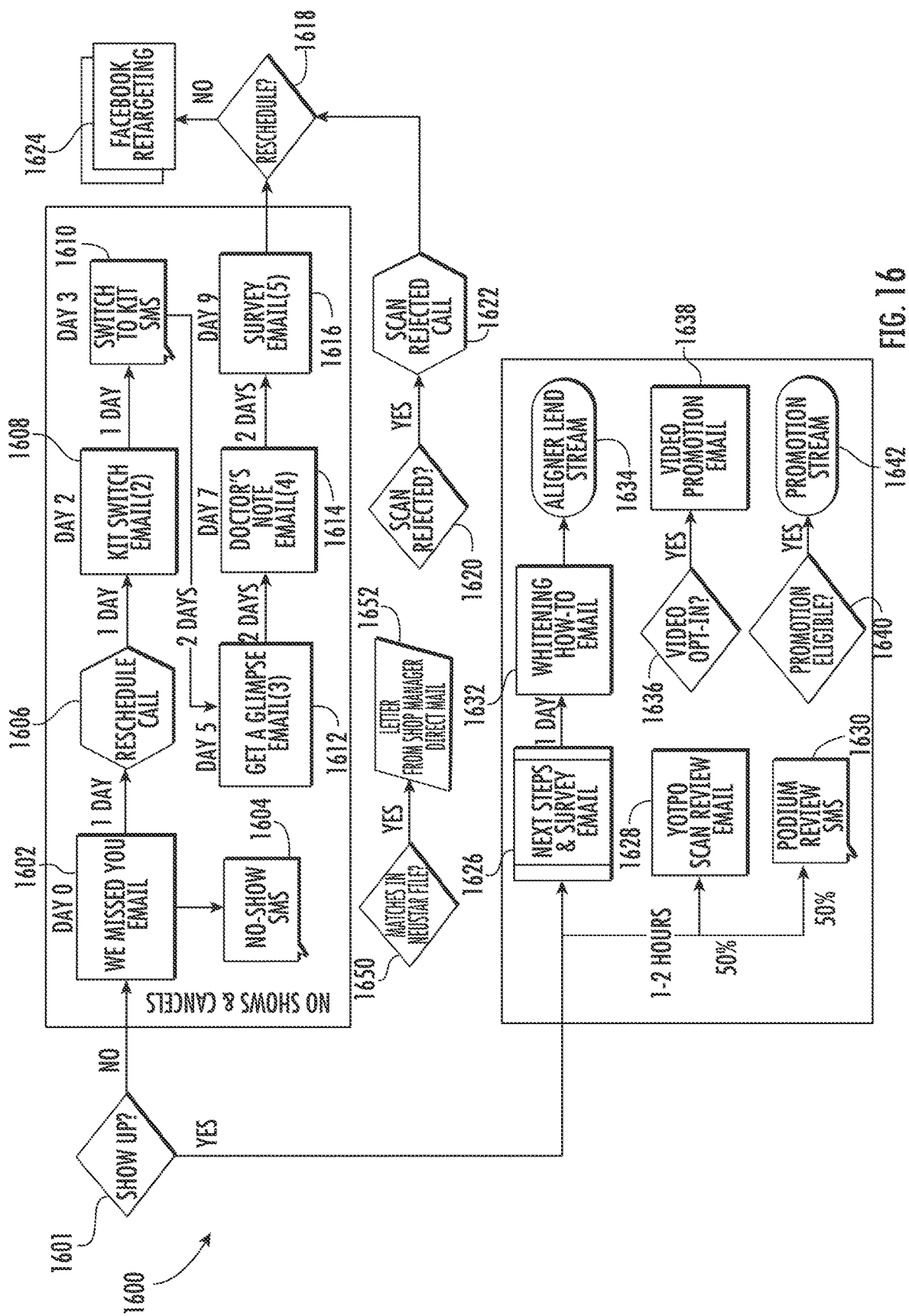
FIG. 16 is a flowchart showing a method of following up with and providing notifications to the patient after their scheduled appointment, according to an illustrative embodiment.

Referring now to FIG. 16, a method 1600 of following up with and providing notifications to the patient 124 after their scheduled appointment is shown according to an example embodiment. The method 1600 commences at step 1601 at which the messaging system 126 determines if the patient 124 attended their appointment or did not show up or call to reschedule. The management engine 114 may determine whether the patient 124 attended their appointment based on data included in the patient file 115 (e.g., and received via the patient intake portal 128 from the office computing device 116). If the messaging system 126 determines that the patient did not attend their appointment and did not call to reschedule the appointment, the method 1600 proceeds to step 1602 at which a "We missed you" notification is generated and provided to the patient computing device 122 by the messaging system 126. The "We missed you" notification may provide a general indication of the missed appointment as well as information on or a link to reschedule the appointment for a future date. Furthermore, once the "We missed you" notification has been provided to the patient computing device 122, the method 1600 may proceed to step 1604 at which a "No-show" notification is generated and provided to the patient computing device 122 by the messaging system 126. The "No-show" notification may include an information request on why the patient 124 missed their appointment as well as corrective actions that may be required of the patient 124. In some embodiments, the "We missed you" notification and the "No-show" notification may be provided to two different addresses of the patient computing device 122.

Once the messaging system 126 has provided the "We missed you" notification at step 1602 and/or approximately one day has passed, the method 1600 proceeds to step 1606 at which a "Reschedule" notification is generated and provided to the patient computing device 122 by the messaging system 126. The "Reschedule" notification may request the patient 124 to reschedule their appointment for a convenient time and may include one or more selectable links that navigate the patient computing device 122 to a scheduling service. In some embodiments, the "Reschedule" notification may be a phone call that is performed by a staff member associated with the appointment.

Once the messaging system 126 has provided the "Reschedule" notification at step 1606 and/or approximately one day has passed, the method 1600 proceeds to step 1608 at which a "Kit Switch" notification is generated and provided to the patient computing device 122 by the messaging system 126. The "Kit Switch" notification may include an offer to receive a dental impression kit (which can be used in place of the scan to generate a treatment plan for their patient 124) and request information such as the address of the patient 124 and the payment information of the patient 124 to pay for the impression kit. In some embodiments, the "Kit Switch" notification may include additional details about how the impression kit works as well as a link to purchase or receive the impression kit.

Once the messaging system 126 has provided the "Kit Switch" notification at step 1608 and/or approximately one day has passed, the method 1600 proceeds to step 1610 at which a follow up "Kit Switch" notification is generated and provided to the patient computing device 122 by the messaging system 126. The follow up "Kit Switch" notification may be similar to the "Kit Switch" notification but may be provided to a different address of the patient computing device 122 (e.g., a phone number of the patient 124 as compared to an email of the patient 124).

Once the messaging system 126 has provided the follow up "Kit Switch" notification at step 1610 and/or approximately two days have passed, the method 1600 proceeds to step 1612 at which a "Get a Glimpse" notification is generated and provided to the patient computing device 122 by the messaging system 126. The "Get a Glimpse" notification may include one or more examples of patients who have successfully completed treatment as well as additional details about the treatment procedure. In some embodiments, the "Get a Glimpse" notification may request and include a link to reschedule the appointment.

Once the messaging system 126 has provided the "Get a Glimpse" notification at step 1612 and/or approximately two days have passed, the method 1600 proceeds to step 1614 at which a "Doctor's Note" notification (which may be substantially the same as the "Doctor's Note notification of the method 1100) is generated and provided to the patient computing device 122 by the messaging system 126.

Once the messaging system 126 has provided the "Doctor's Note" notification at step 1614 and/or approximately two days have passed, the method 1600 proceeds to step 1616 at which a survey notification is generated and provided to the patient computing device 122 by the messaging system 126. The survey notification may include a link to and request the patient 124 to fill out a survey relating to their experience and the appointment scheduling experience, such as why the patient 124 missed their appointment, things the patient 124 would change about the appointment scheduling, etc.

Once the messaging system 126 has provided the survey notification at step 1616, the method 1600 proceeds to step 1618 at which the messaging system 126 determines whether the patient has rescheduled an appointment. If the patient has rescheduled their appointment, the method 1600 may proceed to one or more of the pre-appointment messaging methods described above.

Similarly, if at step 1601 it is determined that the patient 124 showed up to their appointment, the method 1600 may proceed to step 1620 at which the messaging system 126 determines if the 3D model of the patient 124 obtained during the patient intake at the appointment was rejected (or receives indication of such). If, at step 1620, the messaging system 126 determines the 3D model of the patient 124 was rejected (or receives an indication of such), the method may proceed to step 1622 at which a "Scan Rejected" notification is generated and provided to the patient computing device 122 by the messaging system 126. The "Scan Rejected" notification may include details about why the 3D model of the patient 124 was rejected, as well as how to remedy the rejected scan. In some embodiments, the "Scan Rejected" notification is a phone call from a staff member associated with the appointment. Once the "Scan Rejected" notification is provided to the patient computing device 122, the method 1600 proceeds to step 1618, which is described herein.

Once the messaging system 126 has provided the "Reschedule" notification at step 1618 and an indication has been received that the patient 124 will not reschedule, the method 1600 proceeds to step 1624 at which the messaging system provides or indicates to another component to provide advertisements (e.g., Facebook® advertisements, Amazon® advertisements, etc.) to the patient computing device 122.

In some embodiments, at step 1601, if it is determined the patient 124 showed up to their appointment and/or the 3D model of the patient 124 was accepted the method 1600 proceeds to step 1626 as well as one or more of steps 1628 and 1630. At step 1626, the messaging system 126 generates and provides a "Next Steps" notification to the patient computing device 122. The "Next Steps" notification may include about the next steps forward in the treatment process, estimated time for a treatment plan to be generated, estimated time for aligners to be created, etc. Similarly, at step 1626, the messaging system 126 may generate and provide a survey notification to the patient computing device 122. In some embodiments, the survey notification and the "Next Steps" notification are a single, combined, notification. The survey notification may include a link to and request the patient 124 to fill out a survey relating to their appointment experience. Similarly, after step 1601 has occurred and 1-2 hours have passed, the method 1600 may proceed to at least one of step 1628 and step 1630. In some embodiments, the messaging system 126 picks at random between step 1628 and step 1630 with an even chance of picking either (e.g., 50% chance of proceeding to step 1628 and 50% chance of proceeding to step 1630). At steps 1628 and 1630, additional survey notifications (e.g., a YOTPO survey and a PODIUM survey) may be generated and provided to the patient computing device 122 by the messaging system 126.

Once the messaging system 126 has provided the survey notification at step 1626 and a day has passed, the method 1600 proceeds to step 1632 at which the messaging system 126 generates and provides a "Whitening How-to" notification to the patient computing device 122. The "Whitening How-to" notification may include a product offer (i.e., an offer to purchase) for a teeth whitening device as well as one or more details about how to use the teeth whitening device. In other embodiments, the "Whitening How-to" notification may include additional information on how to naturally whiten teeth.

Once the messaging system 126 has provided the "Whitening How-to" notification at step 1632, the method 1600 proceeds to step 1634 at which the messaging system 126 generates and provides one or more notifications about possible aligners of the patient 124. For example, at step 1634 another method may proceed or other steps described herein may proceed that provide the patient notification about possible aligners, the fabrication process, purchasing a treatment plan, etc. For example, at step 1634, the method 1600 may proceed to step 1636 or step 1640.

At step 1636, it is determined, by the messaging system 126, if an indication has been received that the patient 124 has opted in to receiving videos (e.g., via email, phone, on social media, etc.). If the indications that the patient 124 has opted into receiving videos, the method 1600 may proceed to step 1638 at which a video promotion notification is generated and provided to the patient computing device 122 by the messaging system 126. The video promotion notification may be similar to other promotion notifications described herein and be in a video format. In one example, the video promotion notification may provide the patient 124 with possible promotions (e.g., gift cards, percent off treatment, etc.), if the patient 124 generates and provides a video that is received by the messaging system 126. In some embodiments, the video may also be posted on social media to receive the promotion offer.

In comparison, at step 1640, it is determined, by the messaging system 126, if the patient 124 is eligible for promotions. For example, the patient 124 may be eligible if they have opted into the video at step 1636, if the patient 124 has provided positive feedback (e.g., via the survey notifications), or via other indications that indicate the patient 124 has qualified for a promotion. If the messaging system 126 determines the patient 124 is promotion eligible at step 1640, the method proceeds to step 1642 at which the messaging system 126 performs one or more promotion streams (i.e., methods including sending promotions to the patient 124, etc.). For example, at step 1642, the method 1600 may proceed to other methods (e.g., the method 1100, the method 1200, a method 1700, etc.).

In some embodiments, at step 1634, the method 1600 may proceed to step 1650 in which the messaging system 126 determines if there is a matching Neustar® file for the patient 124. A Neustar® file may be an analytical file that provides statistics on the patient 124, such as the odds or statistical likelihood the patient 124 continues through and completes their treatment plan. In some embodiments, step 1650 may execute prior to, substantially the same time, or after step 1618. If, at step 1650, it is determined, by the messaging system 126, the patient 124 has a Neustar® file, the method 1600 may proceed to step 1652. At step 1652, a personalized notification (which may be substantially the same as the personalized notification from the method 1400) from an office administrator (e.g., a staff member associated with the appointment) is generated and sent to the patient 124. In some embodiments, the personalized notification may be generated by the messaging system 126 and provided to the patient computing device 122. In other embodiments, the personalized notification may be generated by the office administrator, in response to a reminder from the messaging system 126, printed, and provided to the patient 124 by the office administrator (e.g., via the mail).

Figure 17A:
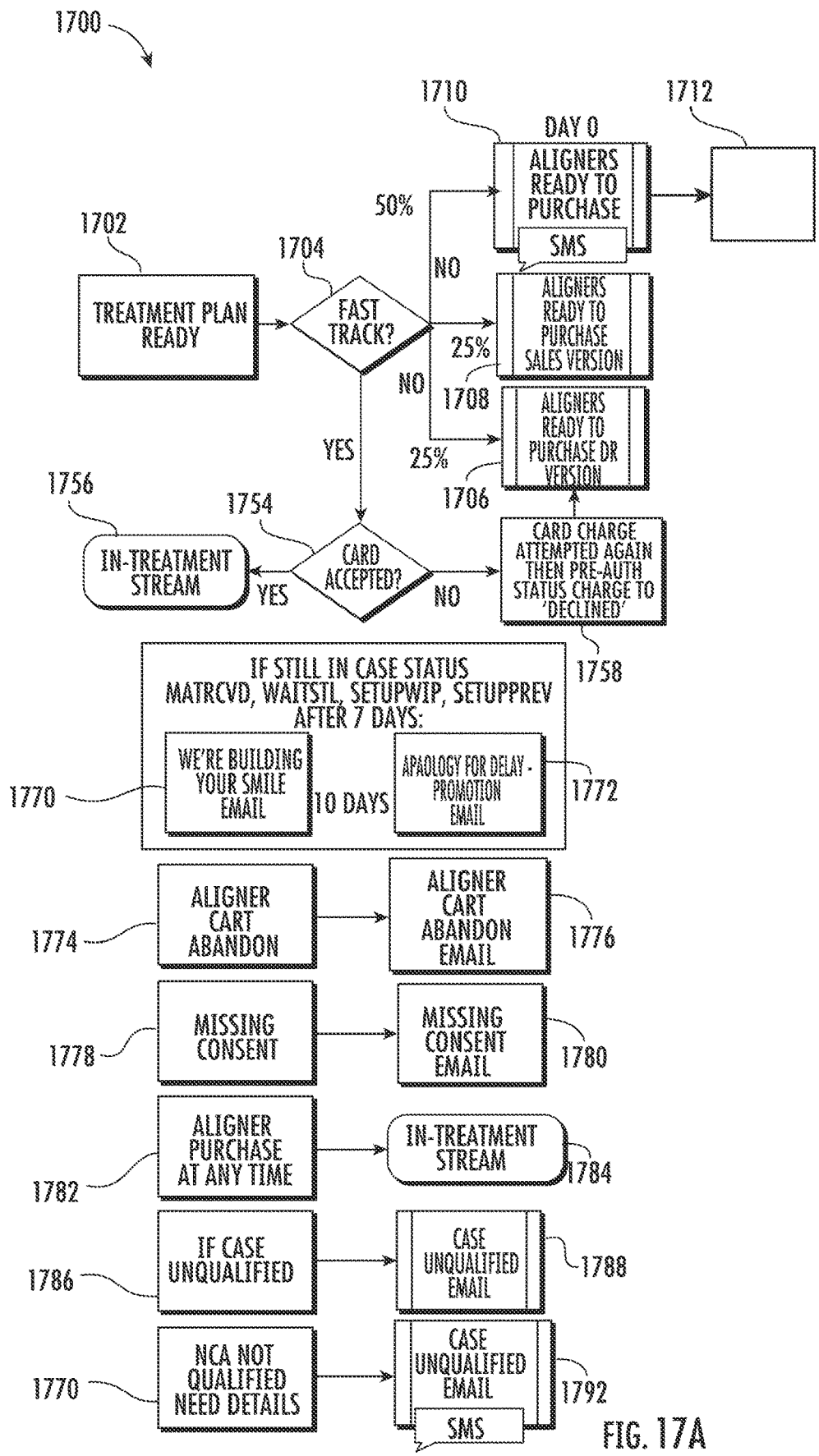
FIGS. 17A-17B are flowcharts showing a method of providing multiple notifications and indications regarding a treatment plan of the patient, according to an illustrative embodiment.
Figure 17B:
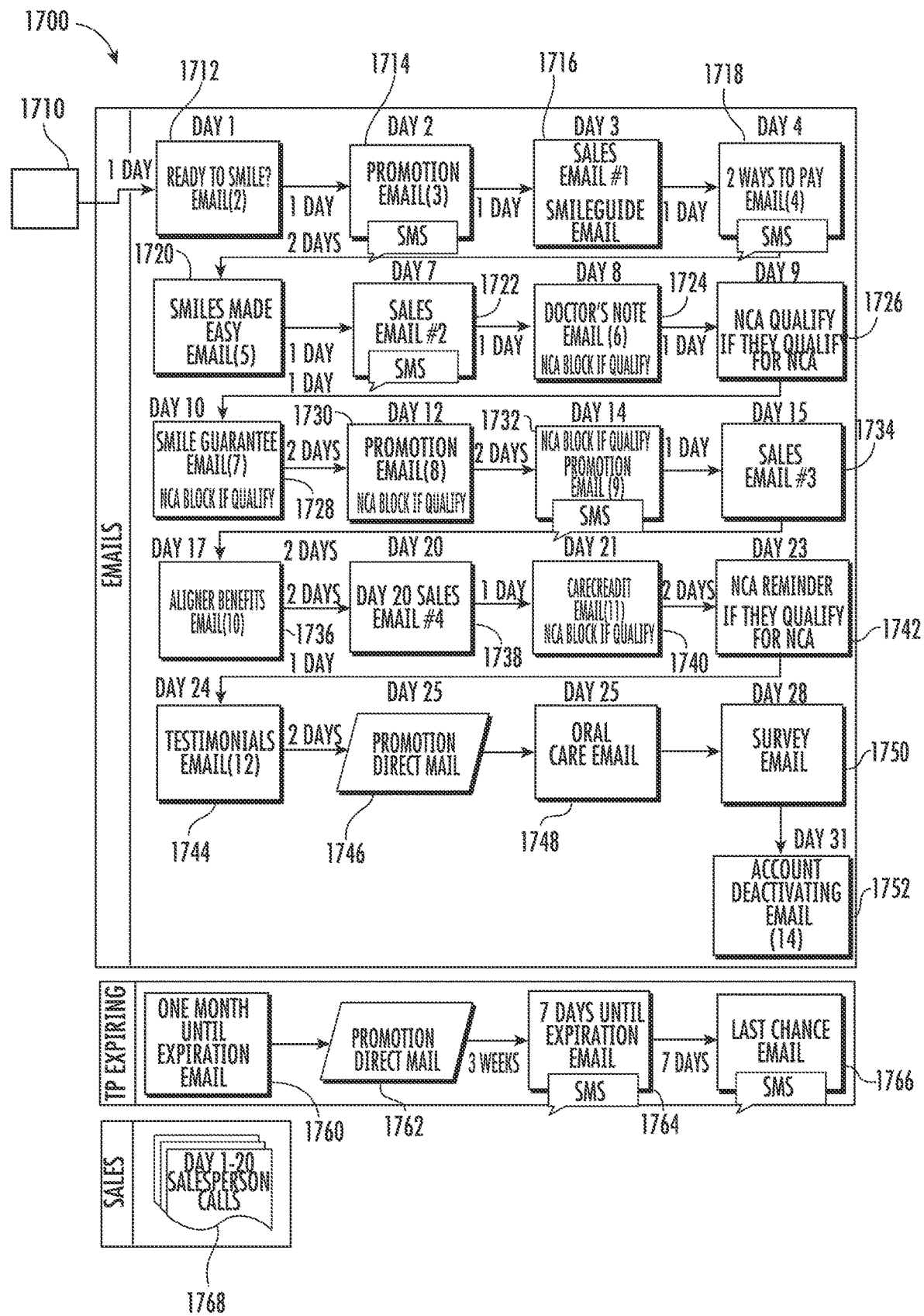

Referring now to FIG. 17A and FIG. 17B, a method 1700 of providing multiple notifications and indications that the treatment plan of the patient 124 is ready to be viewed is shown, according to an example embodiment. The method 1700 commences at step 1702 at which the messaging system 126 determines if the treatment plan of the patient 124 is finished and ready to be viewed by and provided to the patient 124. The management engine 114 may determine that the treatment plan is ready to be viewed responsive to a status update of the patient file (e.g., changing from a first status to a treatment plan ready status). The patient file may be updated by the management engine 114 as described above responsive to the treatment plan computing device 132 uploading, transmitting, or otherwise providing the treatment plan data via the treatment plan portal 134 to the central processing system for incorporation or association with the patient file 115. If the messaging system 126 determines that treatment plan of the patient 124 is finished and ready to be viewed, the method 1700 proceeds to step 1704 at which it is determined if the patient 124 is enrolled in the fast track program. As described above, the "fast track program" refers to patients who have prepaid and/or already signed up to receive aligners following generation of their treatment plan (i.e., signed up for the fast track option described herein). For example, the patient 124 may have paid for treatment or agreed to treatment during the appointment, prior to their treatment plan being ready, or when they created the appointment. In one or more of these examples, the patient is on the fast track program.

If, at step 1704, it is determined, by the messaging system 126, the patient 124 is not on the fast track program, the method 1700 may proceed to one or more of step 1706, 1708, and 1710. In some embodiments, the messaging system 126 may pick randomly between steps 1706, 1708, and 1710 such that the messaging system 126 has a 25% chance of proceeding to step 1706, a 25% chance of proceeding to step 1708, and a 50% chance of proceeding to step 1710. At each of steps 1706, 1708, and 1710, an "Aligners Ready to Purchase" notification may be generated and provided to the patient computing device 122 by the messaging system 126. In some embodiments, each of steps 1706-1710 may relate to a different version of the "Aligners Ready to Purchase" notification (i.e., a differently worded and laid out notification). For example, at step 1706 a Doctor's version of the "Aligners Ready to Purchase" notification may be provided to the patient computing device 122; at step 1708 a Salesperson's version of the "Aligners Ready to Purchase" notification may be provided to the patient computing device 122; and at step 1710 a generic version (i.e., a staff member associated with the dental aligner's version) may be provided to the patient computing device 122. In other embodiments, the version may refer to the occupation of a physical staff member who reaches out to the patient 124 (e.g., via a phone call). Either way, the "Aligners Ready to Purchase" notification may include details about the cost, the treatment, the next steps in the treatment process, etc.

After one or more of steps 1706, 1708, and 1710 have been performed by the messaging system 126 and a day has passed, the method 1700 proceeds to step 1712 of FIG. 17B. At step 1712, a "Ready to Smile" notification may be generated and provided to the patient computing device 122 by the messaging system 126. The "Ready to Smile" notification may include additional details about the treatment plan of the patient 124 as well as provide a link through which the patient 124 can purchase their aligners and treatment plan.

Once the messaging system 126 has provided the "Ready to Smile" notification at step 1712 and a day has passed, the method 1700 proceeds to step 1714 at which the messaging system 126 generates and provides a promotion notification (which may be substantially the same to other promotion notifications described herein) to the patient computing device 122. The promotion notification may offer a promotion to the patient 124 if they proceed with purchasing the treatment plan/aligners.

Once the messaging system 126 has provided the promotion notification at step 1714 and a day has passed, the method 1700 proceeds to step 1716 at which the messaging system 126 generates and provides a sales notification and/or a "SmileGuide" notification to the patient computing device 122. The sales notification may include additional facts about why getting treatment is the best step forward, and the "SmileGuide" notification may include images of treatment or feedback from previous patients who have completed treatment.

Once the messaging system 126 has provided the sales notification and/or the "SmileGuide" notification at step 1716 and a day has passed, the method 1700 proceeds to step 1718 at which the messaging system 126 generates and provides a "2 Ways to Pay" notification to the patient computing device 122. The "2 Ways to Pay" notification may include details about how the patient 124 can pay for the treatment such as through a one-time payment or through a financing option as described above.

Once the messaging system 126 has provided the "2 Ways to Pay" notification at step 1718 and two days have passed, the method 1700 proceeds to step 1720 at which the messaging system 126 generates and provides a "Smiles Made Easy" notification to the patient computing device 122. The "Smiles Made Easy" notification may include details about the average time treatment takes and how the treatment can be completed through receiving aligners in the mail (i.e., no contact).

Once the messaging system 126 has provided the "Smiles Made Easy" notification at step 1720 and a day has passed, the method 1700 proceeds to step 1722 at which the messaging system 126 generates and provides a second sales notification to the patient computing device 122. The second sales notification may be similar to the first sales notification. In some embodiments, the second sales notification may be provided to a different address of the patient computing device 122 than the first sales notification.

Once the messaging system 126 has provided the second sales notification at step 1722 and a day has passed, the method 1700 proceeds to step 1724 at which the messaging system 126 generates and provides "Doctor's Note" notification to the patient computing device 122. The "Doctor's Note" notification may be similar to the other "Doctor's Note" notifications described herein. Furthermore, if the messaging system 126 determines the patient qualifies, the "Doctor's Note" notification may include a region dedicated to nighttime clear aligners (NCA) eligibility. The NCA region may include information relating to and indicating that the patient 124 is qualified for nighttime clear aligners. The NCA region indicates various advantages of NCA in comparison to traditional aligners (similar to the advantages described above with respect to FIG. 6.

Once the messaging system 126 has provided the "Doctor's Note" notification at step 1724, a day has passed, and the messaging system 126 has determined the patient 124 qualifies for NCA, the method 1700 proceeds to step 1726 at which the messaging system 126 generates and provides an "NCA Qualify" notification to the patient computing device 122. The "NCA Qualify" notification may be similar to NCA region discussed with regard to step 1722 but be an entire notification dedicated to information on the NCA as well as including one or more links where the patient 124 can select the NCA option.

Once the messaging system 126 has provided the "NCA Qualify" notification at step 1726 and a day has passed, or the messaging system 126 determined the patient 124 did not qualify for NCA and a day has passed, at step 1724, the method 1700 proceeds to step 1728 at which the messaging system 126 generates and provides a "Smile Guarantee" notification to the patient computing device 122. The "Smile Guarantee" notification may include information about the treatment plan and also discuss a guarantee and/or warranty provided for the patient 124. Additionally, the "Smile Guarantee" notification may include a region dedicated to the NCA, if the patient 124 qualifies for the NCA.

Once the messaging system 126 has provided the "Smile Guarantee" notification to the patient computing device 122 at step 1728 and two days have passed, the method 1700 proceeds to step 1730 at which the messaging system 126 generates and provides a promotion notification to the patient computing device 122, which may be similar to the promotion notification provided to the patient computing device 122 at step 1714. Additionally, the promotion notification may include a region dedicated to the NCA, if the patient 124 qualifies for the NCA.

Once the messaging system 126 has provided the promotion notification to the patient computing device 122 at step 1730 and two days have passed, the method 1700 proceeds to step 1732 at which the messaging system 126 generates and provides a "Final Day" promotion notification to the patient computing device 122. The "Final Day" promotion notification may be similar to the promotion notification provided at step 1714 and also include an indication that this is the final day the promotion is active. If the patient 124 does not access the notification or provide any indication they are interested in the promotion, the messaging system 126 may also deactivate the promotion at the end of the day at step 1732. Additionally, the "Final Day" promotion notification may include a region dedicated to the NCA, if the patient 124 qualifies for the NCA.

Once the messaging system 126 has provided the "Final Day" promotion notification to the patient computing device 122 and a day has passed, the method 1700 proceeds to step 1734 at which the messaging system 126 generates and provides a sales notification to the patient computing device 122. The sales notification may be similar to or the same as the other sales notification discussed herein (e.g., the sales notification provided at step 1722).

Once the messaging system 126 has provided the sales notification to the patient computing device 122 at step 1734 and two days have passed, the method 1700 proceeds to step 1736 at which the messaging system 126 generates and provides an "Aligner Benefits" notification to the patient computing device 122. The "Aligner Benefits" notification may include a comparison between dental aligners and braces or other similar treatments as well as any other benefits provided by dental aligners.

Once the messaging system 126 has provided the "Aligner Benefits" notification to the patient computing device 122 at step 1736 and two days have passed, the method 1700 proceeds to step 1738 at which the messaging system 126 generates and provides a sales notification to the patient computing device 122, which may be similar to the other sales notifications described herein (e.g., the sales notification described with respect to step 1716).

Once the messaging system 126 has provided the sales notification to the patient computing device 122 at step 1738 and a day has passed, the method 1700 proceeds to step 1740 at which the messaging system 126 generates and provides a "CareCredit" notification to the patient computing device 122. The "CareCredit" notification may include information about the CareCredit program which may be a type of financing available to the patient 124 as well as a link that navigates the patient 124 to a CareCredit application. Additionally, the "CareCredit" notification may include a region dedicated to the NCA, if the patient 124 qualifies for the NCA.

Once the messaging system 126 has provided the "CareCredit" notification to the patient computing device 122 at step 1740 and two days have passed, the method 1700 proceeds to step 1742 at which the messaging system 126 generates and provides an "NCA Reminder" notification to the patient computing device 122, if the patient 124 qualifies for the NCA. The "NCA Reminder" notification may be similar to the "NCA Qualify" notification provided to the patient computing device at step 1726, but further include details about the NCA and serve as a reminder to the patient 124 that the NCA is available to the patient 124.

If, at step 1740 it is determined the patient 124 is not qualified for the NCA and two days have passed, or if, at step 1742 the "NCA Reminder" notification has been provided to the patient computing device 122 and a day has passed, the method 1700 proceeds to step 1744 at which the messaging system 126 generates and provides a "Testimonials" notification to the patient computing device 122. The "Testimonials" notification may include regions with testimonials from previous patients who have successfully completed the treatment.

Once the messaging system 126 has provided the "Testimonials" notification to the patient computing device 122 at step 1744 and two days have passed, the method 1700 proceeds to step 1746 at which the messaging system 126 generates and provides a promotion notification to the patient computing device 122. The promotion notification may be similar to the other promotion notifications described herein, or may be sent via direct mail to the patient 124 (as compared to the patient computing device 122). By sending the promotion notification via direct mail, it may better reach the patient 124 and more likely cause the patient to purchase dental aligners.

Once the messaging system 126 has provided the promotion notification to the patient computing device 122 at step 1746 or the promotion notification has been sent out via direct mail, the method 1700 proceeds to step 1748 at which the messaging system 126 generates and provides a "Oral Care" notification to the patient computing device 122. The "Oral Care" notification may include information about how to take care of a person's mouth and gums (e.g., "Brush Daily") as well as links to one or more products that assist with oral care.

Once the messaging system 126 has provided the "Oral Care" notification to the patient computing device 122 at step 1748 and/or three days have passed, the method 1700 proceeds to step 1750 at which the messaging system 126 generates and provides a survey notification to the patient computing device 122. The survey notification may be similar to the survey notification discussed with respect to the method 1600 but further include survey questions or a link to a survey with questions and feedback on why the patient 124 did not purchase dental aligners.

Once the messaging system 126 has provided the survey notification to the patient computing device 122 at step 1750 and/or three days have passed or the messaging system 126 determines it has been 31 days since the treatment plan was ready/finished, the method 1700 proceeds to step 1752 at which the messaging system 126 generates and provides an "Account Deactivating" notification to the patient computing device 122. The "Account Deactivating" notification may inform the patient 124 that their account has been deactivated or will be deactivated within a specific number of days. In some embodiments, once the "Account Deactivating" notification has been provided to the patient computing device 122, the messaging system 126 deactivates the account of the patient 124 (which may cause the management engine 114 to delete the patient file 115 for the patient, update the status of the patient file 115 to a "deactivated" or "inactive" status, an aligner not purchased status, etc.). In other embodiments, the account of the patient 124 is deactivated after the specific number of days in which no response is received.

Returning back to step 1704 of FIG. 17A, if it is determined that the patient 124 is enrolled in the fast track program, the method 1704 proceeds to step 1754 at which it is determined, by the messaging system 126, if the payment information previously provided by the patient 124 has been accepted. If the payment information is accepted at step 1754, the method proceeds to step 1756 at which the patient 124 is considered to be "In-Treatment" and the messaging system 126 proceeds to methods associated with providing notifications relating to being "In-Treatment" (e.g., the method 1900 discussed herein). If the payment information is not accepted at step 1754, the method proceeds to step 1758 at which the payment information is tried again and then is considered to be "Declined" or not active by the messaging system 126. After the payment information is considered to be "Declined," at step 1758, the method 1700 proceeds to step 1706.

Returning to FIG. 17B, if at any step of the method 1700 it is determined that the treatment plan is expiring within a month, the method 1700 proceeds to step 1760 at which the messaging system 126 determines that the treatment plan of the patient is expiring within a month and then generates and provides a "One Month Until Expiration" notification to the patient computing device 122. The "One Month Until Expiration" notification may inform the patient 124 their treatment plan is expiring in a month and include details on how the patient 124 may move forward with their treatment plan. In some embodiments, the One Month Until Expiration" notification may further include a link which navigates the patient 124 to purchase dental aligners for their treatment plan.

Once the messaging system 126 has provided the "One Month Until Expiration" notification to the patient computing device 122 at step 1760, the method 1700 proceeds to step 1762 at which the messaging system 126 generates and provides a promotion notification to the patient computing device 122. The promotion notification may be similar to the other promotion notifications described herein, or may be sent via mail to the patient 124 (as compared to the patient computing device 122). By sending the promotion notification via mail, it may better reach the patient 124.

Once the messaging system 126 has provided the promotion notification to the patient computing device 122 at step 1762 and three weeks have passed, or the promotion notification has been sent out via mail and three weeks have passed the method 1700 proceeds to step 1764 at which the messaging system 126 generates and provides a "7 Days Until Expiration" notification to the patient computing device 122. The "7 Days Until Expiration" notification may inform the patient 124 their treatment plan is expiring in a seven days and include details on how the patient 124 may move forward with their treatment plan. In some embodiments, the "7 Days Until Expiration" notification may further include a link which navigates the patient 124 to purchase dental aligners for their treatment plan. In some embodiments, the "7 Days Until Expiration" notification may be sent to the patient computing device 122 using a different address than was used for the "One Month Until Expiration" notification."

Once the messaging system 126 has provided the "7 Days Until Expiration" to the patient computing device 122 at step 1764 and seven days have passed, the method 1700 proceeds to step 1766 at which the messaging system 126 generates and provides a "Last Chance" notification to the patient computing device 122. The "Last Chance" notification may inform the patient 124 their treatment plan will expire if they do not purchase dental aligners and include information on how the patient 124 may move forward with their treatment plan. In some embodiments, the if patient 124 does not purchase the treatment plan by the end of the day or respond by the end of the day, the messaging system 126 changes the status of the treatment plan to expired, following step 1766.

If at any step of the method 1700 it is determined that patient 124 is more responsive to phone calls or the patient 124 has requested a phone call, the method 1700 may proceed to step 1768 at which a salesperson associated with the treatment plan calls the patient 124 at their phone number.

Returning again to FIG. 17A, if at any step of the method 1700 it is determined that the treatment plan is taking longer than seven days to generate, finalize, or for the aligners themselves to be manufactured, the method 1700 proceeds to step 1770 at which the messaging system 126 generates and provides a "We're Building Your Smile" notification to the patient computing device 122. The "We're Building Your Smile" notification may inform the patient 124 their treatment plan is taking longer than expected, may include information on why their treatment plan is taking longer than expected, and/or may provide the patient 124 with a phone number to call with any questions, as well as include information on how the treatment plan is created.

Once the messaging system 126 has provided the "We're Building Your Smile" notification to the patient computing device 122 at step 1770, seven days have passed, and the treatment plan of the patient 124 is not finalized, the method 1700 proceeds to step 1770 at which the messaging system 126 generates and provides a "Apology for the Delay" notification to the patient computing device 122. The "Apology for the Delay" notification may inform the patient 124 their treatment plan is taking longer than expected and include one or more promotions, such as a coupon code or gift card for free retainers.

If at any step of the method 1700 the patient 124 navigates to one or more webpages, generates a "cart" which includes the aligners, or otherwise shows intent to purchase the aligners (e.g., by clicking the one or more links within the sales notifications, the promotion notifications, etc.), but does not complete the purchase, the method 1700 proceeds to step 1774. At step 1774, the messaging system 126 determines if the cart of the patient 124 included the aligners and if the patient proceeded to abandon their cart (i.e., the patient did not complete their transaction and purchase the aligners). If the patient 124 did indeed abandon their cart, the method 1700 proceeds to step 1776 at which the messaging system 126 generates and provides a "Aligner Abandon Cart" notification to the patient computing device 122. The "Aligner Abandon Cart" notification may include details about the cart the patient 124 abandoned, such as the date and time the patient 124 attempted to or showed an interest in purchasing dental aligners and include a link to the cart for completing their purchase.

If at any step of the method 1700 the messaging system 126 determines that the patient has not provided a consent form or otherwise indicate their consent to treatment via dental aligners, the method 1700 proceeds to step 1776. At step, 1776, the messaging system 126 confirms that the patient 124 requires a consent form and has not yet provided one or that there is no consent form within the patient file. If, the messaging system 126 confirms the patient 124 requires a consent form and has not yet provided one, the method 1700 proceeds to step 1780 at which the messaging system 126 generates and provides a "Missing Consent" notification to the patient computing device 122. The "Missing Consent" notification may include details about the missing consent form as well as information about why a consent form is required and who is able to sign the consent form. In some embodiments, the "Missing Consent" notification may further include a link to a signable consent form or include the consent form as an attachment and request the consent form be returned with a signature.

If at any step of the method 1700 the messaging system 126 determines that the patient has purchase dental aligners, the method 1700 proceeds to step 1782. At step, 1782, the messaging system 126 confirms that the patient 124 has purchased dental aligners. If the messaging system 126 confirms the patient 124 has purchased dental aligners, the method 1700 proceeds to step 1784 at which the patient 124 is considered to be "In-Treatment" and the messaging system 126 proceeds to methods associated with providing notifications relating to being "In-Treatment" (e.g., the method 1900 discussed herein).

If at any step of the method 1700 the messaging system 126 determines or receives an indication that the patient 124 is not qualified for treatment, the method 1700 proceeds to step 1786. As noted above, the patient 124 may be determined to be fit for treatment by an approving dentist or orthodontist following patient intake and prior to generation of the treatment plan. The approving dentist or orthodontist may approve the patient as being fit for treatment based on the 3D model of the patient's teeth and dental history information/patient intake data. The management engine 114 may receive a command from the approving dental computing device 138 which indicates whether the patient is fit for treatment (e.g., qualified for treatment). At step 1786, the messaging system 126 confirms that the patient 124 is not qualified for treatment. If, the messaging system 126 confirms the patient 124 is not qualified for treatment, the method 1700 proceeds to step 1788 at which the messaging system 126 generates and provides a "Case Unqualified" notification to the patient computing device 122. The "Case Unqualified" notification may include details about why the patient 124 is not qualified for receiving treatment and provide the patient 124 with other possible treatments that may be performed or a referral to a dentist or orthodontist (as described below with reference to FIG. 22.

If at any step of the method 1700 the messaging system 126 determines or receives an indication that the patient 124 is not qualified for the NCA, the method 1700 proceeds to step 1790. At step, 1790 the messaging system 126 confirms that the patient 124 is not qualified for the NCA. If, the messaging system 126 confirms the patient 124 is not qualified for the NCA, the method 1700 proceeds to step 1792 at which the messaging system 126 generates and provides a "NCA Case Unqualified" notification to the patient computing device 122. The "NCA Case Unqualified" notification may include details about why the patient 124 is not qualified for receiving the NCA and provide the patient 124 with other possible remedial actions.

Lastly, while not shown, after approximately 6 months from the appointment of the patient in which the patient 124 has not purchased the dental aligners, the method 1700 may proceed to a step in which the messaging system 126 generates and provides a hygiene reminder notification to the patient computing device 122. The hygiene reminder notification may include information about a possible cleaning or dentist appointment and may be for the dentist office at which the patient 124 received their intraoral scan or received impressions. In one example, the hygiene reminder may include a date, a time, and the location of the dentist office in which a teeth cleaning is to take place and also include a link through which the patient 124 can provide confirmation, that is received by the messaging system 126, they will attend the cleaning. The dental office may be the same dental office 118 which performed patient intake, and the patient may be reminded during the appointment to conduct another intraoral scan or submit another set of impressions for generating a treatment plan (e.g., following expiration of the patient's prior treatment plan).

Figure 18:
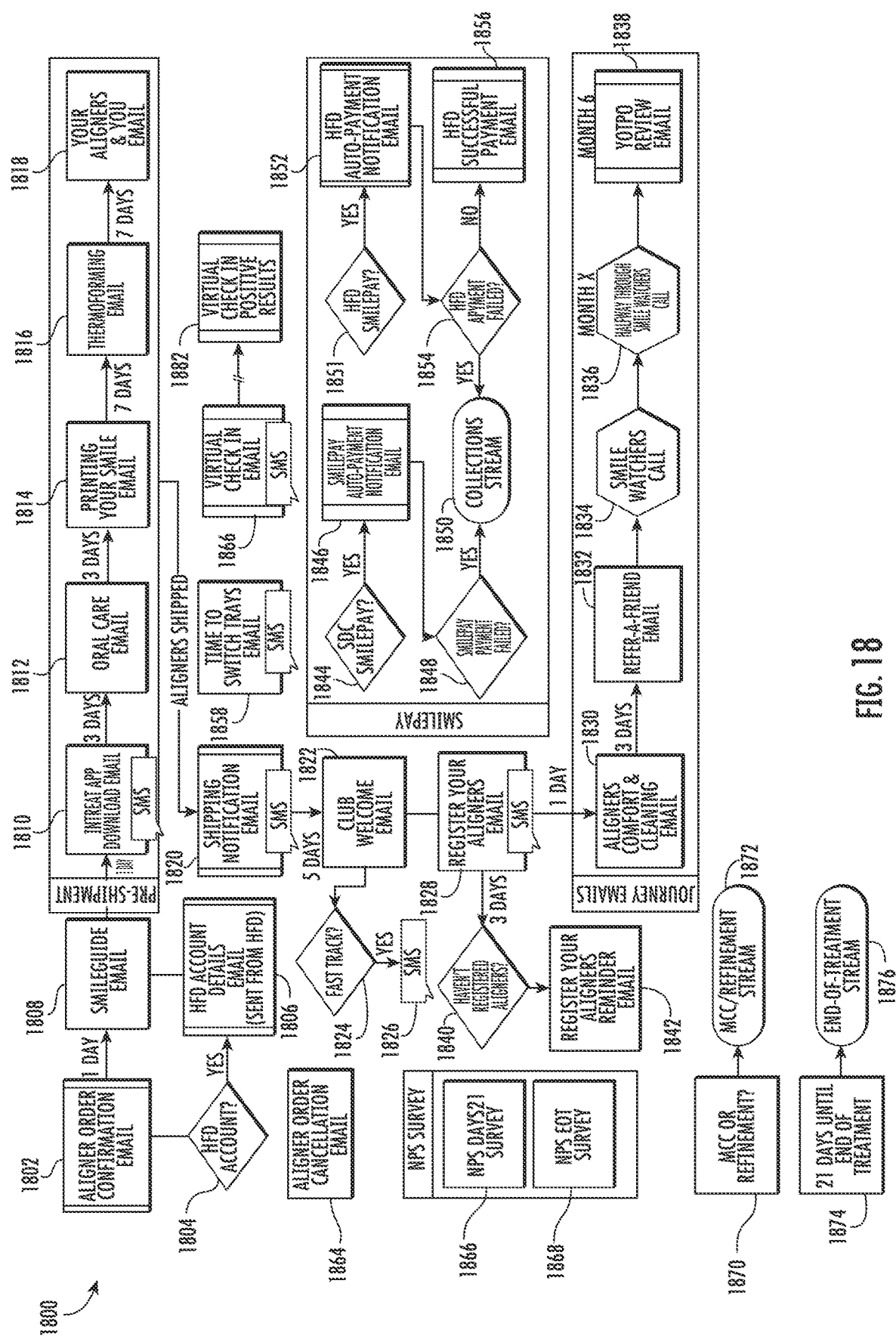
FIG. 18 is a flowchart showing a method of providing one or more notifications to the patient during treatment, according to an illustrative embodiment.

Referring now to FIG. 18, a method 1800 of providing one or more notifications to the patient 124 during their treatment using the dental aligners is shown according to an example embodiment. Method 1800 commences at step 1802 in which the messaging system 126 determines the patient has ordered dental aligners and generates and provides an aligner order confirmation notification to the patient computing device 122. The aligner order confirmation notification may include order details such as the total cost of the dental aligners, the length of time the dental aligners will need to worn, the number of dental aligners the patient 124 will receive, an order number, the payment information used to process the payment, and any other details relating to the dental aligner order.

If the patient 124 has a Healthcare Finance Direct (HFD) account or receives an indication that the patient 124 has an HFD account, the method 1800 proceeds to step 1804 at which the messaging system 126 confirms (e.g., checks the patient file of) the patient 124 having an HFD account. If at step 1804 the messaging system 126 confirms the patient 124 has an HFD account, the method 1800 proceeds to step 1806 at which the messaging system 126 generates and provides a "HFD Account Details" notification to the patient computing device 122. In some embodiments, the "HFD Account Details" notification is generated and provided to the patient computing device 122 by an HFD computing device or system. The "HFD Account Details" notification may include details about the HFD account of the patient 124 such as an account number, a username, and a temporary password. In some embodiments, the "HFD Account Details" notification further includes a link to the HFD account of the patient 124 (e.g., a link that navigates the patient 124 to a login page of the HFD account).

After the "HFD Account Details" notification has been provided to the patient computing device at step 1806, or after a day has passed at step 1802, the method 1800 proceeds to step 1808 at which a "SmileGuide" notification is generated and provided to the patient computing device 122 by the messaging system 126. The "SmileGuide" notification may include details about the aligner treatment, how to apply or insert and wear each aligner, proper sanitation for the aligner, and/or contact information if the dental aligners are not working correctly.

Once the messaging system 126 has provided the "SmileGuide" notification to the patient computing device 122 at step 1808 and a day has passed, the method 1800 proceeds to step 1810 at which the messaging system 126 generates and provides a "INTREAT Application Download" notification to the patient computing device 122. The "INTREAT Application Download" notification may include information about the INTREAT Application, which is an application that guides the patient 124 through treatment and may include various user interfaces for the patient to upload progress photographs and other feedback information. The "INTREAT Application Download" notification may include a link to download the INTREAT application (e.g., a link to the INTREAT application in an app store, a software download of the INTREAT application, etc.).

Once the messaging system 126 has provided the "INTREAT Application Download" notification to the patient computing device 122 at step 1810 and three days have passed, the method 1800 proceeds to step 1812 at which the messaging system 126 generates and provides an "Oral Care" notification to the patient computing device 122. The "Oral Care" notification may be substantially the same as the "Oral Care" notification of the method 1700 but further include dental aligner-specific oral care information.

Once the messaging system 126 has provided the "Oral Care" notification to the patient computing device 122 at step 1812 and three days have passed, the method 1800 proceeds to step 1814 at which the messaging system 126 generates and provides a "Printing Your Smile" notification to the patient computing device 122. The "Printing Your Smile" notification may include information that physical models corresponding to the treatment plan are being fabricated and/or on how the physical models are fabricated, such as information on various additive fabrication processes.

Once the messaging system 126 has provided the "Printing Your Smile" notification to the patient computing device 122 at step 1814 and seven days have passed, the method 1800 proceeds to step 1816 at which the messaging system 126 generates and provides a thermoforming notification to the patient computing device 122. The thermoforming notification may include information on how the dental aligners are fabricated from the physical models, such as information on the thermoforming fabrication process.

Once the messaging system 126 has provided the thermoforming notification to the patient computing device 122 at step 1816 and seven days have passed, the method 1800 proceeds to step 1818 at which the messaging system 126 generates and provides a "Your Aligners and You" notification to the patient computing device 122. The "Your Aligners and You" notification may include information on how the aligners and the treatment plan are custom built to create an improved smile for the patient 124 as well as details on the treatment process.

If at any of the steps 1810, 1812, 1814, 1816, or 1818, the messaging system 126 determines or receives an indication that the dental aligner(s) of the patient 124 have shipped, the method 1800 proceeds to step 1820 at which a the messaging system 126 generates and provides a shipping notification to the patient computing device 122. The shipping notification may include regions dedicated to the shipping information (i.e., estimated arrival date, shipping address, company doing the shipping, etc.) and a link to a dedicated shipping tracking code.

Once the messaging system 126 has provided the shipping notification to the patient computing device 122 at step 1820 and five days have passed (i.e., it is assumed the patient 124 has received their aligners), the method 1800 proceeds to step 1822 at which the messaging system 126 generates and provides a "Club Welcome" notification to the patient computing device 122. The "Club Welcome" notification may include information on the treatment process moving forward as well as welcome the patient 124 to the club of an improved smile. In some embodiments, the "Club Welcome" notification further includes a username and temporary password for the INTREAT application of the patient 124.

Once the messaging system 126 has provided the "Club Welcome" notification to the patient computing device 122 at step 1824, the method 1800 proceeds to step 1824 at which the messaging system 126 determines or receives an indication that the patient 124 a enrolled in the fast track program or is not enrolled in the fast track program. If at step 1824, the messaging system 126 determines the patient 124 is enrolled in the fast track program, the method 1800 proceeds to step 1826 at which the messaging system 126 generates and provides a fast track notification to the patient computing device 122. The fast track notification may include detail about the fast track program and what the fast track program will provide the patient 124 throughout treatment.

Additionally, once the messaging system 126 has provided the "Club Welcome" notification to the patient computing device 122 at step 1824, the method 1800 proceeds to step 1828 at which the messaging system 126 generates and provides a "Register your Aligners" notification to the patient computing device 122. The "Register your Aligners" notification may include detail on why the patient 124 should register their aligners, how the patient 124 can register their aligners, and the benefits of registering the dental aligners (e.g., in the INTREAT application). In some embodiments, the "Register your Aligners" notification further includes a link to a website or the INTREAT application through which the patient 124 can register their dental aligners.

Once the messaging system 126 has provided the "Register your Aligners" notification to the patient computing device 122 at step 1828 and a day has passed, the method 1800 proceeds to step 1830 at which the messaging system 126 generates and provides a "Aligners Comfort and Cleaning" notification to the patient computing device 122. The "Aligners Comfort and Cleaning" notification may include detail on how the patient 124 can clean their aligners, products that are available to aid in cleaning the dental aligner, and one or more tips on how the patient 124 can keep their dental aligners comfortable. In some embodiments, the "Aligners Comfort and Cleaning" notification may include one or more links to comfort or aligner cleaning products.

Once the messaging system 126 has provided the "Aligners Comfort and Cleaning" notification to the patient computing device 122 at step 1830 and three days have passed, the method 1800 proceeds to step 1832 at which the messaging system 126 generates and provides a "Refer-a-Friend" notification to the patient computing device 122. The "Refer-a-Friend" notification may include detail on how the patient 124 can clean refer their friends to receive treatment and include directions to receive a promotion if the patient 124 does refer a friend. In some embodiments, the "Refer-a-Friend" notification further includes a referral code that is specific to the patient 124 that is during purchase of the dental aligners or during scheduling of the appointment to indicate the patient 124 provided the referral.

Once the messaging system 126 has provided the "Refer-a-Friend" notification to the patient computing device 122 at step 1832, the method 1800 proceeds to step 1834 at which the messaging system 126 generates and provides a "Smile Watcher" notification to the patient computing device 122. The "Smile Watchers" notification may include information on a Smile Watchers program through which patients 124 (and others) can receive information and progress updates on the other patients undergoing treatment via dental aligners. In some embodiments, the "Smile Watcher" notification is provided to the patient 124 or the patient computing device 122 through a phone call by a staff member associated with the Smile Watchers promotion.

Once the messaging system 126 has provided the Smile Watcher notification to the patient computing device 122 at step 1834, the method 1800 proceeds to step 1836 at which the messaging system 126 generates and provides a "Half Way through Smile Watchers" notification to the patient computing device 122. The "Half Way through Smile Watchers" notification may congratulate the patient 124 on getting halfway through treatment and again include information on the Smile Watchers program. In some embodiments, the "Half Way through Smile Watcher" notification is provided to the patient 124 or the patient computing device 122 through a phone call by a staff member associated with the Smile Watchers promotion.

Once the messaging system 126 has provided the "Half Way through Smile Watchers" notification to the patient computing device 122 at step 1836, the method 1800 proceeds to step 1838 at which the messaging system 126 generates and provides a review notification to the patient computing device 122. The review notification may include information on a possible review that the patient 124 can perform as well as a link to the review website or page that the patient 124 can provide. In one example, the review notification is related to a YOTPO review that the messaging system 126 is request the patient 124 fill out. In some embodiments, the messaging system 126 receives an indication if the patient 124 provides a review in response to the review notification.

Going back to step 1828, once the messaging system 126 has provided the "Register your Aligners" notification to the patient computing device 122 at step 1828 and three days have passed, the method 1800 proceeds to step 1840 at which the messaging system 126 determines if the patient 124 has registered their aligners (e.g., by checking the patient file). If the patient 124 has not registered their dental aligners, the method 1800 proceeds to step 1842 at which the messaging system generates and provides a "Register your Aligners" follow up notification to the patient computing device 122. The "Register your Aligners" follow up notification may again remind the patient 124 to register their dental aligners and serve as a reminder to the patient 124. In some embodiments, the "Register your Aligners" follow up notification and the "Register your Aligners" notification are provided to the patient computing device 122 using two different addresses (e.g., email and phone number, etc.).

If during any point of the method 1800 or other methods described herein, the messaging system 126 receives an indication or determines that the patient is enrolled in SmilePay, the method 1800 proceeds to step 1844. At step 1844, messaging system 126 confirms that the patient 124 is enrolled in SmilePay. If the messaging system 126 confirms that the patient is enrolled in SmilePay at step 1844, the method 1800 proceeds to step 1846 at which the messaging system 126 generates and provides a "SmilePay Auto-Payment" notification to the patient computing device 122. The "SmilePay Auto-Payment" notification may request that the patient 124 sets up automatic payment or provide details about an automatic payment that is coming up (e.g., payment date, payment amount, payment information being used to process the payment, etc.) as well as include a link to the SmilePay website.

Once the messaging system 126 has provided the "SmilePay Auto-Payment" notification to the patient computing device 122 at step 1846, the method 1800 proceeds to step 1848 at which the messaging system 126 determines if the automatic payment was successful or failed. If the automatic payment failed, the method 1800 proceeds to step 1850 at which the messaging system 126 proceeds to generate and provide the patient computing device 122 collections notifications, which may be similar to other notifications as described herein.

If during any point of the method 1800 or other methods described herein, the messaging system 126 receives an indication or determines that the patient is enrolled in HFD SmilePay, the method 1800 proceeds to step 1851. At step 1851, the messaging system 126 confirms that the patient 124 is enrolled in the HFD SmilePay. If the messaging system 126 confirms that the patient is enrolled in the HFD SmilePay at step 1851, the method 1800 proceeds to step 1852 at which the messaging system 126 generates and provides a "HFD Auto-Payment" notification to the patient computing device 122. The "HFD Auto-Payment" notification may request that the patient 124 sets up automatic payment or provide details about an automatic payment that is coming up (e.g., payment date, payment amount, payment information being used to process the payment, etc.) as well as include a link to the HFD SmilePay web site.

Once the messaging system 126 has provided the "HFD Auto-Payment" notification to the patient computing device 122 at step 1852, the method 1800 proceeds to step 1854 at which the messaging system 126 determines if the automatic payment relating to the HFD was successful or failed. If the automatic payment failed, the method 1800 proceeds to step 1850 at which the messaging system 126 proceeds to generate and provide the patient computing device 122 collections notifications as described herein. If the automatic payment was successful, the method 1800 proceeds to step 1856 at which the messaging system 126 generates and provides a "HFD Successful Payment" notification to the patient computing device 122. The "HFD Successful Payment" notification may include information about the successful payment (e.g., date, time, amount, payment information used, etc.).

If during any point of the method 1800 or other methods described herein, the messaging system 126 receives an indication or determines that treatment plan calls for the patient 124 to switch to a new aligner tray (i.e., a new dental aligner out of the set of dental aligners sent to the patient), the method 1800 proceeds to step 1858. At step 1858, the messaging system 126 generates and provides a "Time to Switch Trays" notification to the patient computing device 122. The "Time to Switch Trays" notification may act as reminder to the patient 124 to switch aligner trays and include information about which aligner tray the patient 124 is to switch to, what to do if the new aligner tray does not fit, and include a contact number or link the patient 124 can use if the aligner tray does not fit.

If during any point of the method 1800 or other methods described herein, the messaging system 126 receives an indication or determines it is time for a virtual check-in (e.g., the patient 124 just switched aligner trays, the patient 124 requested a virtual check-in, the patient 124 has not been responding to notifications, etc.), the method 1800 proceeds to step 1860. At step 1860, the messaging system 126 generates and provides a "Virtual Check In" notification to the patient computing device 122. The "Virtual Check In" notification may request feedback on how treatment is going for the patient 124, the experience of the patient 124 so far, and any other details that are required to determine if the treatment is working as expected.

If at step 1860 the patient 124 provides positive results (which may be determined by the messaging system 126 based on key words within the response of the patient 124, by the selection of specific feedback from the "Virtual Check In" notification, or by a command received from a computing device of a dentist or orthodontist which attends the virtual check-in appointment and confirms the patient is "on-track" for their treatment plan), the method 1800 proceeds to step 1862. At step 1862, the messaging system 126 generates and provides a "Virtual Results—Positive" notification to the patient computing device 122. The "Virtual Results—Positive" notification may request the permission of the patient 124 to share their positive results with others.

If during any point of the method 1800 or other methods described herein, the messaging system 126 receives an indication or determines the patient 124 has cancelled their dental aligner order, the method 1800 proceeds to step 1864. At step 1864, the messaging system 126 generates and provides a "Aligner Order Cancellation" notification to the patient computing device 122. The "Aligner Order Cancellation" notification may request feedback on why the patient 124 cancelled their dental aligner as well as include information about the cancelled order.

If during any point of the method 1800 or other methods described herein, the messaging system 126 receives determines that patient 124 has been receiving treatment for 21 or more days, the method 1800 proceeds to step 1866. At step 1866, the messaging system 126 generates and provides a 21 day survey notification to the patient computing device 122. The 21 day survey notification may request feedback on how treatment has been for the first 21 days, how treatment can be improved, and if the patient 124 plans to continue treatment. In some embodiments, the 21 day survey notification includes a link to the survey as compared to including the survey.

If during any point of the method 1800 or other methods described herein, the messaging system 126 receives determines that patient 124 has finished treatment or is about to finish treatment (e.g., one or more days away from finishing), the method 1800 proceeds to step 1868. At step 1868, the messaging system 126 generates and provides an end of treatment survey notification to the patient computing device 122. The end of treatment survey notification may request feedback on how treatment worked for the patient 124, how treatment can be improved, and if the patient 124 is happy or content with their teeth. In some embodiments, the end of treatment survey notification includes a link to the survey as compared to including the survey.

If during any point of the method 1800 or other methods described herein, the messaging system 126 determines that the patient needs or has requested a mid-course correction (MCC), the method 1800 proceeds to step 1870. A MCC indicates that the patient's teeth are not moving properly according to the treatment plan (e.g., because the current aligners of the patient are not fitting or are not correcting the teeth of the patient 124 correctly). Furthermore, during an MCC, the patient 124 goes through the entire process again (i.e., schedules and receives an intraoral scan or impressions, receives a new treatment plan, receives new aligners based on the new treatment plan, etc.) At step 1870, the messaging system 126 confirms that the patient 124 requires or has requested an MCC. If the patient requires or has requested an MCC, the method 1800 proceeds to step 1872. At step 1872, the messaging system 126 may take one or more actions and provide one or more notifications to the patient 124 in regard to the MCC. For example, the messaging system 126 may provide the patient computing device 122 an appointment request for a new intraoral scan or new set of impressions. In one embodiment, the messaging system 126 may first attempt to (e.g., send a notification requesting to) to schedule an intraoral scan at an intraoral scanning site 120. If the patient 124 indicates they cannot attend an appointment at the intraoral scanning site 120 or the intraoral scanning site 120 is too far from the address of the patient 124, the messaging system 126 may attempt to send the patient 124 a dental impression kit. If the patient 124 indicates they do not want a dental impression kit, cannot receive a dental impression kit, or does not return the dental impression kit, the messaging system 126 may, last of all, attempt to (e.g., send a notification requesting to) schedule an intraoral scan at the dental office 118 (e.g., where the patient received their first intraoral scan) described herein. In this order of importance (intraoral scan appointment at SmileShop, dental impression kit, then, last, intraoral scan at the dental office 118), the messaging system 126 may attempt to provide notifications to the patient computing device 122 in regard to a new intraoral scan (or other 3D representation) for purposes of the MCC.

If during any point of the method 1800 or other methods described herein, the messaging system 126 receives determines that patient 124 is 21 days or less from the end of treatment, the method 1800 proceeds to step 1874. At step 1874, the messaging system 126 confirms that the patient 124 is 21 days or less from the end of treatment. If the messaging system 126 confirms that the patient 124 is 21 day or less from the end of the treatment, the method 1800 proceeds to step 1876 at which the messaging system generates and provides one or more notifications relating to the end of treatment. For example, at step 1876, the messaging system 126 may implement a new method (e.g., the method 1900, a method 2000, etc.) that are related to the end of treatment.

Figure 19:
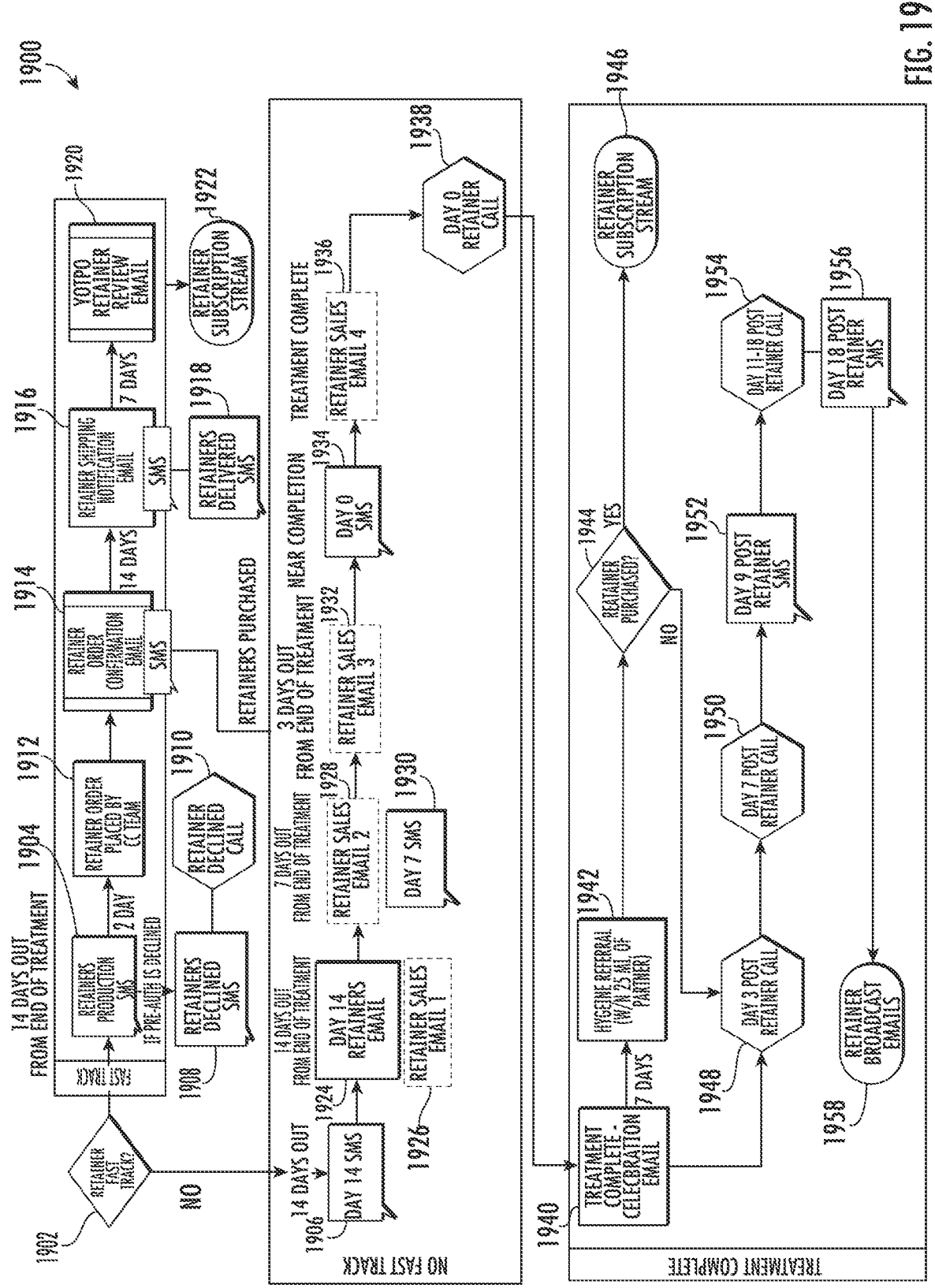
FIG. 19 is a flowchart showing a method of providing notifications regarding retainers for a patient undergoing treatment, according to an illustrative embodiment.

Referring now to FIG. 19, a method 1900 of providing multiple notifications and indications regarding retainers for a patient undergoing treatment via dental aligners, according to an example embodiment. It is noted that, following a patient receiving treatment via dental aligners as described herein, the patient may be instructed to wear a retainer. The retainer may function in a manner similar to the dental aligners to maintain (rather than move) a position of the patient's teeth. For example, the patient may wear a retainer nightly following treatment to maintain a position of the patient's teeth following treatment. Similar to receiving treatment via dental aligners, the patient may be fitted for a retainer by receiving a follow-up intraoral scan or impression at a dental office 118 (or intraoral scanning site 120), which may be the same dental office 118 or intraoral scanning site 120 in which the patient originally visited for obtaining the dental aligners, or may be a different dental office 118 or intraoral scanning site 120. Additionally or in the alternative, the 3D data corresponding to the patient's final position may be transmitted to the central processing system 102 and included in the patient file (e.g., by the management engine 114 which maintains the patient file as described above) for use in creating a retainer. The patient may approve production of a retainer (e.g., by purchasing the retainer), and the fabrication system 144 may fabricate the retainer for the patient in a manner similar to fabricating dental aligners 146 as described above. The shipment processing system 154 may ship the retainer to the patient in a manner similar to shipping the aligners to the patient as described above.

As described in greater detail below, the messaging system 126 may transmit various notifications and initiate various phone calls at or around completion of the patient's treatment plan. The management engine 114 may be configured to determine a date upon which the patient is targeted to complete treatment via dental aligners. Such data may be maintained by the management engine 114 in the patient file for the patient. For example, when the patient initiates treatment on January 1$^{st}$, and the treatment plan includes 18 dental aligners which are to be worn in sequence for two weeks each, the management engine 114 may be configured to compute or otherwise determine a treatment plan completion date as 36 weeks from the start of treatment, or September 10$^{th}$ (which is 36 weeks from January 1$^{st}$). The management engine 114 may be configured to update the patient file to include the treatment plan completion date. In some embodiments, the patient may be reminded to purchase a retainer at various points throughout the treatment process (such as at patient intake, prior to beginning treatment, at any point during treatment, and following treatment).

The method 1900 commences at step 1902, where the management engine 114 determines whether the patient 124 has selected an option for a retainer fast track. The patient 124 may select an option for a retainer fast track in a manner similar to selecting a dental aligner fast track option as described above. Where the patient 124 selected the retainer fast track option, the method 1900 may proceed to step 1904. However, where the patient 124 has not selected the retainer fast track option, the method 1900 may proceed to step 1906. Each of steps 1904 and 1906 may commence at a threshold number of days (such as 14 days) prior to completion of the treatment plan.

At step 1904, the messaging system 126 may transmit a notification to the patient computing device 122 which indicates that the patient's retainer is to be produced. Where the retainer order is declined (e.g., due to a fabrication defect, due to an inaccurate intraoral scan or impressions, expired 3D data corresponding to the final position of the patient's teeth, due to other errors encountered in processing the order, etc.), at step 1908, the patient may receive a notification (e.g., a text message) indicating that the retainer order has been declined. At step 1910, the patient may receive another notification (e.g., a follow-up phone call) which also indicates that the retainer order has been declined.

At step 1912, approximately two days following the messaging system 126 transmitting the notification at step 1904, a customer care (CC) team associated with the manufacturer may place an order for the retainer. At step 1914, the messaging system 126 may transmit a notification to the patient computing device 122 (e.g., a text message, an email, etc.) which confirms the patient's retainer has been ordered. At step 1916, following production of the retainer (which may take approximately 14 days from placement of the order at step 1912 and confirmation at step 1914), the messaging system 126 may transmit a notification to the patient computing device 122 (e.g., a text message, an email, etc.) which indicates that the patient's retainers have been shipped to the patient. The notification may include tracking information, instructions on how to wear and care for the retainer, etc. At step 1918, the messaging system 126 may also transmit a notification to the patient computing device 122 when the retainer is delivered to the patient. At step 1920, following delivery of the retainers, the messaging system 126 may transmit a notification (such as an email) to the patient computing device 122 which requests a review on a third-party website (e.g., a YOTPO retainer review). The notification may include a link to the third-party website where the patient may submit a review. At step 1922, the messaging system 126 may transmit, send, or otherwise provide a retainer subscription stream (or other video) which indicates or otherwise provides information relating to a promotion for a retainer subscription program.

Referring back to step 1902, where the patient 124 has not selected the retainer fast track option, the method 1900 may proceed to step 1906. At step 1906, the messaging system 126 may transmit a notification (e.g., a text message) to the patient computing device 122 which reminds the patient to purchase a retainer. At step 1924, the messaging system 126 may transmit a notification (e.g., an email) to the patient computing device 122 which also reminds the patient to purchase a retainer. The notification may include a retainer sales email 1926, which may include various promotions, indicate various benefits for wearing retainers, and so forth. In some embodiments, the notifications sent at steps 1906 and 1924 may be sent at substantially the same time. In some embodiments, the notifications may be sent on the same day but at separate times. At step 1928, the messaging system 126 may transmit another notification to the patient computing device 122. The notification may include another retainer sales email which may be similar to the sales email described above with respect to step 1924. The notification may include a text message 1930. The messaging system 126 may transmit the notification a predetermined duration (e.g., seven days). following transmitting the notifications at step 1906 and 1924. At step 1932, the messaging system 126 may transmit a third retainer sales email to the patient computing device 122 (which may be similar to the previous retainer sales emails described above). The messaging system 126 may transmit the third retainer sales email a predetermined number of days (such as four days) from sending the notification at step 1928, or a predetermined number of days (such as three days) from completion of the treatment plan.

At step 1934, once the patient has completed the treatment plan, the messaging system 126 may transmit a notification (such as a text message) to the patient computing device 122. The notification may indicate that the patient has completed treatment and should purchase a retainer. At step 1936, the messaging system 126 may transmit notification (e.g., another retainer sales email) to the patient computing device 122. At step 1938, the messaging system 126 may initiate a phone call with a mobile device (or other phone) corresponding to the patient (which may be the patient computing device 122). In some embodiments, the phone call may be an automated phone call which includes a pre-recorded message instructing or reminding the patient to purchase a retainer. In some embodiments, the messaging system 126 may initiate the phone call by causing an operator or other personnel associated with the manufacturer to call the mobile device corresponding to the patient.

At step 1940, once the patient has completed the treatment plan, the messaging system 126 may transmit a notification to the patient computing device 122. The notification may be a "celebration email" indicate that the patient has completed their treatment plan. The method 1900 may proceed to steps 1942 and 1948.

At step 1942, following completion of the treatment plan, the messaging system 126 may transmit a notification to the patient computing device 122 which refers the patient to the dental office 118 which is within a predetermined location from the patient (such as within 25 miles of the patient). The messaging system 126 may transmit the notification to the patient computing device 122 following a predetermined duration (such as seven days) from completion of the treatment plan. The patient may be referred to the dental office 118 in which the patient received their intraoral scan or impressions (e.g., as described above). At step 1944, the management engine 114 may determine whether the patient has purchased a retainer. The management engine 114 may access the patient file corresponding to the patient to determine whether the patient file has an indicator, flag, or other status which indicates that the patient has purchased a retainer. If the patient has purchased a retainer, the method 1900 proceeds to a retainer subscription method, which may be similar in some aspects to the method 1800 described in greater detail above. For example, the retainer subscription method may include various combinations of notifications sent to the patient computing device 122 which instruct or remind the patient of how to use and care for their retainer, referring friends to treatment via dental aligners, virtual check-ins, and so forth.

At step 1948, the messaging system 126 may initiate a phone call with a mobile device (or other phone) corresponding to the patient (which may be the patient computing device 122). In some embodiments, the phone call may be an automated phone call which includes a pre-recorded message instructing or reminding the patient to purchase a retainer. In some embodiments, the messaging system 126 may initiate the phone call by causing an operator or other personnel associated with the manufacturer to call the mobile device corresponding to the patient. In some embodiments, the messaging system 126 may initiate the phone call following a predetermined duration from completion of the treatment plan (such as three days following completion of the treatment plan). At step 1950, the messaging system 126 may initiate another phone call with the patient, which may be similar to the phone call initiated at steps 1938 and 1948. The messaging system 126 may initiate the phone call a predetermined duration from the phone call initiated at step 1948 (or from completion of the treatment plan), such as four days after the phone call at step 1948, seven days after completion of the treatment plan, etc. At step 1952, the messaging system 126 may transmit a notification (e.g., a text message) to the patient computing device 122 which remind the patient to purchase a retainer. The messaging system 126 may transmit the notification a predetermined duration from the phone call initiated at step 1950, such as two days following the phone call.

At step 1954, the messaging system 126 initiates one or more phone calls with the patient within a range (such as 11-18 days) following completion of the treatment plan. In some embodiments, the messaging system 126 may initiate a plurality of phone calls (such as daily phone calls, phone calls every other day, etc.). Each of the phone calls may be similar to the phone calls described above. At step 1956, the messaging system 126 may transmit a notification (such as a text message) to the patient computing device 122. The messaging system 126 may transmit the notification to the patient computing device a predetermined duration (such as 18 days) following completion of the treatment plan. At step 1958, the messaging system 126 may transmit various broadcast notifications (e.g., emails) regarding purchasing the retainer to the patient computing device 122. The messaging system 126 may transmit broadcast notifications at various intervals (e.g., every other day, weekly, every other week, etc.).

In some embodiments, where the patient purchases a retainer, the management engine 114 may update the patient file to reflect the patient purchasing the retainer. The method 1900 may be interrupted when the patient purchases the retainers such that one or more of the notifications or phone calls are not provided to the patient which remind the patient to purchase a retainer. In some embodiments, responsive to the patient purchasing a retainer, the method 1900 proceeds to the retainer subscription stream as described above with respect to step 1946.

Figure 20:
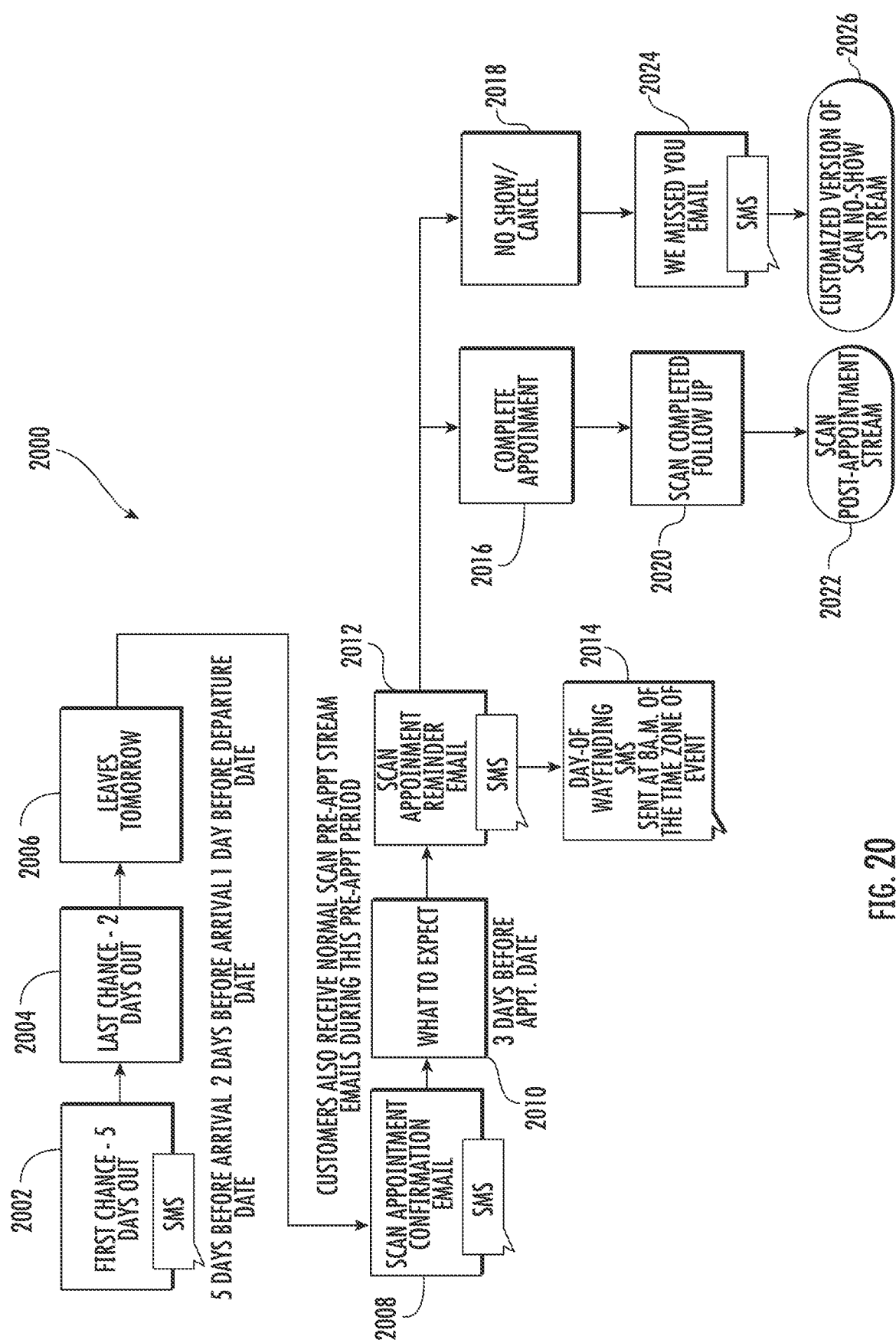
FIG. 20 is a flowchart showing a method of providing notifications regarding an appointment at a dental office, according to an illustrative embodiment.

Referring now to FIG. 20, a method 2000 of providing notifications regarding an appointment at a dental office 118 is shown, according to an example embodiment. In some embodiments, the dental office 118 may include a "pop-up" scanning location. For example, a dental aligner manufacturer may set up a "pop-up" scanning site (similar to the intraoral scanning site 120 described above) within a dental office 118. In some implementations, the pop-up scanning site may be temporary space within the dental office 118. For example, the pop-up scanning site may be maintained at the dental office 118 for a fixed duration (such as a day, a number of days, a week, a month, etc.). The pop-up scanning site may be similar in some aspects to the pop-up scanning sites described in U.S. patent application Ser. No. 16/577,912, titled "Systems and Methods for Mobile Dentition Scanning," filed Sep. 20, 2019, the contents of such application are incorporated herein by reference in its entirety. As described in greater detail below, the messaging system 126 may generate and transmit one or more notifications to customers or potential patients within a predetermined range of the pop-up scanning site.

The management engine 114 may identify potential customers as leads. The management engine 114 may be configured to receive, identify, or otherwise register one or more leads for patients who may be candidates for orthodontic treatment via dental aligners. In some embodiments, leads may be identified based on a predetermined radius (or "geofence"), such as within 40 miles, between the patient and the dental office 118 having a pop-up scanning site. In some embodiments, leads may be identified based on a combination of a predetermined geofence and a patient having self-administered dental impressions rejected or a retake dental impression kit sent to the patient, or a treatment plan which was generated for the patient having expired (e.g., following a predetermined duration, such as a number of months or years, from generation of a treatment plan without the patient initiating treatment via the dental aligners). In some embodiments, the management engine 114 may identify leads within a variable geofence. For example, the management engine 114 may identify leads within a geofence of 60 miles from the dental office 118 having a pop-up scanning site for patients which have rescheduled an appointment at an intraoral scanning site 120, and identify leads within a geofence of 80 miles from the dental office 118 having a pop-up scanning site for patients which had a dental impression kit returned, who require a retake dental impression kit, or had photographs rejected.

At step 2002, the messaging system 126 transmits a notification to the patient computing device 122. The messaging system 126 may transmit the notification a predetermined duration from the pop-up scanning site being launched at the dental office 118. The notification may indicate that the pop-up scanning site will be launched within a number of days (such as five days). The notification may include a link to schedule an appointment at the dental office 118. The patient may select the link to schedule an appointment via the management engine 114 at the dental office. At step 2004, the messaging system 126 transmit another notification to the patient computing device 122. The messaging system 126 may transmit the notification subsequent to the first notification sent at step 2002 (such as three days following sending the first notification, or two days prior to the pop-up scanning site being launched at the dental office 118). The notification sent at step 2004 may be similar to the notification sent at step 2002. At step 2006, the messaging system 126 may transmit a notification to the patient computing device 122 which indicates a departure or closing date corresponding to the pop-up scanning site at the dental office 118. The notification may indicate appointments are still available, and instruct or otherwise direct the patient to generate an appointment prior to the pop-up scanning site closing. The messaging system 126 may transmit the notification to the patient computing device 122 a predetermined duration from the pop-up scanning site closing (such as the day before the pop-up scanning site is to be closed).

At step 2008, where the patient schedules an appointment at the pop-up scanning site at the dental office 118 (either through the management engine 114 as described above or directly with the dental office 118), the messaging system 126 may transmit a notification to the patient computing device 122 which confirms the patient's appointment. The notification may be on include an email to an email account of the patient, a text message to the patient's mobile device, etc. At step 2010, the messaging system 126 may transmit a notification to the patient computing device 122. The messaging system 126 may transmit the notification a predetermined duration from the patient's scheduled appointment (such as three days prior to the scheduled appointment). The notification may include various information regarding the appointment (such as what to expect during the appointment, what the patient should bring to the appointment, information regarding the pop-up scanning site, information regarding potential treatment, etc.). Similar to the notification described in step 2008, the notification may be an email, a text message, etc. At step 2012, the messaging system 126 may transmit a notification to the patient computing device 122 on the day of the patient's scheduled appointment. The notification may be or include an appointment reminder. In some embodiments, the notification may be a text message. The notification may include a day-of wayfinding text message 2014 (similar to the messages described above). The day-of wayfinding text message 2014 may include various details on how to arrive at the dental office 118, where to park, when to leave for the appointment, etc.

The management engine 114 may be configured to determine whether the patient attended the appointment. For example, the office computing device 116 (or other computing device at the pop-up scanning site) may transmit a command or other signal (e.g., via the patient intake portal 128) to the central processing system 102. The command or signal may indicate whether or not the patient attended the appointment. The management engine 114 may be configured to receive the command or signal indicating whether the patient attended the appointment. The management engine 114 may update the patient file according to the received command or signal. At step 2016, the management engine 114 determines that the patient attended the appointment, and at step 2018, the management engine 114 determines that the patient did not attend the appointment (e.g., either by not showing up to the appointment or canceling the appointment).

Where, at step 2016, the management engine 114 determines that the patient attended the appointment, at step 2020, the messaging system 126 may transmit a notification to the patient computing device 122. The notification may include a scan completed follow-up notification. The notification may include information relating to next steps following the patient's intraoral scan, information on when the patient would receive dental aligners, etc. Following sending the notification at step 2020, at step 2022, the method 2000 may proceed to a scan post-appointment method, which may be similar in some regards to method 1600 described above with respect to FIG. 16.

If, at step 2018, the management engine 114 determines that the patient did not attend the appointment, at step 2024, the messaging system 126 transmits a notification to the patient computing device 122. The notification may include a "We Missed You" notification, which may be an email, text message, etc. The notification may include information relating to rescheduling an appointment at the pop-up scanning site or other location, information relating to at-home impression kits, etc. The notification may include various promotions for impression kits or intraoral scans. Following sending the notification at step 2024, at step 2026, the method 2000 may proceed to a scan no-show method, which may be similar in some regards to method 1600 described above with respect to FIG. 16. In some embodiments, the scan no-show method may include various steps which are customized to the patient.

Figure 21:
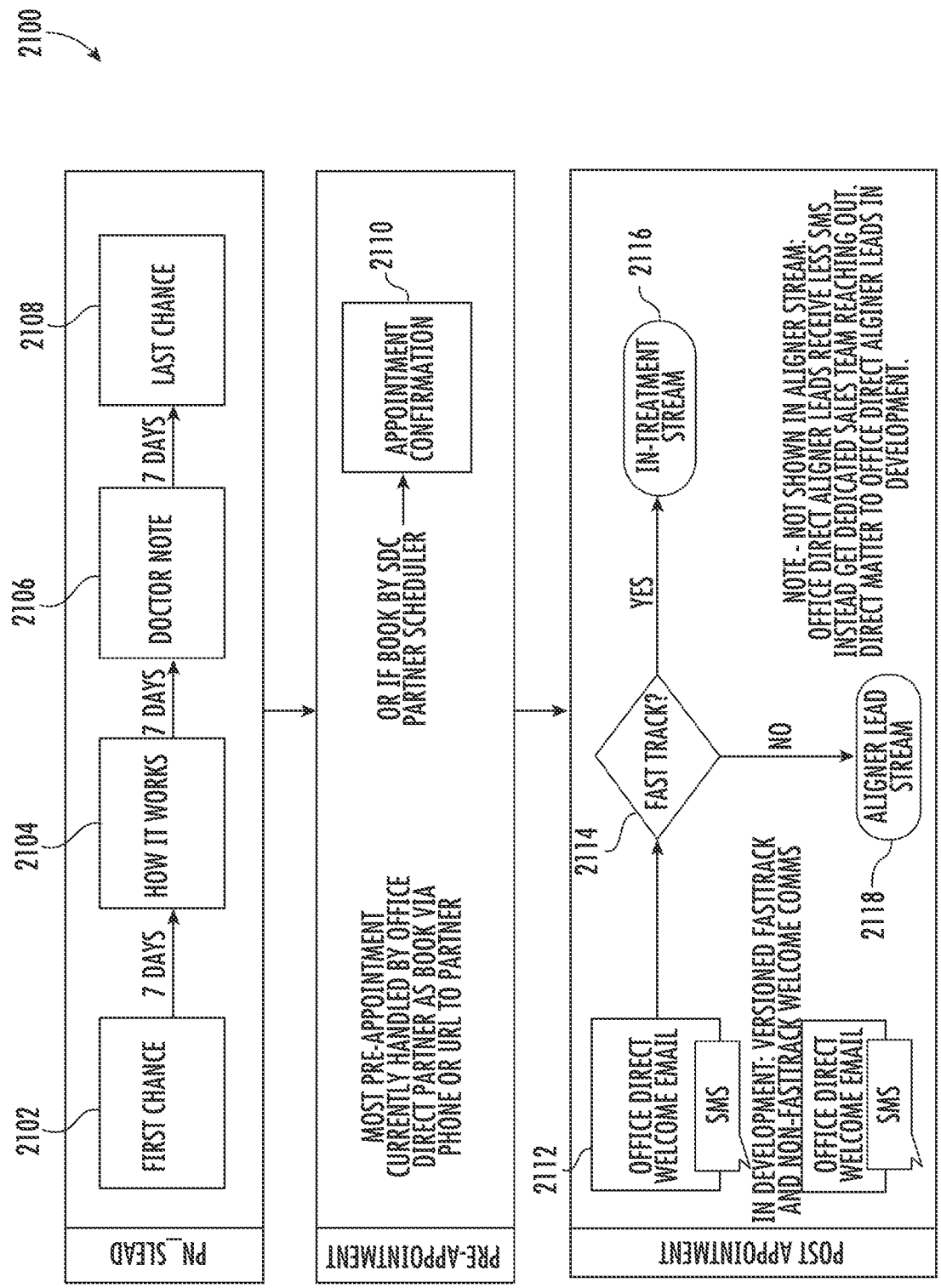
FIG. 21 is a flowchart showing a method of providing notifications regarding an appointment at a dental office, according to an illustrative embodiment.

Referring now to FIG. 21, a method 2100 of providing notifications regarding an appointment at a dental office 118 is shown, according to an example embodiment. In some embodiments, the dental office 118 may include a dedicated scanning location within the dental office 118. For example, and as described above, the dental office 118 may enroll with the central processing system 102 to provide intraoral scans to patients seeking treatment via dental aligners.

The management engine 114 may identify potential customers as leads. As described above, the management engine 114 may be configured to receive, identify, or otherwise register one or more leads for patients who may be candidates for orthodontic treatment via dental aligners. In some embodiments, leads may be identified based on a predetermined radius (or "geofence"), such as within 25 miles, between the patient and an enrolled dental office 118. In some embodiments, leads may be identified based on a combination of a predetermined geofence and a patient having previously been identified as a candidate for orthodontic treatment via dental aligners. For example, a patient may have previously identified as a candidate for orthodontic treatment by scheduling an appointment at an intraoral scanning site 120 and not showing up or canceled, obtaining an at-home dental impression kit and not returning administered impressions, etc. The management engine 114 may identify such candidates as leads following a predetermined duration (such as 210 days) from scheduling a previous appointment, obtaining the at-home impression kit, etc.

At step 2102, the messaging system 126 transmits a first notification to a patient computing device 122 associated with a lead identified by the management engine 114 as described above. The first notification may be sent as an email, text message, etc. The first notification may indicate that a dental office 118 is located nearby the patient. The first notification may prompt the patient to schedule an appointment at the dental office 118 to receive an intraoral scan. In some embodiments, the first notification may include a link for scheduling the appointment through the management engine 114 at the dental office 118. In some embodiments, the first notification may instruct the user to schedule an appointment with the dental office 118 directly (e.g., via a website or uniform resource locator ("URL") for the dental office 118, via a phone number for the dental office 118, etc.).

At step 2104, the messaging system 126 transmits a second notification to the patient computing device 122. The second notification may include various information relating to the intraoral scanning process at the dental office 118. The second notification may include aspects similar to those described above with respect to the first notification. The second notification may include instructions for scheduling an appointment at the dental office 118. At step 2106, the messaging system 126 transmits a third notification to the patient computing device 122. The third notification may include a note from a dentist or orthodontist of the dental office 118. The note may include benefits of orthodontic treatment via dental aligners identified by the dentist or orthodontist, various information about the dentist or orthodontist or the dental office 118, etc. At step 2108, the messaging system 126 transmits a fourth notification to the patient computing device 122. The fourth notification may include a "Last Chance" notification which may be similar in some respects to the notifications sent at steps 2102 and 2104.

Where the patient schedules an appointment for an intraoral scan at the dental office 118, the patient may receive one or more notifications or reminders. For example, where the patient schedules the appointment directly with the office (e.g., via the dental office 118 website or via a phone number), the dental office 118 may provide one or more reminders. Where the patient schedules the appointment via the management engine 114, at step 2110, the messaging system 126 may transmit an appointment confirmation notification to the patient computing device 122.

At step 2112, following the patient attending the scheduled appointment, the messaging system 126 may transmit a notification to the patient computing device 122. In some embodiments, the notification may be or include a "welcome" email or text message which provides various information to the patient regarding treatment. In some embodiments, the notification provided at step 2112 may be different depending on whether or not the patient opted for a fast-track option at the dental office 118 as described above. At step 2114, the management engine 114 may determine whether or not the patient opted for a fast track option. The management engine 114 may access the patient file to determine whether the patient selected a fast track option at the dental office 118. At step 2116, where the patient selected a fast track option, the method 2100 may proceed to an in-treatment method, which may be similar in some aspects to method 1800 described above. However, at step 2118, where the patient did not select a fast track option, the method 2100 may proceed to an aligner lead method, which may be similar in some aspects to method 1700 described above. In some embodiments, steps 2116 and 2118 may include fewer text messages than methods 1800 and 1700 described above. Rather, steps 2116 and 2117 may include more notifications or phone calls from dedicated sales team members, direct mailers, etc.

Figure 22:
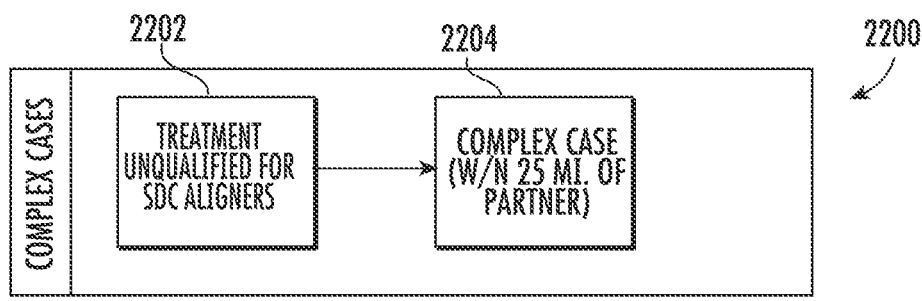
FIG. 22 is a flowchart showing a method of referring a patient to a dental office, according to an illustrative embodiment.

Referring now to FIG. 22, a method 2200 of referring a patient to a dental office 118 is shown, according to an example embodiment. Method 2200 begins at step 2202, where the management engine 114 determines whether a patient is qualified for treatment via dental aligners. As described above, following receiving an intraoral scan, an approving dentist or orthodontist may use the approving dental computing device 138 to access the approving dental portal 136. The approving dentist or orthodontist may determine whether the patient is fit for treatment via dental aligners. The approving dentist or orthodontist may select a button on the approving dental computing device 138 of the approving dental portal 136 to approve or deny the patient for treatment via dental aligners. Where the dentist or orthodontist approves the patient as being fit for treatment via dental aligners, the approving dental computing device may transmit a command or other signal via the approving dental portal 136 for the management engine 114 to update the patient file to indicate the patient is fit for treatment. On the other hand, where the dentist or orthodontist denies the patient as being fit for treatment via dental aligners, the approving dental computing device may transmit a command or other signal via the approving dental portal 136 for the management engine 114 to update the patient file to indicate the patient is not fit for treatment. The management engine 114 may access the patient file to determine whether the patient is fit for treatment. Where the patient is not fit for treatment, the method 2200 may proceed to step 2204.

At step 2204, the messaging system 126 may transmit one or more notifications to the patient computing device 122. The notification may indicate that the patient is not a candidate for orthodontic treatment via dental aligners. The notification may include one or more referrals to dentists or orthodontists within a predetermined distance from the patient (such as within 25 miles of the patient). In some implementations, the messaging system 126 may select one or more dental offices 118 within the network of dental offices 118 to which the patient is to be referred. The notification may include contact information for the dental office 118, may include various buttons to select an option to schedule an appointment with the dental office 118, etc.

Figure 23:
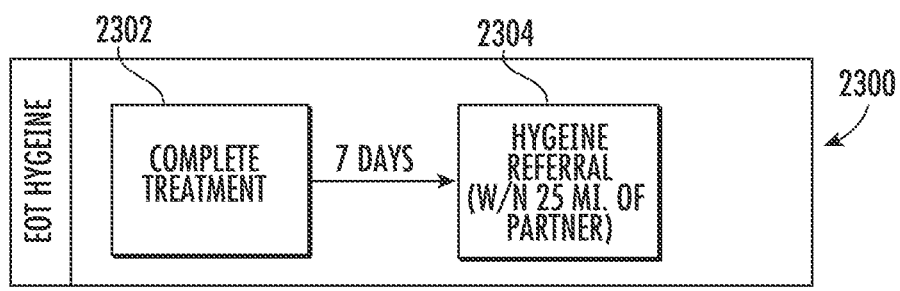
FIG. 23 is a flowchart showing a method of referring a patient to a dental office for a hygiene appointment, according to an illustrative embodiment.

Referring now to FIG. 23, a method 2300 of referring a patient to a dental office 118 for a hygiene appointment is shown, according to an example embodiment. Method 2300 begins at step 2302, where the management engine 114 determines whether a patient has completed treatment via dental aligners. The management engine 114 may determine that the patient has completed treatment via dental aligners as described above with respect to FIG. 19. When the management engine 114 determines that the patient has completed treatment, the method 2300 may proceed to step 2304.

At step 2304, the messaging system 126 may transmit one or more notifications to the patient computing device 122. The notification may include a referral to a dental office 118 for a hygiene cleaning. The notification may include one or more referrals to dentists or orthodontists within a predetermined distance from the patient (such as within 25 miles of the patient). In some implementations, the messaging system 126 may select one or more dental offices 118 within the network of dental offices 118 to which the patient is to be referred for a hygiene cleaning. The notification may include contact information for the dental office 118, may include various buttons to select an option to schedule an appointment with the dental office 118, etc.

Method of Fabricating Dental Aligners

Figure 24:
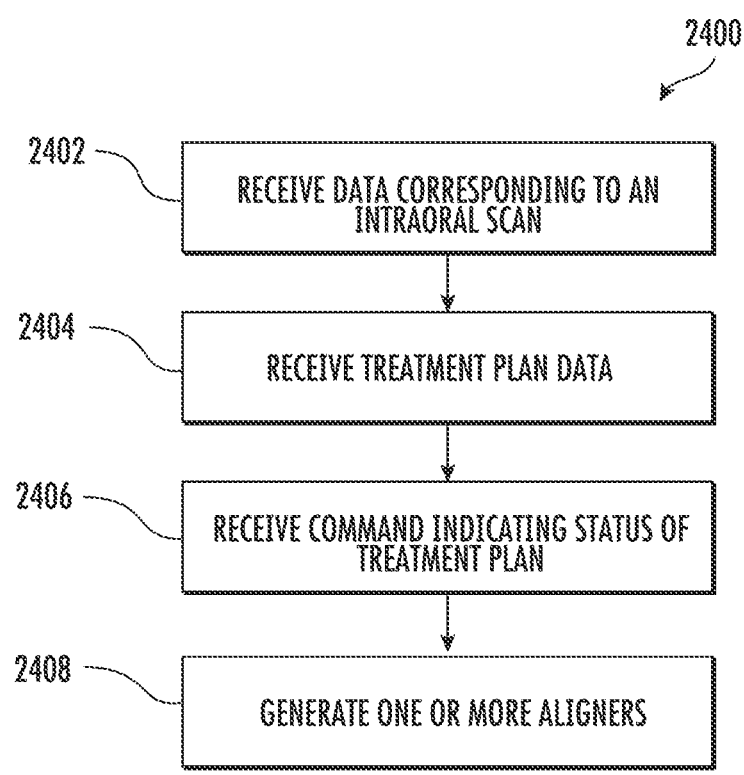
FIG. 24 is a flowchart showing a method of fabricating dental aligners, according to an illustrative embodiment.

FIG. 24 is a flowchart showing a method 2400 of fabricating dental aligners. Each of the steps shown in method 2400 may be performed by the systems, components, or elements described above with reference to FIG. 1—FIG. 23. As a brief overview, at step 2402, a patient intake portal 128 may receive data corresponding to a three-dimensional (3D) representation of a mouth of a patient. At step 2404, a treatment plan portal 134 may receive treatment plan data. At step 2406, an approving dental portal 136 may receive a command which indicates a status of the treatment plan. At step 2408, a dental aligner fabrication system 144 generates one or more dental aligners 146.

At step 2402, a patient intake portal 128 may receive data corresponding to a 3D representation of a mouth of a patient. In some embodiments, the patient intake portal 128 may receive data corresponding to the 3D representation from an office computing device 116 located at a dental office 118 of a first dentist or orthodontist which is to administer the intraoral scan of a patient during a scheduled appointment at the dental office 118. In some embodiments, the patient intake portal 128 may receive an identifier corresponding to an intraoral scan conducted using an intraoral scanner at the dental office 118 from the office computing device 116. In some embodiments, the patient intake portal 128 may receive an indication that the 3D representation was obtained by impressions administered at the dental office 118 from the office computing device 116. The management engine 114 may use the identifier received via the patient intake portal 128 from the office computing device 116 to retrieve a 3D model from an external computing device or system associated with the intraoral scanner. In some embodiments, the patient intake portal 128 may receive the 3D model from the office computing device 116. The office computing device 116 may receive the 3D model from the intraoral scanner directly, or may retrieve (or otherwise receive) the 3D model from the external computing device or system. The office computing device 116 may send, upload, or otherwise provide the 3D model to the patient intake portal 128 for incorporating into a patient file 115 for the patient maintained by the management engine 114.

In some embodiments, a messaging system 126 may transmit a plurality of notifications to the patient computing device 122. The notifications may include notifications corresponding to the appointment being scheduled at the office of the first dentist or orthodontist, a follow-up corresponding to the appointment, the treatment plan, or to prompt payment for the one or more dental aligners. Various examples of notifications are described in greater detail above with respect to FIG. 10—FIG. 23. In some implementations, the notifications may be transmitted to the patient computing device 122 according to a cadence. For example, the notifications may be sent more often or frequently depending on whether the patient 124 has an appointment at the dental office 118 or at an intraoral scanning site 120.

In some embodiments, the patient intake portal 128 may receive intake data from the office computing device 116. The intake data may correspond to the patient which received the intraoral scan or impressions. For example, the intake data may include dental history information (such as the information obtained via the user interface 400 described with reference to FIG. 4), intake photographs or images (such as the photographs uploaded via the user interface 700 described with reference to FIG. 7), etc. The office computing device 116 may upload, transmit, or otherwise provide the intake data upon generating a new case for the patient using the patient intake portal 128 as described above with reference to FIG. 2—FIG. 8. The patient intake portal 128 may receive the intake data and data corresponding to the intraoral scan from the office computing device 116. The management engine 114 may update the patient file 115 for the patient to include the patient intake data and data corresponding to the intraoral scan or impressions.

At step 2404, a treatment plan portal 134 may receive treatment plan data based on the data corresponding to the intraoral scan or impressions. In some embodiments, the treatment plan portal 134 may receive treatment plan data generated by the treatment plan computing device 132 based on the data corresponding to the intraoral scan or impressions. The treatment plan computing device 132 may access the treatment plan portal 134 to retrieve or otherwise receive a 3D model corresponding to an initial position of the patient's teeth. The treatment plan computing device 132 may generate the treatment plan based on the 3D model of the initial position of the patient's teeth. In some embodiments, the data corresponding to the treatment plan includes a plurality of three-dimensional (3D) models representative of a progression of one or more teeth of the patient from a first position (e.g., the initial position) to a second position (e.g., a final position). Each of the 3D models may represent a particular stage of the treatment plan (e.g., a first 3D model for the initial position, one or more intermediate 3D models corresponding to intermediate positions, and a final 3D model corresponding to a final position).

At step 2406, an approving dental portal 136 may receive a command which indicates an approval or denial status of the treatment plan. In some embodiments, the approving dental portal may receive a command from an approving dental computing device 138 corresponding to a second dentist or orthodontist. The approving dental computing device 138 may access the treatment plan data via the approving dental portal 136. The command may indicate an approval or denial status of the treatment plan. The second dentist or orthodontist may review the treatment plan data via the approving dental portal 136 to approve or deny the treatment plan. When the dental professional approves the treatment plan, the dental professional may select an option or button on a user interface of the approving dental portal 136. Responsive to the dental professional selecting the button on the user interface, the approving dental computing device 138 may transmit a command to the approving dental portal 136 to indicate the approval or denial status of the treatment plan. In some embodiments, the patient 124 may similarly access the patient portal 140 via the patient computing device 122 to approve the treatment plan. The patient may view data corresponding to the treatment plan, which may include an animation or other graphical/visual representation of the progression of the patient's teeth. The patient may select an option or button on a user interface of the patient portal 140 to indicate the patient's approval or denial of the treatment plan. Responsive to the patient 124 selecting the button on the user interface, the patient computing device 122 may transmit a command to the patient portal 140 to indicate the approval or denial status of the treatment plan. The management engine 114 may update the patient file 115 responsive to receipt of the command(s) via the approving dental portal 136 and/or the patient portal 140.

At step 2408, a dental aligner fabrication system 144 generates one or more dental aligners 146 based on the treatment plan. The one or more dental aligners may be specific to the patient and are configured to reposition one or more teeth of the patient in accordance with the treatment plan generated for the patient. The fabrication system 144 may generate the dental aligners 146 by 3D printing (e.g., using the 3D printing system 150) or otherwise casting physical models corresponding to the 3D models. The physical models may thus represent the stages of the treatment plan. A thermoforming system 152 may thermoform material to the physical models, and may trim the thermoformed material from the physical models to produce dental aligners 146. In some implementations, the fabrication system 144 may generate the dental aligners 146 by 3D printing the dental aligners directly based on the 3D models corresponding to the treatment plan.

In some embodiments, the shipment processing system 154 may cause shipment of the dental aligners 146 to the patient 124. In some embodiments, the shipment processing system 154 may package the dental aligners 146 in sequence and ship the packaged aligners to the patient 124. In some embodiments, the shipment processing system 154 may be configured to ship the packaged dental aligners 146 to an address specified by the patient during patient intake as described above with reference to FIG. 3. In some embodiments, the shipment processing system 154 may be configured to ship the packaged dental aligners 146 to an address specified by the patient using an input provided by the patient computing device 122 to the patient portal 140. In these and other embodiments, the patient may provide an input to the office computing device 116 or patient computing device 122 which indicates a home or work address corresponding to the patient. The shipment processing system 154 may receive the address specified by the patient for shipment of the dental aligners 146. The shipment processing system 154 may ship the dental aligners 146 to the address specified to the patient. The shipment processing system 154 may be configured to ship the dental aligners 146 by providing the packaged dental aligners 146 to one or more carriers which transport the packaged dental aligners 146 to the address specified by the patient. In these embodiments, the dental aligners 146 may be sent to the patient without first providing the dental aligners 146 to the approving dental professional, to the dental office 118 or intraoral scanning site 120, or other entities associated with the generation/approval of the treatment plan.

The construction and arrangement of the systems and methods as shown in the various exemplary embodiments are illustrative only. Although only a few embodiments have been described in detail in this disclosure, many modifications are possible (e.g., variations in sizes, dimensions, structures, shapes and proportions of the various elements, values of parameters, mounting arrangements, use of materials, orientations, etc.). By way of example, the position of elements may be reversed or otherwise varied and the nature or number of discrete elements or positions may be altered or varied. Accordingly, all such modifications are intended to be included within the scope of the present disclosure. The order or sequence of any process or method steps may be varied or re-sequenced according to alternative embodiments. Other substitutions, modifications, changes, and omissions may be made in the design, operating conditions and arrangement of the exemplary embodiments without departing from the scope of the present disclosure.

The present disclosure contemplates methods, systems and program products on memory or other machine-readable media for accomplishing various operations. The embodiments of the present disclosure may be implemented using existing computer processors, or by a special purpose computer processor for an appropriate system, incorporated for this or another purpose, or by a hardwired system. Embodiments within the scope of the present disclosure include program products or memory comprising machine-readable media for carrying or having machine-executable instructions or data structures stored thereon. Such machine-readable media may be any available media that may be accessed by a general purpose or special purpose computer or other machine with a processor. By way of example, such machine-readable media can comprise RAM, ROM, EPROM, EEPROM, CD-ROM or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. Combinations of the above are also included within the scope of machine-readable media. Machine-executable instructions include, by way of example, instructions and data which cause a general purpose computer, special purpose computer, or special purpose processing machines to perform a certain function or group of functions.

Although the figures may show a specific order of method steps, the order of the steps may differ from what is depicted. Also, two or more steps may be performed concurrently or with partial concurrence. Such variation will depend on the software and hardware systems chosen and on designer choice. All such variations are within the scope of the disclosure. Likewise, software implementations could be accomplished with standard programming techniques with rule based logic and other logic to accomplish the various connection steps, processing steps, comparison steps and decision step.

What is claimed is:

1. A distributed system comprising:
one or more servers communicably coupled to a plurality of computing devices that are located remote from one another, wherein the one or more servers are configured by machine-readable instructions to provide the plurality of computing devices access to a plurality of portals hosted by the one or more servers, wherein the plurality of portals comprise:
a patient intake portal configured to be accessed by a first computing device located at an office of an intake dentist or orthodontist, wherein the patient intake portal is configured to receive data regarding a three-dimensional (3D) representation of a mouth of a patient obtained during an appointment at the office; and
an approving portal configured to be accessed by a second computing device remote from the first computing device, wherein the approving portal is configured to provide the second computing device access to treatment plan data generated from the 3D representation of the mouth of the patient obtained at the office of the intake dentist or orthodontist, wherein the approving portal is configured to receive a command from the second computing device that indicates an approval status of a treatment plan corresponding to the treatment plan data; and
a dental aligner fabrication system comprising:
a fabrication computing device configured to receive the treatment plan data; and
dental aligner fabrication equipment configured to fabricate one or more dental aligners based on the treatment plan data, wherein the one or more dental aligners are specific to the patient and are configured to reposition one or more teeth of the patient in accordance with the treatment plan generated for the patient;
wherein the patient intake portal is further configured to provide a plurality of status updates to the intake dentist or orthodontist regarding a status of the patient, and wherein the plurality of status updates include an indication that the one or more dental aligners have been sent to the patient.

2. The system of claim 1, wherein the plurality of portals further comprise a treatment plan portal configured to be accessed by a third computing device remote from the first computing device and the second computing device, wherein the treatment plan portal is configured to provide the third computing device access to a 3D model of the mouth of the patient, wherein the 3D model is generated based on the 3D representation, and wherein the treatment plan portal is configured to receive the treatment plan data generated by the third computing device based on the 3D model.

3. The system of claim 1, wherein the 3D representation is obtained from dental impressions administered during the appointment at the office of the intake dentist or orthodontist.

4. The system of claim 3, wherein the data regarding the 3D representation comprises an indication that the 3D representation was obtained using the dental impressions.

5. The system of claim 1, wherein the 3D representation comprises an intraoral scan administered during the appointment at the office of the intake dentist or orthodontist, and wherein the data regarding the 3D representation comprises intraoral scan data.

6. The system of claim 5, wherein the intraoral scan data comprises at least one of the 3D model or an identifier used to access the 3D model.

7. The system of claim 1, wherein the treatment plan is a second treatment plan generated for the patient and the 3D representation is a second 3D representation, wherein the one or more dental aligners are one or more second dental aligners, wherein the patient has a one or more first dental aligners manufactured based on a first treatment plan which was generated for the patient, and wherein the first treatment plan associated with the patient is identified for a mid-course correction.

8. The system of claim 1, wherein the treatment plan data comprises a plurality of three-dimensional (3D) models representative of a progression of one or more teeth of the patient from a first position to a second position.

9. The system of claim 1, wherein the command is a first command, and wherein the plurality of portals further comprise a patient portal configured to be accessed by a third computing device corresponding to the patient for accessing the treatment plan data, wherein the patient portal is configured to receive a second command from the third computing device that indicates an approval or denial status of the treatment plan by the patient.

10. The system of claim 1, wherein the patient intake portal is further configured to display a report including a status of a plurality of patients including the status of the patient.

11. The system of claim 1, wherein the plurality of status updates include at least one of an indication that the patient is scheduled to receive the dental aligners or the patient has received the dental aligners.

12. A method comprising:
receiving, by one or more servers via a patient intake portal from a first computing device located at an office of an intake dentist or orthodontist, data regarding a three-dimensional (3D) representation of a mouth of a patient obtained during an appointment at the office;
providing, by the one or more servers via an approving portal to a second computing device remote from the first computing device, access to treatment plan data generated from the 3D representation of the mouth of the patient obtained at the office of the intake dentist or orthodontist,
receiving, by the one or more servers via the approving portal from the second computing device, a command that indicates an approval status of the treatment plan data;
transmitting, by the one or more servers, the treatment plan data to a fabrication computing device;
fabricating, using dental aligner fabrication equipment, one or more dental aligners based on the treatment plan data, wherein the one or more dental aligners are specific to the patient and are configured to reposition one or more teeth of the patient in accordance with a treatment plan generated for the patient; and
providing, by the one or more servers via the patient intake portal, a plurality of status updates to the intake dentist or orthodontist regarding a status of the patient, wherein the plurality of status updates include an indication that the one or more dental aligners have been sent to the patient.

13. The method of claim 12, further comprising receiving, by the one or more servers via a treatment plan portal from a third computing device, the treatment plan data generated by the third computing device based on a 3D model of the mouth of the patient, wherein the 3D model is generated based on the 3D representation obtained during the appointment.

14. The method of claim 12, wherein the 3D representation is obtained from dental impressions administered during the appointment at the office of the intake dentist or orthodontist.

15. The method of claim 14, wherein the data regarding the 3D representation comprises an indication that the 3D representation was obtained using the dental impressions.

16. The method of claim 12, wherein the 3D representation comprises an intraoral scan administered during the appointment at the office of the intake dentist or orthodontist, and wherein the data regarding the 3D representation comprises intraoral scan data.

17. The method of claim 16, wherein the intraoral scan data comprises at least one of the 3D model or an identifier used to access the 3D model.

18. The method of claim 12, wherein the treatment plan is a second treatment plan generated for the patient and the 3D representation is a second 3D representation, wherein the one or more dental aligners are one or more second dental aligners, wherein the patient has a one or more first dental aligners manufactured based on a first treatment plan which was generated for the patient, and wherein the first treatment plan associated with the patient is identified for a mid-course correction.

19. The method of claim 12, wherein the treatment plan data comprises a plurality of three-dimensional (3D) models representative of a progression of one or more teeth of the patient from a first position to a second position.

20. The method of claim 12, further comprising providing, by the one or more servers via the patient intake portal, a report including a status of a plurality of patients including the status of the patient.

21. The method of claim 12, wherein the command is a first command, and wherein the method further comprises receiving, via a patient portal accessed by a third computing device corresponding to the patient, a second command from the third computing device that indicates an approval or denial status of the treatment plan by the patient.

22. A distributed system comprising:
one or more servers communicably coupled to a plurality of computing devices that are located remote from one another, wherein the one or more servers are configured by machine-readable instructions to provide the plurality of computing devices access to a plurality of portals hosted by the one or more servers, wherein the plurality of portals comprise:

a patient intake portal configured to be accessed by a first computing device located at an office of an intake dentist or orthodontist, wherein the patient intake portal is configured to receive data regarding a three-dimensional (3D) representation of a mouth of a patient obtained during an appointment at the office;

a treatment plan portal configured to be accessed by a second computing device remote from the first computing device, wherein the treatment plan portal is configured to provide the second computing device access to a 3D model of the mouth of the patient, wherein the 3D model is generated based on the 3D representation, and wherein the treatment plan portal is configured to receive treatment plan data generated by the second computing device based on the 3D model;

an approving portal configured to be accessed by a third computing device remote from the first computing device and the second computing device, wherein the approving portal is configured to provide the third computing device access to the treatment plan data, wherein the approving portal is configured to receive a command from the third computing device that indicates an approval status of a treatment plan corresponding to the treatment plan data;

a dental aligner fabrication system comprising dental aligner fabrication equipment configured to fabricate one or more dental aligners based on the treatment plan data, wherein the one or more dental aligners are specific to the patient and are configured to reposition one or more teeth of the patient in accordance with the treatment plan generated for the patient; and wherein the patient intake portal is further configured to provide a plurality of status updates to the intake dentist or orthodontist regarding a status of the patient based on the approval status of the treatment plan or a fabrication status of the one or more dental aligners, and wherein the plurality of status updates include an indication that the one or more dental aligners have been sent to the patient.

\* \* \* \* \*